(12) United States Patent
Guan et al.

(10) Patent No.: US 11,649,260 B2
(45) Date of Patent: May 16, 2023

(54) FUNCTIONALIZED N-ACETYLGALACTOSAMINE NUCLEOSIDES

(71) Applicant: Hongene Biotech Corporation, Union City, CA (US)

(72) Inventors: Xiaoyang Guan, Fremont, CA (US); David Yu, Union City, CA (US); Ruiming Zou, Union City, CA (US); Xiaoling Zheng, Union City, CA (US); John Liu, Union City, CA (US); Aldrich N. K. Lau, Palo Alto, CA (US); Wing C. Poon, Union City, CA (US); Gang Zhao, Union City, CA (US); Gengyu Du, Union City, CA (US); Yun-Chiao Yao, Union City, CA (US)

(73) Assignee: Hongene Biotech Corporation, Union City, CA (US)

( * ) Notice: Subject to any disclaimer, the term of this patent is extended or adjusted under 35 U.S.C. 154(b) by 0 days.

(21) Appl. No.: 17/842,135

(22) Filed: Jun. 16, 2022

(65) Prior Publication Data

US 2023/0034284 A1 Feb. 2, 2023

Related U.S. Application Data

(60) Provisional application No. 63/212,519, filed on Jun. 18, 2021.

(51) Int. Cl.
| | |
|---|---|
| *C07H 19/06* | (2006.01) |
| *C07H 1/00* | (2006.01) |
| *C07H 19/14* | (2006.01) |
| *A61K 48/00* | (2006.01) |
| *A61K 47/54* | (2017.01) |

(52) U.S. Cl.
CPC ............ *C07H 19/06* (2013.01); *A61K 47/549* (2017.08); *A61K 48/0033* (2013.01); *C07H 1/00* (2013.01); *C07H 19/14* (2013.01)

(58) Field of Classification Search
None
See application file for complete search history.

(56) References Cited

U.S. PATENT DOCUMENTS

| | | | |
|---|---|---|---|
| 7,037,936 | B2 | 5/2006 | McKenna et al. |
| 8,962,580 | B2 | 2/2015 | Manoharan et al. |
| 10,016,518 | B2 | 7/2018 | Anthony et al. |
| 10,294,474 | B2 | 5/2019 | Li et al. |
| 10,662,427 | B2 | 5/2020 | Melquist et al. |
| 10,669,301 | B2 | 6/2020 | Guzaev et al. |
| 10,781,175 | B2 | 9/2020 | Guzaev et al. |
| 2012/0276108 | A1 | 11/2012 | Priebe |
| 2016/0266133 | A1 | 9/2016 | Levy |
| 2018/0064819 | A1 | 3/2018 | Li et al. |
| 2018/0195070 | A1 | 7/2018 | Melquist et al. |
| 2019/0211368 | A1 | 7/2019 | Butora et al. |
| 2019/0225644 | A1 | 7/2019 | Butora et al. |
| 2019/0247468 | A1 | 8/2019 | Mahdavi et al. |
| 2019/0256849 | A1 | 8/2019 | Li et al. |
| 2020/0263179 | A1 | 8/2020 | Melquist et al. |
| 2020/0270611 | A1 | 8/2020 | Gryaznov et al. |

FOREIGN PATENT DOCUMENTS

| | | |
|---|---|---|
| WO | WO 03/039523 | 5/2003 |
| WO | WO 2015/066697 | 5/2015 |
| WO | WO 2017/066789 | 7/2015 |
| WO | WO 2017/066789 | 4/2017 |
| WO | WO 2017/177326 | 10/2017 |
| WO | WO 2018/044350 | 3/2018 |
| WO | WO 2018/067900 | 4/2018 |
| WO | WO 2019/051257 | 3/2019 |
| WO | WO 2019/053661 | 3/2019 |
| WO | WO 2019/075419 | 4/2019 |
| WO | WO 2019/211595 | 11/2019 |
| WO | WO 2020/093061 | 5/2020 |
| WO | WO 2020/093098 | 5/2020 |
| WO | WO 2022/055726 | 3/2022 |
| WO | WO 2022/076922 | 4/2022 |

OTHER PUBLICATIONS

Yamada, J. Org. Chem. 2011, 76, 1198-1211. (Year: 2011).*
Carey, 1992, Organic Chemistry, 2d ed., McGraw-Hill, Inc., New York, pp. 328-331.
Craig et al., 2018, Recent preclinical and clinical advances in oligonucleotide conjugates. Expert Opin. Drug. Deliv. 15(6):629-646.
Debacker et al., 2020, Delivery of Oligonucleotides to the Liver with GalNAc: From Research to Registered Therapeutic Drug. Mol. Ther., 8:1759-1771.
Greene et al., 1999, Protective Groups in Organic Synthesis, 3rd Ed., John Wiley & Sons, New York (TOC).
Huang, 2017, Preclinical and Clinical Advances of GalNAc-Decorated Nucleic Acid Therapeutics. Mol. Ther. Nucleic. Acids., 6:116-132.
IUPAC-IUB Commission on Biochemical Nomenclatures, 1972, Abbreviated nomenclature of synthetic polypeptides (polymerized amino acids), revised recommendations (1971), Biochem. 11(5):942-944.
Li et al., 2012, Identification of a specific inhibitor of nOGA-a caspase-3 cleaved O-GlcNAcase variant during apoptosis, Biochemistry (Moscow), 77(2):194-200.

(Continued)

*Primary Examiner* — Layla D Berry
(74) *Attorney, Agent, or Firm* — Knobbe, Martens, Olson & Bear, LLP

(57) ABSTRACT

Embodiments of the present application relate to N-acetylgalactosamine-conjugated nucleosides. In particular, the N-acetylgalactosamine is installed on the nucleobase of the nucleosides through a wide variety of linkers. Methods of making N-acetylgalactosamine-conjugated nucleosides are also disclosed herein. N-acetylgalactosamine is a well-defined liver-targeted moiety and N-acetylgalactosamine-conjugated nucleosides may be used in the preparation of targeted delivery of oligonucleotide-based therapeutics.

23 Claims, 6 Drawing Sheets

Specification includes a Sequence Listing.

(56) References Cited

OTHER PUBLICATIONS

McMurry, 2000, Organic Chemistry, 5th ed., Brooks/Cole, Pacific Grove, CA, pp. 398 and 408.
McOmie, ed., 1973, Protective Groups in Organic Chemistry, Plenum Press (TOC).
Roberts et al., 2020, Advances in oligonucleotide drug delivery. Nat. Rev. Drug Discov. 10:673-694.
Saneyoshi et al., 2017, Aikyne-linked reduction-activated protecting groups for diverse functionalization on the backbone of oligonucleotides, Bloorganic & Medicinal Chemistry, 25(13):3350-3356.
Scheit, 1980, Nucleotide analogs: Synthesis and biological function. New York: John Wiley & Sons (TOC).
Streitwieser et al., 1981, Introduction to Organic Chemistry, 2d ed., Macmillan Publishing Co., Inc., New York, pp. 169-171.
Uhlman et al., Jun. 1990, Antisense oligonucleotides: a new therapeutic principle, Chemical Reviews, 90(4):543-584.
International Search Report and Written Opinion dated Aug. 12, 2022 in International Patent Application No. PCT/US2022/033781.

\* cited by examiner

SEQUENCE LISTING

<160> NUMBER OF SEQ ID NOS: 10

<210> SEQ ID NO 1
<211> LENGTH: 11

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (1)...(1)
<223> OTHER INFORMATION: wherein dA is conjugated to EO-compound 14

<400> SEQUENCE: 1
attttttttt t                                                              11

<210> SEQ ID NO 2
<211> LENGTH: 11
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (1)...(1)
<223> OTHER INFORMATION: wherein dA is conjugated to (Bz)-EO-compound 19

<400> SEQUENCE: 2
attttttttt t                                                              11

<210> SEQ ID NO 3
<211> LENGTH: 11
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (1)...(1)
<223> OTHER INFORMATION: wherein dU is conjugated to EO-compound 9

<400> SEQUENCE: 3
uttttttttt t                                                              11

<210> SEQ ID NO 4
<211> LENGTH: 11
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (1)...(1)
<223> OTHER INFORMATION: wherein dA is conjugated to
      (Bz)-click-PEG-compound 31

<400> SEQUENCE: 4
attttttttt t                                                              11

<210> SEQ ID NO 5
<211> LENGTH: 11
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (1)...(1)
<223> OTHER INFORMATION: wherein dU is conjugated to click-PEG-compound
      25

<400> SEQUENCE: 5
uttttttttt t                                                              11
```

-continued

```
<210> SEQ ID NO 6
<211> LENGTH: 11
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (11)...(11)
<223> OTHER INFORMATION: wherein dA is conjugated to (Bz)-EO-compound 20

<400> SEQUENCE: 6
tttttttttt a                                                            11

<210> SEQ ID NO 7
<211> LENGTH: 11
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (11)...(11)
<223> OTHER INFORMATION: wherein dU is conjugated to EO-compound 10

<400> SEQUENCE: 7
tttttttttt u                                                            11

<210> SEQ ID NO 8
<211> LENGTH: 11
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (11)...(11)
<223> OTHER INFORMATION: wherein dA is conjugated to
      (Bz)-click-PEG-compound 32

<400> SEQUENCE: 8
tttttttttt a                                                            11

<210> SEQ ID NO 9
<211> LENGTH: 11
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (11)...(11)
<223> OTHER INFORMATION: wherein dU is conjugated to click-PEG-compound
      26

<400> SEQUENCE: 9
tttttttttt u                                                            11

<210> SEQ ID NO 10
<211> LENGTH: 11
<212> TYPE: DNA
```

```
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (11)...(11)
<223> OTHER INFORMATION: wherein dU is conjugated to PEG-compound 35

<400> SEQUENCE: 10
tttttttttt u                                                        11
```

FUNCTIONALIZED N-ACETYLGALACTOSAMINE NUCLEOSIDES

FIELD

The present application relates to N-acetylgalactosamine-conjugated nucleosides and their methods of preparation. The N-acetylgalactosamine-conjugated on-base nucleosides disclosed herein may be used for targeted in vivo delivery of oligonucleotide-based therapeutics.

REFERENCE TO SEQUENCE LISTING

The present application is being filed along with a Sequence Listing in electronic format. The Sequence Listing is provided as a file entitled SeqList_HGENE006A.txt created on Aug. 16, 2022, which is 3,430 bytes in size. The information in the electronic format of the Sequence Listing is incorporated herein by reference in its entirety.

BACKGROUND

Description of the Related Art

Oligonucleotide-based drugs have become a powerful epitome having ability to treat various diseases. N-acetylgalactosamine (GalNAc) is a well-defined liver-targeted moiety benefiting from its high affinity with asialoglycoprotein receptor (ASGPR). It can facilitate uptake and clearance of circulating GalNAc-conjugated oligo via clathrin-mediated endocytosis. The strongest attribute of GalNAc conjugates, compared to other oligo conjugates, is the internalization and cellular trafficking efficiency, which enables near-complete mRNA knockdown at exceedingly low doses in preclinical species and human subjects. This differentiating factor is related to the high membrane density of the ASGPR on hepatocytes and the rapid cycle in which it internalizes and recycles back to the cell surface. Only 15 mins are required for ASGPR internalization and recycling to the cell surface.

ASGPR consists of two homologous subunits, designated H1 and H2 in the human system, which form a non-covalent heterooligomeric complex with estimated ratios of 2:1 and 5:1, respectively. Both subunits are single-spanning membrane proteins with a calcium-dependent Gal/GalNAc recognition domain (CRDs). On the native receptor on the hepatocyte surface these binding sites are 25-30 Å apart. All conjugations of mono-, di-, tri-, or tetra-GalNAc sugars can enhance the delivery efficiency of oligonucleotides to hepatocytes.

GalNAc conjugation at the 2' and 3' positions of ribose have been previously reported. Oligonucleotide therapeutics have pharmacological challenges including susceptibility to nuclease-mediated degradation, rapid elimination, poor biodistribution, insufficient membrane permeability, immune stimulation, and potentially significant off-target effects. To overcome these pharmacological challenges, chemical modification to the ribose sugar is often necessary. However, the location of GalNAc on 2' and/or 3' positions could limit the application of these strategies on modified nucleosides, such as 2'-F, 2'-OMe, 2'-MOE nucleosides, all of which are commonly used sugar modifications. Using GalNAc-conjugated on-base nucleosides could address known stability and delivery problems for GalNAc-conjugated nucleosides, particularly when these nucleosides are internal in or at the ends of the sense strand. Accordingly, a need exists for preparing novel GalNAc-conjugated nucleosides, especially those with modified ribose at 2' and/or 3' position and other constrained ribose structures.

SUMMARY

In some embodiments, provided herein are compounds of Formula (I):

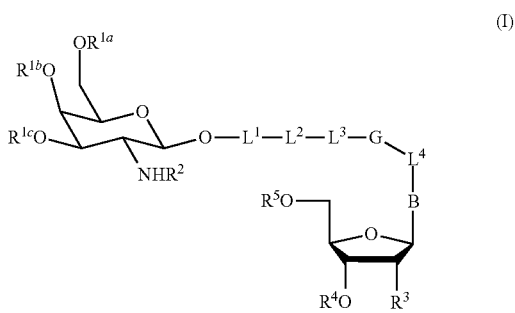

or a pharmaceutically acceptable salt thereof;
wherein each of $R^{1a}$, $R^{1b}$ and $R^{1c}$ is dependently hydrogen, benzyl (Bn), or —C(=O)$R^{1A}$;
$R^2$ is —C(=O)$C_{1-6}$ alkyl, —C(=O)$C_{1-6}$ haloalkyl, or —C(=O)phenyl;
$R^3$ is hydrogen, halo, hydroxy, $C_{1-6}$ alkoxy, $C_{1-6}$ haloalkoxy, $C_{1-6}$ alkyl, $C_{1-6}$ haloalkyl, ($C_{1-6}$ alkoxy)$C_{1-6}$ alkyl, —O—($C_{1-6}$ alkoxy)$C_{1-6}$ alkyl, or a hydroxy protecting group;
$R^4$ is hydrogen, a phosphoramidite moiety, —C(=O)CH$_2$CH$_2$C(=O)$R^{4A}$, or —P(O$R^{4B}$)N$R^{4C}R^{4D}$;
$R^5$ is a hydroxy protecting group;
each of $L^1$, $L^2$, and $L^3$ is independently a bond, —C(=O)—, —C(=S)—, —S(=O)$_2$—, —C(=O)N$R^6$—, —C(=S)N$R^6$—, —C(=O)O—, —C(=S)O—, —N$R^6$C(=O)N$R^6$—, —N$R^6$C(=S)N$R^6$—, —OP(=O)(OH)O—, —OP(=S)(OH)O—, —O—, —S—, —N$R^6$, optionally substituted $C_{1-10}$ alkylene, optionally substituted $C_{6-10}$ arylene, optionally substituted $C_{3-10}$ cycloalkylene, optionally substituted 5-10 membered hetetroarylene, optionally substituted 5 to 10 membered heterocyclylene, or optionally substituted 2 to 15 membered heteroalkylene wherein one or more carbon atoms are replaced with C(=O), O, S or N, provided that at least one of $L^1$, $L^2$, and $L^3$ is not a bond;
G is

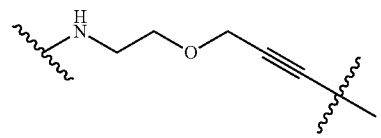 [SMILES: *C#CCOCCN*]

or triazolene optionally substituted with $R^7$;
$L^4$ is a bond, optionally substituted $C_{1-10}$ alkylene, or optionally substituted 2 to 15 membered heteroalkylene wherein one or more carbon atoms are replaced with C(=O), O, S or N;
B is a natural nucleobase, a modified natural nucleobase, or an unnatural nucleobase;

each $R^{1A}$ is independently $C_{1-6}$ alkyl, $C_{1-6}$ haloalkyl, or optionally substituted phenyl;

$R^{4A}$ is —OH, —OR$^8$ or —NR$^9$R$^{10}$;

each of $R^{4B}$, $R^{4C}$ and $R^{4D}$ is independently H, $C_{1-6}$ haloalkyl, or optionally substituted $C_{1-6}$ alkyl;

each $R^6$ is independently H or optionally substituted $C_{1-6}$ alkyl;

$R^7$ is independently halo, amino, hydroxy, $C_{1-6}$ alkyl, $C_{1-6}$ haloalkyl, $C_{1-6}$ alkoxy, $C_{1-6}$ haloalkoxy, ($C_{1-6}$ alkoxy) $C_{1-6}$ alkyl, or —O—($C_{1-6}$ alkoxy)$C_{1-6}$ alkyl;

$R^8$ is optionally substituted $C_{1-6}$ alkyl or a hydroxy protecting group; and each of $R^9$ and $R^{10}$ is independently H, optionally substituted $C_{1-6}$ alkyl or an amino protecting group.

In some embodiments, the compounds provided herein may have the structure of Formula (Ia):

(Ia)

or a pharmaceutically acceptable salt thereof.

In some embodiments, the compounds provided herein may have the structure of

Formula (Ib):

(Ib)

or a pharmaceutically acceptable salt thereof.

In some embodiments of the compound of Formula (I), (Ia) or (Ib), B may be:

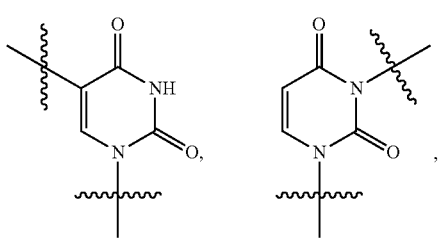

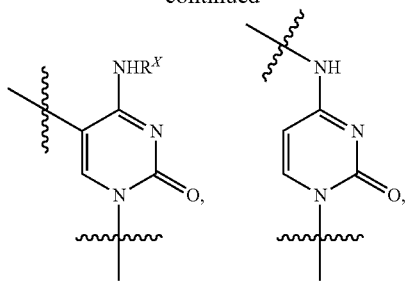

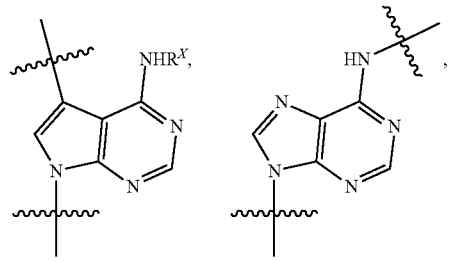

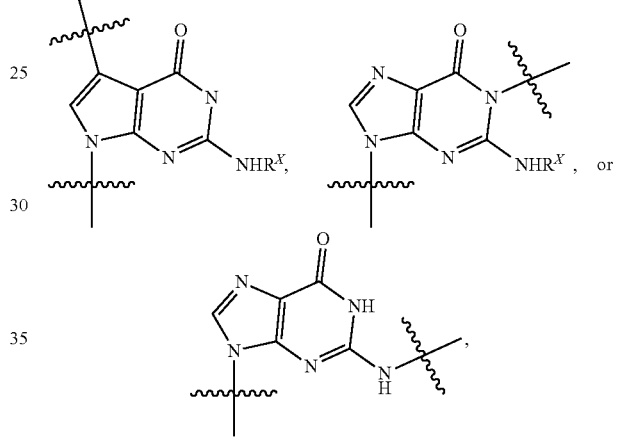, or

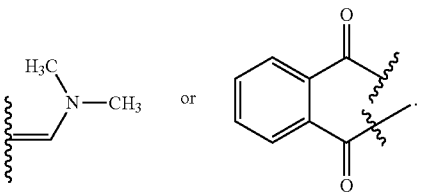

wherein $R^x$ is hydrogen or an amino protecting group, or $R^x$ and the hydrogen attached to the nitrogen atom form an amino protecting group. In some embodiments, $R^x$ may be —C(=O)$C_{1-6}$ alkyl or —C(=O)-phenyl. In some embodiments, the hydrogen in -NHR$^x$ is absent, and $R^x$ is dimethylformamidine

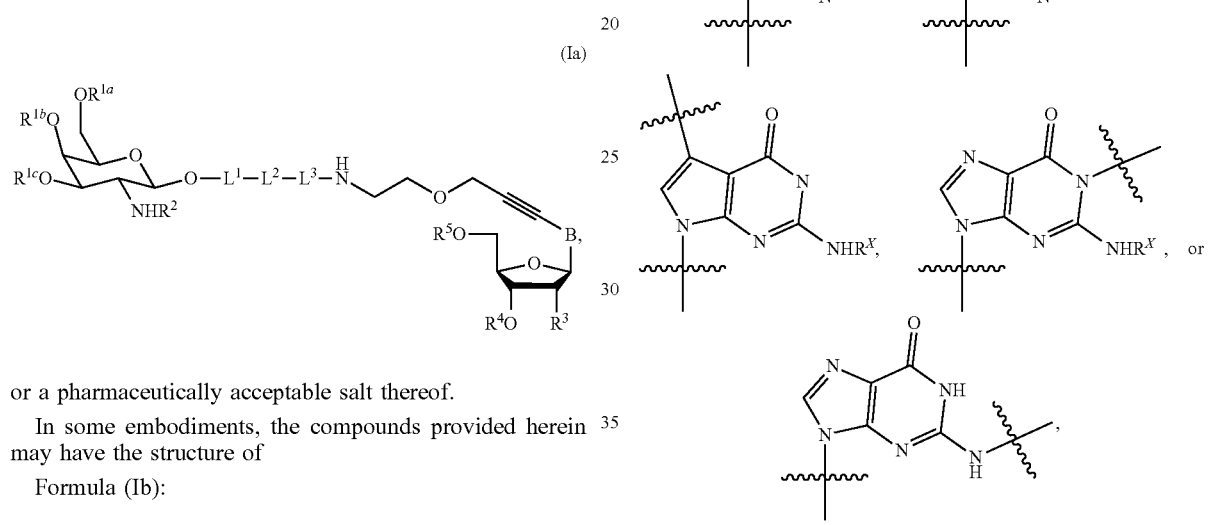

In some embodiments, $R^x$ may be —C(=O)CH$_3$ (Ac) or —C(=O)CH(CH$_3$)$_2$ (iBu).

In some embodiments of the compound of Formula (I), (Ia) or (Ib), each of $R^{1a}$, $R^{1b}$ and $R^{1c}$ may independently be H, —C(=O)CH$_3$ (Ac) or —C(=O)Ph (Bz). In some embodiments, $R^{1a}$, $R^{1b}$ and $R^{1c}$ may each be —C(=O)CH$_3$. In some embodiments, $R^2$ may be —C(=O)CH$_3$ or —C(=O)CF$_3$. In some embodiments, $R^3$ may be H, —OH, —OCH$_3$, —F, —OCF$_3$, —OCH$_2$CH$_2$OCH$_3$, —O-tert-butyldimethylsilyl, or —O-tri-isopropylsilyloxymethyl. In some embodiments, $R^4$ may be —C(=O)CH$_2$CH$_2$C(=O)OH. In other embodiments, $R^4$ may be

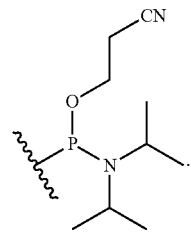 [SMILES: *P(OCCC#N)N(C(C)C)C(C)C]

In some embodiments, $R^5$ may a trityl type of hydroxy protecting group selected from (4-methoxyphenyl)diphenylmethyl, bis(4-methoxyphenyl)phenylmethyl, tris(4-methoxyphenyl)methyl, 9-phenylxanthen-9-yl or 9-(4-methoxyphenyl)xanthen-9-yl.

In some embodiments of the compound of Formula (I), (Ia) or (Ib), $L^1$ may be a bond, $C_{1-10}$ alkylene, or 2 to 15 membered heteroalkylene, wherein one or more carbon atoms are replaced with C(=O), O or N. In some embodiments, $L^2$ may be —C(=O)—, —C(=O)NR$^6$—, —NR$^6$—, or 2 to 15 membered heteroalkylene, wherein one or more carbon atoms are replaced with C(=O), O or N. In some embodiments, $R^6$ may H or CH$_3$. In some embodiments, $L^3$ may be a bond or 2 to 15 membered heteroalkylene, wherein one or more carbon atoms are replaced with C(=O), O or N. In some embodiments, $L^1$-$L^2$-$L^3$ may be —(CH$_2$)$_{2-6}$C(=O)— (e.g., —(CH$_2$)$_4$C(=O)—). In some other embodiments, $L^1$-$L^2$-$L^3$ may be —[(CH$_2$)$_2$O]$_{1-5}$—CH$_2$C(=O)— (e.g., —[(CH$_2$)$_2$O]$_2$—CH$_2$C(=O)—). In some other embodiments, $L^2$-$L^2$-$L^3$ may be —[(CH$_2$)$_2$O ]$_{1-5}$(CH$_2$)$_{1-4}$— (e.g., —[(CH$_2$)$_2$O]$_2$(CH$_2$)$_2$—). In some embodiments, $L^4$ may be a bond or $C_{1-10}$ alkylene.

In some embodiments of the compound of Formula (I), (Ia) or (Ib), the compound selected from the group consisting of:

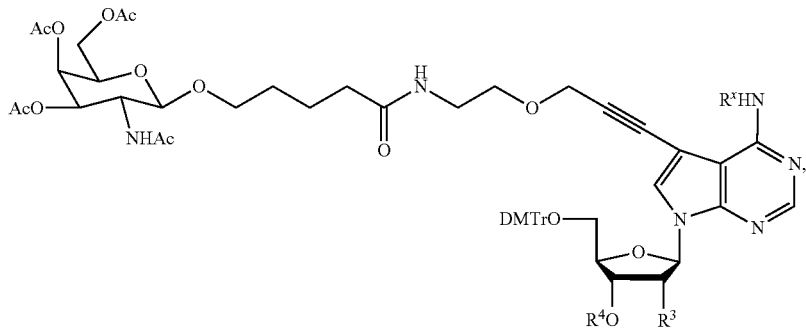

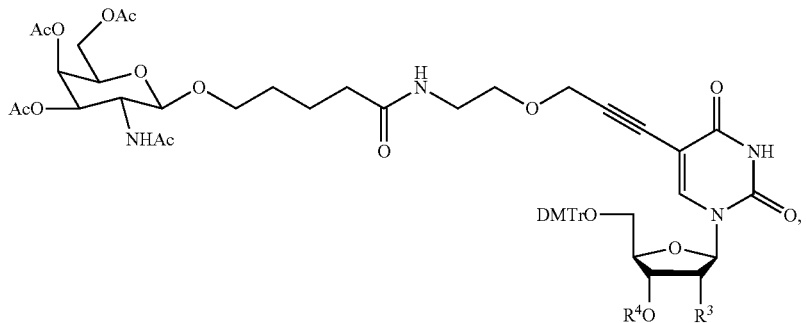

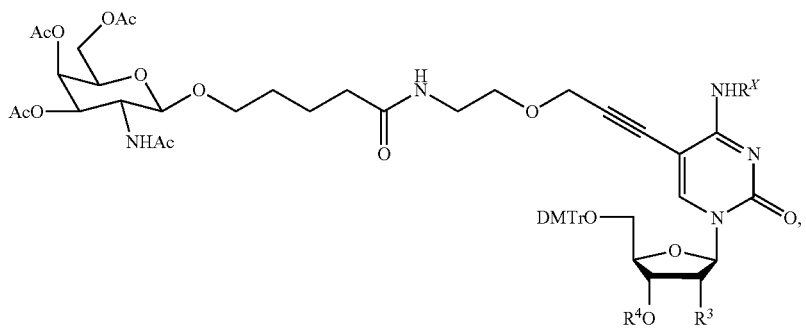

-continued
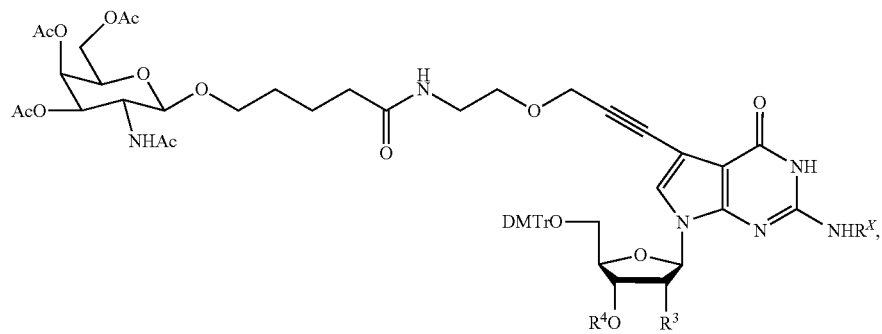
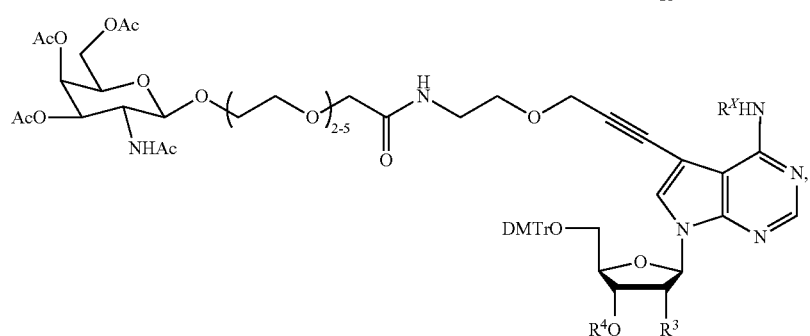
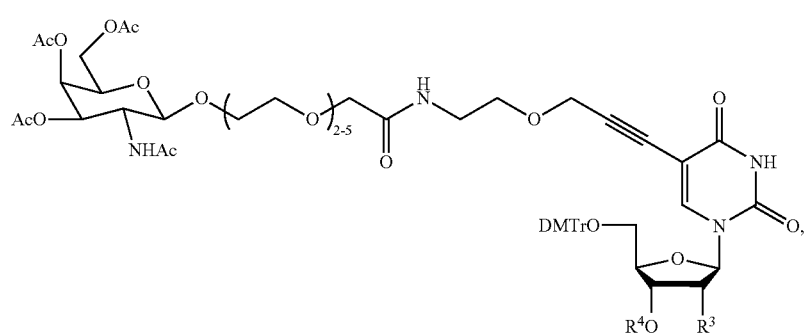
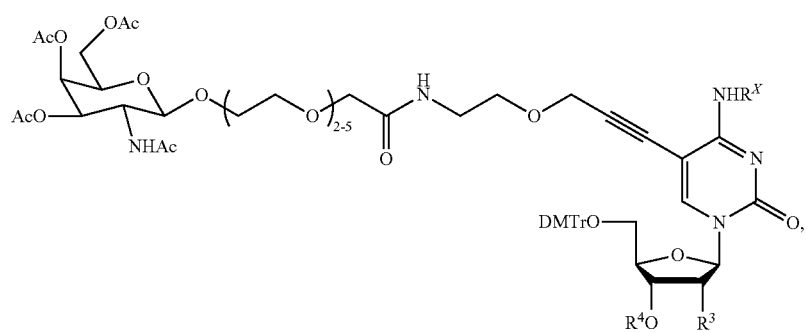
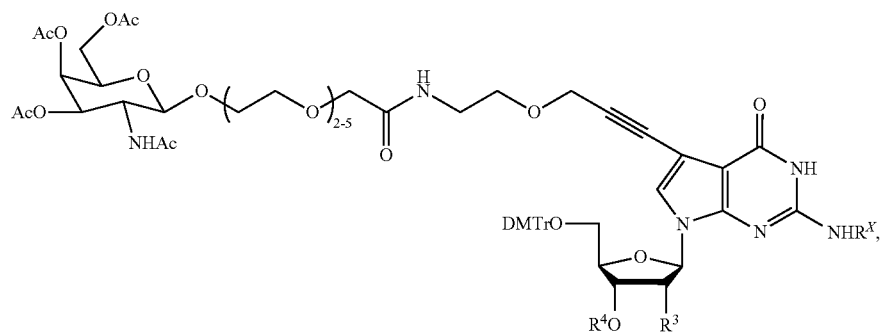

-continued

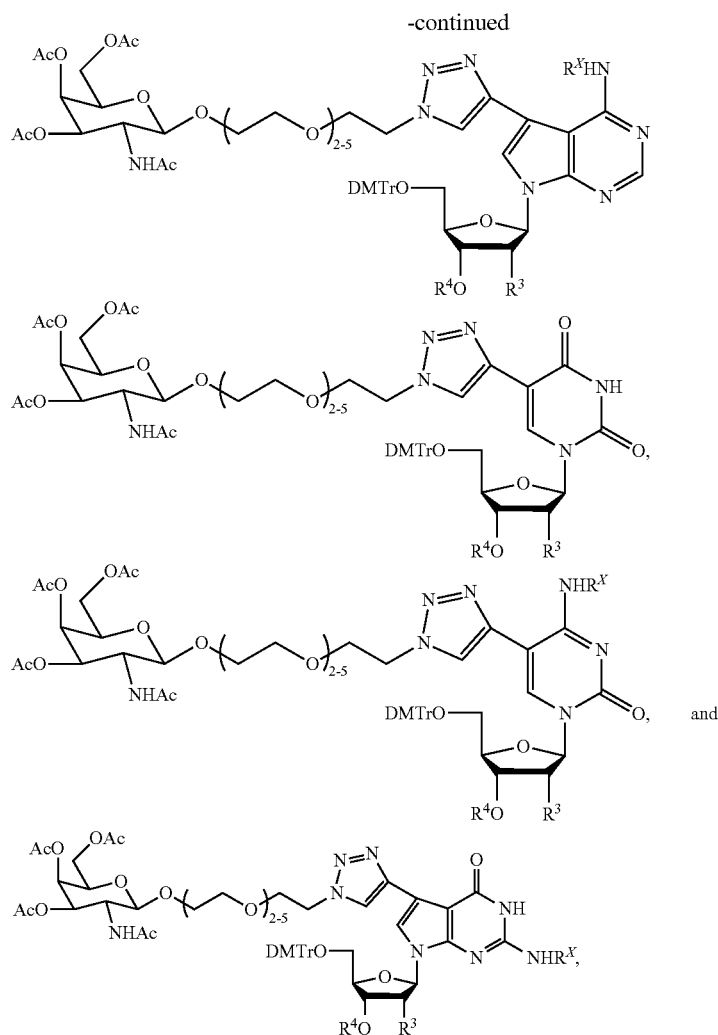

and pharmaceutically acceptable salts thereof;
wherein $R^3$ is H, halo, hydroxy, $C_{1-6}$ alkoxy, $C_{1-6}$ haloalkoxy, $C_{1-6}$ alkyl, $C_{1-6}$ haloalkyl, ($C_{1-6}$ alkoxy)$C_{1-6}$ alkyl, —O—($C_{1-6}$ alkoxy)$C_{1-6}$ alkyl, or a hydroxy protecting group;
each $R^x$ is independently H, —C(=O)CH$_3$, —C(=O)Ph, or —C(=O)CH(CH$_3$)$_2$; and
$R^4$ is —C(=O)CH$_2$CH$_2$C(=O)OH or

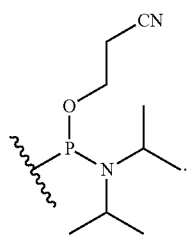 [SMILES: *P(OCCC#N)N(C(C)C)C(C)C]

In further embodiments, $R^3$ is H, —F, —OCH$_3$, —OCH$_2$CH$_2$OCH$_3$, or —O-tertbutyldimethylsilyl.

Another aspect of the present disclosure relates to a solid support comprising the nucleoside compound of Formula (I), (Ia) or (Ib) as described herein covalently attached thereto, for example, via $R^4$ of the compound. In one embodiment, $R^4$ is —C(=O)CH$_2$CH$_2$C(=O)OH. In further embodiments, the compound is covalently attached via a moiety

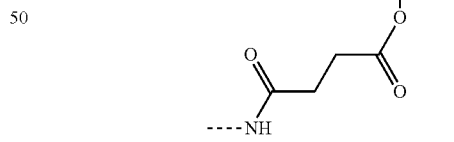

wherein the dashed line refers to the connection with the solid support, optionally through an additional linker, and wherein the squiggly line refers to the point of the attachment of the 3' oxygen of the compound to the remaining of the compound. In further embodiments, the solid support comprises an oligonucleotide, and the compound is incorporated into the oligonucleotide sequence.

In another aspect of the present disclosure, disclosed herein is a method of preparing a synthetic oligonucleotide, comprising reacting a compound described herein with an oligonucleotide. In some embodiments, the oligonucleotide may have a 1 to 100 nucleobase lengths. In some embodiments, the reaction may be conducted on a solid support.

DETAILED DESCRIPTION

Figure 1:
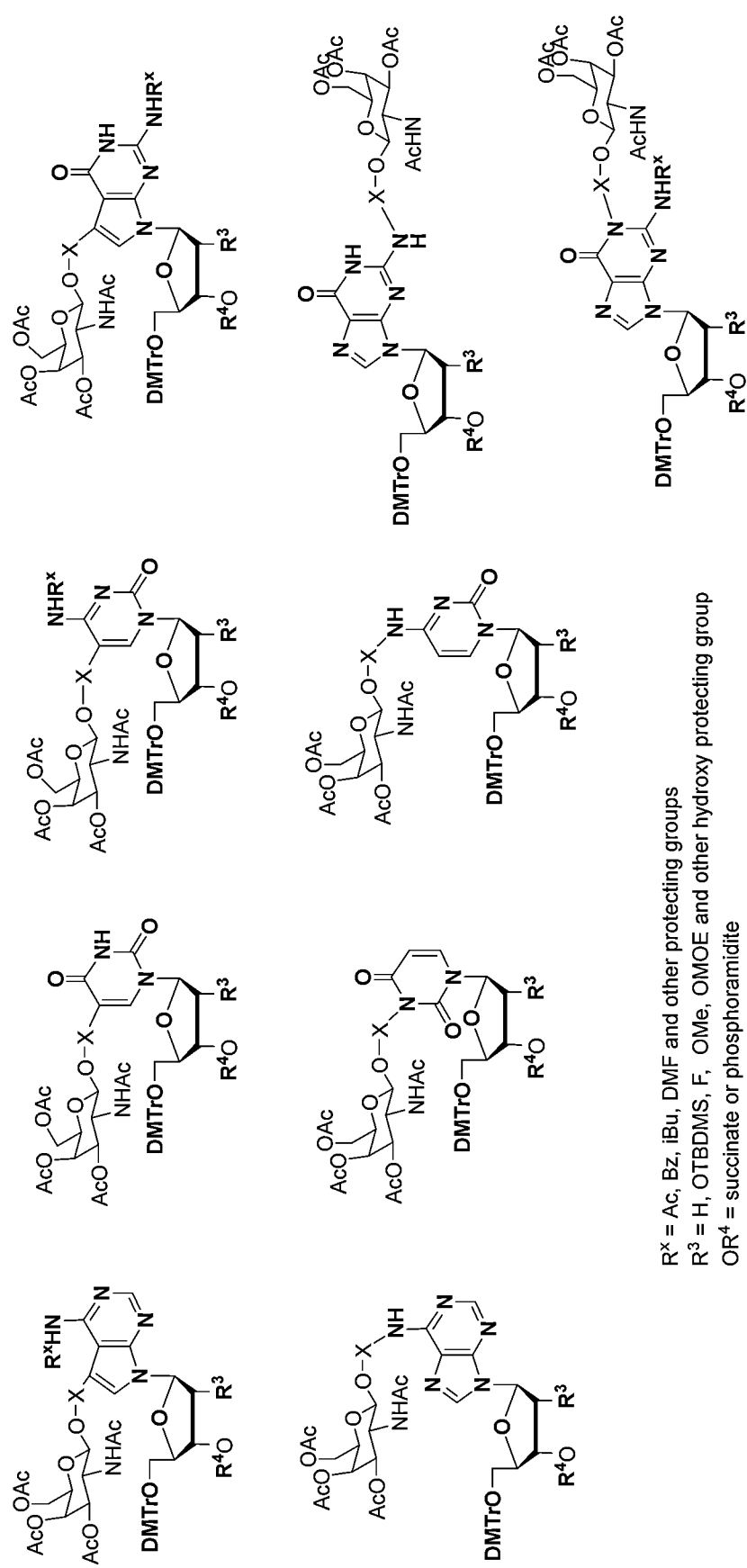
FIG. 1 illustrates a variety of monoantennary GalNAc-conjugated nucleosides according to an embodiment of the present application.
Figure 2:
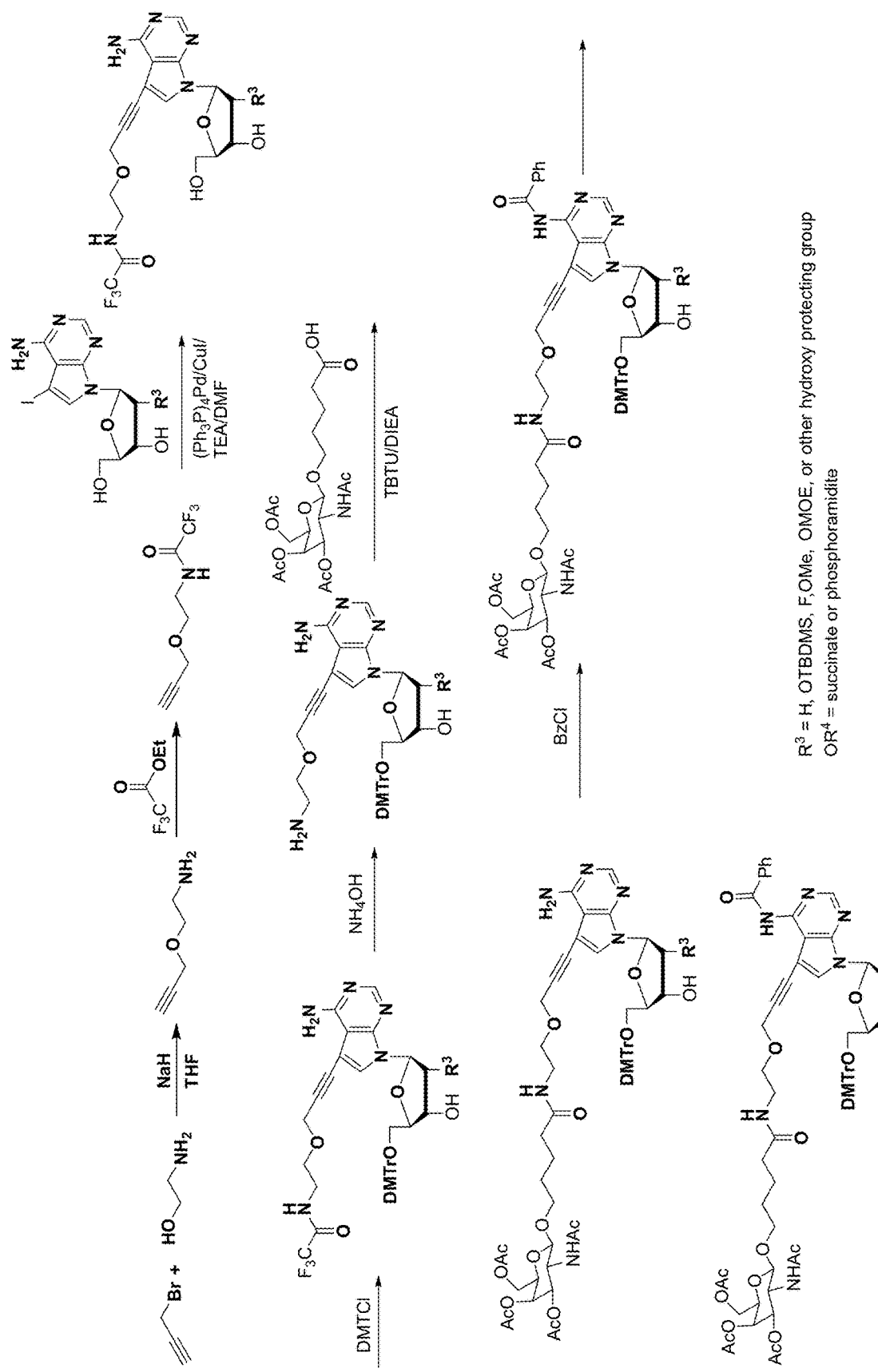
FIG. 2 is a reaction scheme for the conjugation of GalNAc with 7-deaza adenosine followed by subsequent formation of an —O-succinate (—O—C(=O)CH$_2$CH$_2$C(=O)OH) or —O-phosphoramidite at the 3'-position according to an embodiment of the present application.
Figure 3:
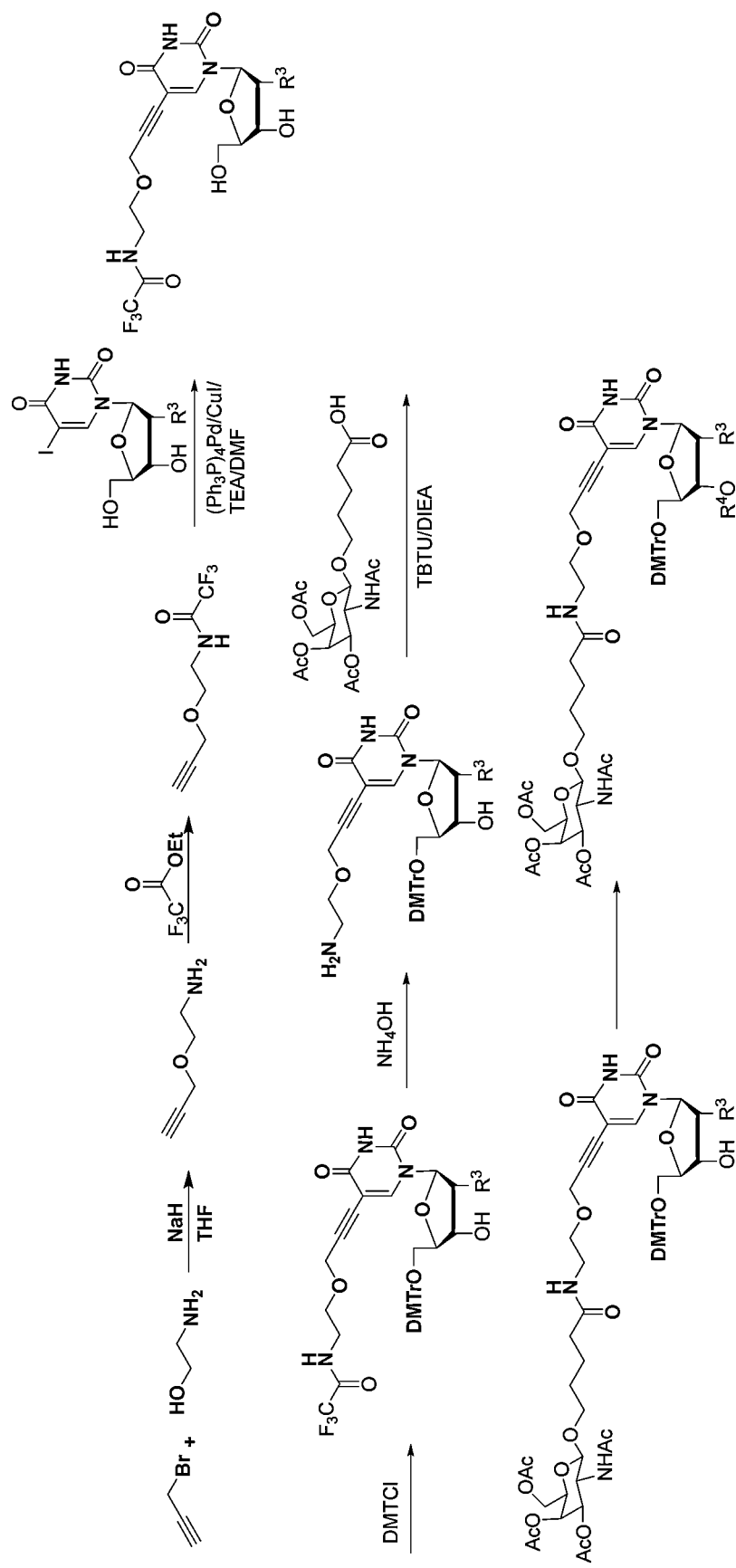
FIG. 3 is a reaction scheme for the conjugation of GalNAc with uridine followed by subsequent formation of an —O-succinate or —O-phosphoramidite at the 3'-position according to an embodiment of the present application.

The compounds disclosed herein relate to novel nucleosides with GalNAc conjugated to the nucleobase to provide novel methods for oligonucleotide delivery. In some embodiments, the GalNAc conjugated nucleosides compounds disclosed herein may contain a phosphoramidite moiety at the 3' position of the ribose or 2' deoxyribose that allows for the incorporation of the GalNAc conjugated nucleosides to the 5' end or any internal position of an oligonucleotide. In some other embodiments, the GalNAc conjugated nucleosides compounds disclosed herein may contain a succinate moiety at the 3' position of the ribose or 2' deoxyribose that allows for the incorporation of the GalNAc nucleoside on a solid support, which can introduce GalNAc conjugated nucleosides described herein to the 3' end of oligonucleotide.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting.

While the disclosure has been illustrated and described in detail in the foregoing description, such description is to be considered illustrative or exemplary and not restrictive. The disclosure is not limited to the disclosed embodiments. Variations to the disclosed embodiments can be understood and effected by those skilled in the art in practicing the claimed disclosure, from a study of the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

As used herein, any "R" group(s) represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^a$ and $R^b$, and the atom to which it is attached, are indicated to be "taken together" or "joined together" it means that they are covalently bonded to one another to form a ring:

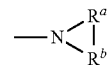

Whenever a group is described as being "optionally substituted" that group may be unsubstituted or substituted with one or more of the indicated substituents. Likewise, when a group is described as being "substituted", the substituent may be selected from one or more of the indicated substituents. If no substituents are indicated, it is meant that the indicated "optionally substituted" or "substituted" group may be one or more group(s) individually and independently selected from alkyl (e.g., $C_1$-$C_6$ alkyl); alkenyl (e.g., $C_2$-$C_6$ alkenyl); alkynyl (e.g., $C_2$-$C_6$ alkynyl); $C_3$-$C_8$ carbocyclyl (for example, $C_3$-$C_8$ cycloalkyl, $C_3$-$C_8$ cycloalkenyl, or $C_3$-$C_8$ cyclalkynyl, each may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); ($C_3$-$C_7$ carbocyclyl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); 5-10 membered heterocyclyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (5-10 membered heterocyclyl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); aryl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (aryl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); 5-10 membered heteroaryl (may further be optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy) $C_1$-$C_6$ alkyl, or —O($C_1$-$C_6$ alkoxy)$C_1$-$C_6$ alkyl); (5-10 membered heteroaryl)$C_1$-$C_6$ alkyl (may further be optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); halo (e.g., fluoro, chloro, bromo, iodo); cyano; hydroxy; protected hydroxy; alkoxy (e.g., $C_1$-$C_6$ alkoxy); haloalkyl (e.g., $C_1$-$C_6$ haloalkyl, such as —$CF_3$); haloalkyl (e.g., $C_1$-$C_6$ haloalkoxy such as —$OCF_3$); ($C_1$-$C_6$ alkoxy)$C_1$-$C_6$ alkyl; —O($C_1$-$C_6$ alkoxy) $C_1$-$C_6$ alkyl; ($C_1$-$C_6$ haloalkoxy)$C_1$-$C_6$ alkyl; —O($C_1$-$C_6$ haloalkoxy)$C_1$-$C_6$ alkyl; aryloxy; sulfhydryl (mercapto); alkylthio (e.g., $C_1$-$C_6$ alkylthio); arylthio; azido; nitro; O-carbamyl ; N-carbamyl; O-thiocarbamyl; N-thiocarbamyl; C-amido; N-amido; S-sulfonamido; N-sulfonamido; C-carboxy; protected C-carboxy; O-carboxy; acyl; cyanate; isocyanato; thiocyanato; isothiocyanato; silyl; sulfenyl; sulfinyl; sulfonyl; trihalomethanesulfonyl; trihalomethanesulfonamido; amino (including protected derivatives thereof); mono-substituted amino (for example, NH($C_1$-$C_6$ alkyl); di-substituted amino (for example, N($C_1$-$C_6$ alkyl)$_2$); oxo (=O); and thioxo (=S).

As used herein, "$C_a$ to $C_b$" in which "a" and "b" are integers refer to the number of carbon atoms in an alkyl group, or the number of ring atoms of a cycloalkyl, aryl, heteroaryl or heterocyclyl group. That is, the alkyl, ring of the cycloalkyl, and ring of the aryl, can contain from "a" to "b", inclusive, carbon atoms. Likewise, the ring of the heteroaryl and ring of the heterocyclyl can contain from "a" to "b", inclusive, total ring atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, ($CH_3$)$_2$CH—, $CH_3CH_2CH_2CH_2$—, $CH_3CH_2CH(CH_3)$— and ($CH_3$)$_3$C—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, cycloalkyl, aryl, heteroaryl or heterocyclyl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_3$-$C_8$ carbocyclyl or cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, n-propyl, isopropyl, butyl, isobutyl, tertiary butyl, pentyl (straight chain or branched), and hexyl (straight chain or branched). The alkyl group may be substituted or unsubstituted.

As used herein, "alkenyl" refers to a straight or branched hydrocarbon chain containing one or more double bonds. The alkenyl group may have 2 to 20 carbon atoms. By way of example only, "$C_2$-$C_6$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like. The alkenyl group may be substituted or unsubstituted.

As used herein, "alkynyl" refers to a straight or branched hydrocarbon chain containing one or more triple bonds. The alkynyl group may have 2 to 20 carbon atoms. By way of example only, "$C_2$-$C_4$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like. The alkynyl group may be substituted or unsubstituted.

As used herein, "cycloalkyl" refers to a completely saturated (no double or triple bonds) mono- or multi- cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 10 atoms in the ring(s), 3 to 8 atoms in the ring(s), or 3 to 6 atoms in the ring(s). A cycloalkyl group may be unsubstituted or substituted. Examples of monocyclic cycloalkyl groups include, but are in no way limited to, cyclopropyl, cyclobutyl, cyclopentyl, cyclohexyl, cycloheptyl and cyclooctyl. Examples of bicyclic fused cycloalkyl groups are decahydronaphthalenyl, dodecahydro-1H-phenalenyl and tetradecahydroanthracenyl; examples of bicyclic bridged cycloalkyl groups are bicyclo[1.1.1]pentyl, adamantanyl and norbornanyl; and examples of bicyclic spiro cycloalkyl groups include spiro [3.3]heptane and spiro [4.5] decane.

As used herein, "carbocyclyl" refers to a non-aromatic a mono- or multi- cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Examples of carbocyclyl groups include, but are in no way limited to, cycloalkyl groups, as defined herein, and the non-aromatic portions of 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$ aryl group, or a $C_{10}$ aryl group. Examples of aryl groups include, but are not limited to, benzene and naphthalene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 5 to 10 atoms in the ring(s), 6 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to three-, four-, five-, six-, seven-, eight-, nine-, and ten-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., heterocyclyl groups are not aromatic). The heteroatom(s) is an element other than carbon including, but not limited to, oxygen, sulfur and nitrogen. A heterocycle may further contain one or more carbonyl functionalities, so as to make the definition include oxo-systems such as lactams, lactones, and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" refers to compounds wherein the heterocyclyl contains a linkage of one or more atoms connecting non-adjacent atoms. As used herein, the term "spiro" refers to two rings which have one atom in common and the two rings are not linked by a bridge. Heterocyclyl groups can contain 3 to 10 atoms in the ring(s), 3 to 8 atoms in the ring(s), 3 to 6 atoms in the ring(s), or 5 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogen in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include but are not limited to, aziridine, oxirane, thiirane, azetidine, oxetane, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "alkylene" refers to a branched, or straight chain fully saturated di-radical chemical group containing only carbon and hydrogen that is attached to the rest of the molecule via two points of attachment. By way of example only, "$C_1$-$C_{10}$ alkylene" indicates that there are one to ten carbon atoms in the alkylene chain. Non-limiting examples include ethylene (—CH$_2$CH$_2$—), propylene (—CH$_2$CH$_2$CH$_2$—), butylene (—CH$_2$CH$_2$CH$_2$CH$_2$—), and pentylene (—CH$_2$CH$_2$CH$_2$CH$_2$CH$_2$—).

As used herein, "alkenylene" refers to a straight or branched chain di-radical chemical group containing only carbon and hydrogen and containing at least one carbon-carbon double bond that is attached to the rest of the molecule via two points of attachment. The alkenylene group may be designated as "$C_2$-$C_{10}$ alkenylene" or similar designations. By way of example only, "$C_2$-$C_{10}$ alkenylene" indicates that there are two to ten carbon atoms in the alkenylene chain.

As used herein, "alkynylene" refers to a straight or branched chain di-radical chemical group containing only carbon and hydrogen and containing at least one carbon-carbon triple bond that is attached to the rest of the molecule via two points of attachment. The alkynylene group may be designated as "$C_2C_{10}$ alkenylene" or similar designations. By way of example only, "$C_2$-$C_{10}$ alkynylene" indicates that there are two to ten carbon atoms in the alkynylene chain.

As used herein, "heteroalkylene" refers to an alkylene group, as defined herein, containing one or more heteroatoms in the carbon back bone (i.e., an alkylene group in which one or more carbon atoms is replaced with a heteroatom, for example, nitrogen atom, oxygen atom or sulfur atom). For example, a —$CH_2$— may be replaced with —O—, —S—, or —NH—. Heteroalkylene groups include, but are not limited to ether, thioether, amino-alkylene, and alkylene-amino-alkylene moieties. In some embodiments, the heteroalkylene may include one, two, three, four, or five —$CH_2CH_2O$—unit(s). Alternatively and/or additionally, one or more carbon atoms can also be substituted with an oxo (=O) to become a carbonyl. For example, a —$CH_2$— may be replaced with —C(=O)—.

As used herein, "aralkyl" and "(aryl)alkyl" refer to an aryl group, as defined above, connected, as a substituent, via an alkylene group, as described above. The alkylene and aryl group of an aralkyl may be substituted or unsubstituted. Examples include but are not limited to benzyl, 2-phenylalkyl, 3-phenylalkyl, and naphthylalkyl. In some embodiments, the alkylene is an unsubstituted straight chain containing 1, 2, 3, 4, 5, or 6 methylene unit(s).

As used herein, "heteroaralkyl" and "(heteroaryl)alkyl" refer to a heteroaryl group, as defined above, connected, as a substituent, via an alkylene group, as defined above. The alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs. In some embodiments, the alkylene is an unsubstituted straight chain containing 1, 2, 3, 4, 5, or 6 methylene unit(s).

As used herein, "(heterocyclyl)alkyl" refer to a heterocyclic or a heterocyclyl group, as defined above, connected, as a substituent, via an alkylene group, as defined above. The alkylene and heterocyclyl groups of a (heterocyclyl)alkyl may be substituted or unsubstituted. Examples include but are not limited to (tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl. In some embodiments, the alkylene is an unsubstituted straight chain containing 1, 2, 3, 4, 5, or 6 methylene unit(s).

As used herein, "cycloalkylalkyl" and "(cycloalkyl)alkyl" refer to a cycloalkyl group (as defined herein) connected, as a substituent, via an alkylene group. Examples include but are not limited to cyclopropylmethyl, cyclobutylmethyl, cyclopentylethyl, and cyclohexylpropyl. In some embodiments, the alkylene is an unsubstituted straight chain containing 1, 2, 3, 4, 5, or 6 methylene unit(s).

As used herein, "alkoxy" refers to the formula —OR wherein R is an alkyl group, as defined herein. A non-limiting list of alkoxy group includes methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "amino" refer to a —$NH_2$ group. The term "mono-substituted amino group" as used herein refers to an amino (—$NH_2$) group where one of the hydrogen atom is replaced by a substituent. The term "di-substituted amino group" as used herein refers to an amino (—$NH_2$) group where each of the two hydrogen atoms is replaced by a substituent. The term "optionally substituted amino," as used herein refer to a -$NR_AR_B$ group where $R_A$ and $R_B$ are independently hydrogen, alkyl, cycloalkyl, aryl, heteroaryl, heterocyclyl, aralkyl, or heterocyclyl(alkyl), as defined herein.

As used herein, "alkylamino" or "(alkyl)amino" refers to a -$NR_AR_B$ group where $R_A$ and $R_B$ are hydrogen or alkyl as defined above, and at least one of $R_A$ and $R_B$ is alkyl. The alkyl portion of the (alkyl)amine, includes, for example, $C_1$-$C_6$ alkyl groups.

As used herein, "aminoalkyl" or "(amino)alkyl" refers to an alkyl group in which one or more of the hydrogen atoms are replaced by an amino group or "-$NRAR_B$" group as defined herein. The alkyl portion of the aminoalkyl, includes, for example, $C_1$-$C_6$ alkyl.

The term "halogen atom" or "halogen" as used herein, means any one of the radio-stable atoms of column 7 of the Periodic Table of the Elements, such as, fluorine, chlorine, bromine, and iodine.

As used herein, "alkoxyalkyl" or "(alkoxy)alkyl" refers to an alkoxy group connected via an alkylene group, such as $C_2$-$C_8$ alkoxyalkyl, or ($C_1$-$C_6$ alkoxy)$C_1$-$C_6$ alkyl, for example, —$(CH_2)_{1-3}$—$OCH_3$.

As used herein, "—O-alkoxyalkyl" or "—O-(alkoxy)alkyl" refers to an alkoxy group connected via an —O-(alkylene) group, such as —O-($C_1$-$C_6$ alkoxy)$C_1$-$C_6$ alkyl, for example, —O-$(CH_2)_{1-3}$—$OCH_3$.

As used herein, "aryloxy" and "arylthio" refers to RO— and RS—, in which R is an aryl, as defined above, such as but not limited to phenyl. Both an aryloxy and arylthio may be substituted or unsubstituted.

A "sulfenyl" group refers to an "—SR" group in which R can be hydrogen, alkyl, alkenyl, alkynyl, carbocyclyl, aryl, heteroaryl, heterocyclyl, aralkyl, or heterocyclyl(alkyl), as defined above. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, carbocyclyl, aryl, heteroaryl, heterocyclyl, aralkyl, or heterocyclyl (alkyl), as defined herein. An O-carboxy may be substituted or unsubstituted.

The terms "ester" and "C-carboxy" refer to a "—C(=O)OR" group in which R can be the same as defined with respect to O-carboxy. An ester or C-carboxy may be substituted or unsubstituted.

A "trihalomethanesulfonyl" group refers to an "$X_3CSO_2$—" group wherein X is a halogen.

A "trihalomethanesulfonamido" group refers to an "X₃CS(O)₂N(R)—" group wherein X is a halogen and R is hydrogen, alkyl, alkenyl, alkynyl, carbocyclyl, aryl, heteroaryl, heterocyclyl, aralkyl, or heterocyclyl(alkyl), as defined herein.

A "mercapto" group refers to an "—SH" group.

An "S-sulfonamido" group refers to a "—SO₂N(R$_A$R$_B$)" group in which R$_A$ and R$_B$ can be independently hydrogen, alkyl, alkenyl, alkynyl, carbocyclyl, aryl, heteroaryl, heterocyclyl, aralkyl, or heterocyclyl(alkyl) as defined herein. An S-sulfonamido may be substituted or unsubstituted.

An "N-sulfonamido" group refers to a "RSO₂N(R$_A$)—" group in which R and R$_A$ can be independently hydrogen, alkyl, alkenyl, alkynyl, carbocyclyl, aryl, heteroaryl, heterocyclyl, aralkyl, or heterocyclyl(alkyl), as defined herein. An N-sulfonamido may be substituted or unsubstituted.

An "O-carbamyl" group refers to a "—OC(=O)N(R$_A$R$_B$)" group in which R$_A$ and R$_B$ can be the same as defined with respect to S-sulfonamido. An O-carbamyl may be substituted or unsubstituted.

An "N-carbamyl" group refers to an "ROC(=O)N(RA)—" group in which R and R$_A$ can be the same as defined with respect to N-sulfonamido. An N-carbamyl may be substituted or unsubstituted.

An "O-thiocarbamyl" group refers to a "—OC(=S)—N(R$_A$R$_B$)" group in which R$_A$ and R$_B$ can be the same as defined with respect to S-sulfonamido. An O-thiocarbamyl may be substituted or unsubstituted.

An "N-thiocarbamyl" group refers to an "ROC(=S)N(R$_A$)—" group in which R and R$_A$ can be the same as defined with respect to N-sulfonamido. An N-thiocarbamyl may be substituted or unsubstituted.

A "C-amido" group refers to a "—C(=O)N(R$_A$R$_B$)" group in which R$_A$ and R$_B$ can be the same as defined with respect to S-sulfonamido. A C-amido may be substituted or unsubstituted.

An "N-amido" group refers to a "RC(=O)N(R$_A$)—" group in which R and R$_A$ can be the same as defined with respect to N-sulfonamido. An N-amido may be substituted or unsubstituted.

Where the numbers of substituents are not specified (e.g., haloalkyl), there may be one or more substituents present. For example, "haloalkyl" may include one or more of the same or different halogens.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition, it is understood that in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns. Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as —AE— or

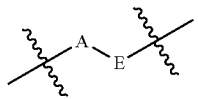

includes the substituent being oriented such that the A is attached at the leftmost attachment point of the molecule as well as the case in which A is attached at the rightmost attachment point of the molecule. In addition, if a group or substituent is depicted as

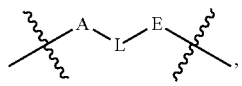

and when L is defined as a bond or absent; such group or substituent is equivalent to

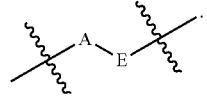

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms and nano-particulate forms.

Likewise, it is understood that the compounds described herein, such as compounds of preferred embodiments, include the compound in any of the forms described herein (e.g., pharmaceutically acceptable salts, crystalline forms, amorphous form, solvated forms, enantiomeric forms, tautomeric forms, and the like).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, Protective Groups in Organic Synthesis, 3. Ed. John Wiley & Sons, 1999, and in J.F.W. McOmie, Protective Groups in Organic Chemistry Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl (Bn); substituted benzyl; alkylcarbonyls (e.g., t-butoxycarbonyl (BOC), acetyl (i.e., —C(=O)CH$_3$ or Ac), or isobutyryl (iBu); arylalkylcarbonyls (e.g., benzyloxycarbonyl or benzoyl (i.e., —C(=O)Ph or Bz)); substituted methyl ether (e.g., methoxymethyl ether (MOM)); substituted ethyl ether (e.g., methoxyethyl ether (MOE); a substituted benzyl ether; tetrahydropyranyl ether; silyl ethers (e.g., trimethylsilyl (TMS), triethylsilyl, triisopropylsilyl, t-butyldimethylsilyl (TBDMS), tri-iso-propylsilyloxymethyl (TOM), or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

The term "leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in Organic Chemistry, 2d ed., Francis Carey (1992), pages 328-331; Introduction to Organic Chemistry, 2d ed., Andrew Streitwieser and Clayton Heathcock (1981), pages 169-171; and Organic Chemistry, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl)amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like. In some embodiments, the compounds described herein may be in the form of a trifluoroacetate salt.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof, such as deazapurine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, deazapurine, 7-deazapurine, adenine, 7-deaza adenine, guanine, 7-deaza guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, when an oligonucleotide is described as "comprising" or "incorporating" a nucleoside compound described herein, it means that the nucleoside described herein forms a covalent bond with the oligonucleotide. In some embodiments, the covalent bond is formed by the reaction of the 5' hydroxy group of the nucleoside of Formula (I) as described herein and the 3' phosphoramidite group of another nucleoside (which may be the terminal nucleoside of an oligonucleoside) to form a phosphodiester bond, or the reaction of the 3' phosphoramidite group of the nucleoside of Formula (I) as described herein with the 5' hydroxy group of another nucleoside (which may be the terminal nucleoside of an oligonucleoside) to form a phosphodiester bond or an equivalent thereof (e.g., thiophosphodiester).

As used herein, "derivative" or "analogue" means a synthetic nucleoside or nucleotide derivative having modified base moieties and/or modified sugar moieties. Such derivatives and analogs are discussed in, e.g., Scheit, Nucleotide Analogs (John Wiley & Son, 1980) and Uhlman et al., Chemical Reviews 90:543-584, 1990. Nucleotide analogs can also comprise modified phosphodiester linkages, including phosphorothioate, phosphorodithioate, alkyl-phosphonate, phosphoranilidate, phosphoramidite, and phosphoramidate linkages. "Derivative" and "analog" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

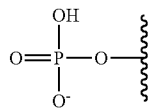 [SMILES: *OP(=O)([O-])O]

and)

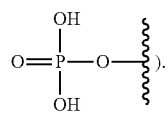

As used herein, the terms "monophosphate," "diphosphate," and "triphosphate" are used in their ordinary sense as understood by those skilled in the art, and include protonated forms.

Compounds of Formula (I)

Some embodiments provide a compound of Formula (I), or a pharmaceutically acceptable salt thereof as described herein:

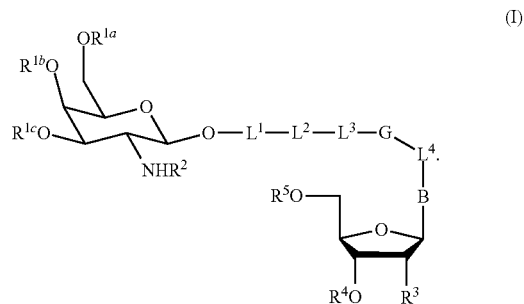

In some embodiments of the compounds of Formula (I), the compounds have the structure of Formula (Ia):

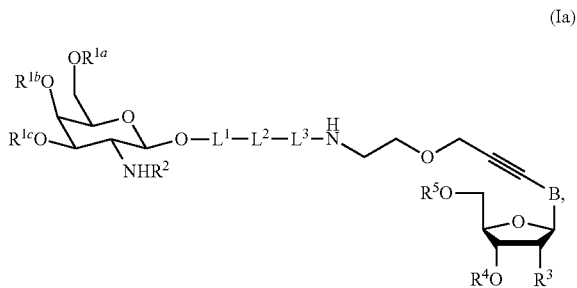

or a pharmaceutically acceptable salt thereof. In other embodiments, the compounds have the structure of Formula (Ib):

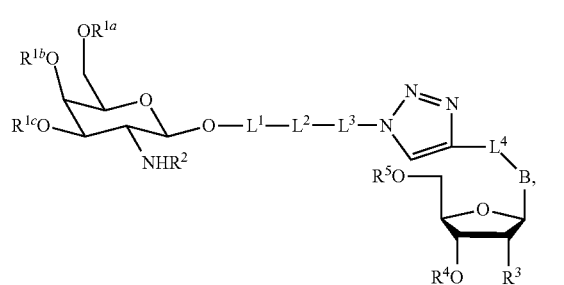

or a pharmaceutically acceptable salt thereof.

In some embodiments of the compounds of Formula (I), (Ia) or (Ib), each of $R^{1a}$, $R^{1b}$ and $R^{1c}$ is independently hydrogen, benzyl (Bn), or —C(=O)$R^{1d}$, wherein $R^{1d}$ is $C_{1-6}$ alkyl, $C_{1-6}$ haloalkyl, or optionally substituted phenyl. In some embodiments, $R^{1a}$ is C(=O)CH$_3$ (Ac). In some embodiments, $R^{1a}$ is C(=O)Ph (Bz). In some embodiments, $R^{1b}$ is C(=O)CH$_3$. In other embodiments, $R^{1b}$ is C(=O)Ph. In some embodiments, $R^{1c}$ is C(=O)CH$_3$. In other embodiments, $R^{1c}$ is C(=O)Ph. In some embodiments, each of $R^{1a}$, $R^{1b}$, and $R^{1c}$ is C(=O)CH$_3$. In some other embodiments, each of $R^{1a}$, $R^{1b}$, and $R^{1c}$ is H. In some other embodiments, each of $R^{1a}$, $R^{1b}$, and $R^{1c}$ is C(=O)Ph.

In some embodiments of the compounds of Formula (I), (Ia) or (Ib), $R^2$ is —C(=O)$C_{1-6}$ alkyl. In other embodiments, $R^2$ is —C(=O)$C_{1-6}$ haloalkyl. In one embodiment, $R^2$ is —C(=O)$CH_3$. In another embodiment, $R^2$ is —C(=O)$CF_3$.

In some embodiments of the compounds of Formula (I), (Ia) or (Ib), $R^3$ is hydrogen, halo, hydroxy, $C_{1-6}$ alkoxy, $C_{1-6}$ haloalkoxy, $C_{1-6}$ alkyl, $C_{1-6}$ haloalkyl, ($C_{1-6\ alkoxy}$)$C_{1-6}$ alkyl, —O—($C_{1-6}$ alkoxy)$C_{1-6}$ alkyl, or a hydroxy protecting group. In some embodiments, $R^3$ is H. In other embodiments, $R^3$ is —OH. In yet other embodiments, $R^3$ is —OCH$_3$. In still yet other embodiments, $R^3$ is —F. In some embodiments, $R^3$ is —OCF$_3$. In some embodiments, $R^3$ is a hydroxy protecting group. In one embodiment, $R^3$ is —OCH$_2$CH$_2$OCH$_3$ (—O—MOE). In another embodiment, $R^3$ is —O-tertbutyldimethylsilyl (—O—TBDMS). In one embodiment, $R^3$ is —O-tri-isopropylsilyloxymethyl (—O—TOM).

In some embodiments of the compounds of Formula (I), (Ia) or (Ib), $R^4$ is hydrogen. In other embodiments, $R^4$ is a phosphoramidite moiety. In yet other embodiments, $R^4$ is —C(=O)CH$_2$CH$_2$C(=O)$R^{4A}$, wherein $R^{4A}$ is —OH, —OR$^8$ or —NR$^9$R$^{10}$. In some embodiments, each of $R^9$ and $R^{10}$ is independently H, optionally substituted $C_{1-6}$ alkyl or an amino protecting group. In other embodiments, $R^4$ is —P(OR$^{4B}$)NR$^{4C}$R$^{4D}$, wherein each of $R^{4B}$, $R^{4C}$ and $R^{4D}$ is independently H, $C_{1-6}$ haloalkyl, or optionally substituted $C_{1-6}$ alkyl. In one embodimentcc, $R^4$ is —C(=O)CH$_2$CH$_2$C(=O)OH. In another embodiment, $R^4$ is

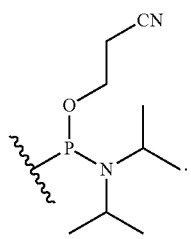 [SMILES: *P(OCCC#N)N(C(C)C)C(C)C]

In some embodiments of the compounds of Formula (I), (Ia) or (Ib), $R^5$ is a trityl type hydroxy protecting group. In some embodiments, $R^5$ is (4-methoxyphenyl)diphenylmethyl (i.e., monomethoxytrityl (MMTr)). In other embodiments, $R^5$ is bis(4-methoxyphenyl)phenylmethyl (i.e., 4,4'-dimethoxytrityl (DMTr)). In yet other embodiments, $R^5$ is tris(4-methoxyphenyl)methyl (i.e., 4,4',4''-trimethoxytrityl (TMTr)). In some embodiments, $R^5$ is 9-phenylxanthen-9-yl. In other embodiments, $R^5$ is 9-(4-methoxyphenyl)xanthen-9-yl.

In some embodiments of the compounds of Formula (I), G is

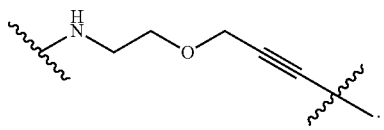 [SMILES: *C#CCOCCN*]

In other embodiments, G is triazolene optionally substituted with $R^7$. In some embodiments, $R^7$ is halo or $C_1$-$C_6$ alkyl. In one embodiment, $R^7$ is methyl.

In some embodiments of the compounds of Formula (I), (Ia) or (Ib), B is a natural nucleobase. In other embodiments, B is a modified natural nucleobase. In yet other embodiments, B is an unnatural nucleobase. In some embodiments, B is

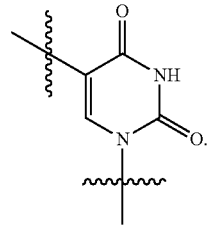 [SMILES: *c1cn(*)c(=O)[nH]c1=O]

In other embodiments, B is

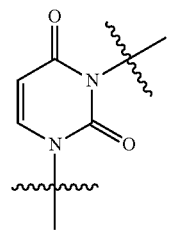

In other embodiments, B is

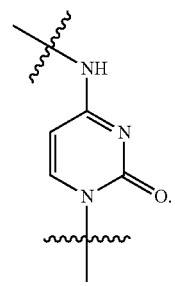 [SMILES: *Nc1ccn(*)c(=O)n1]

In yet other embodiments, B is.

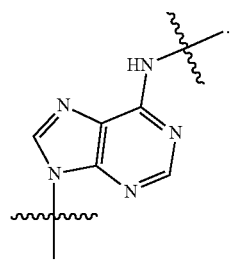 [SMILES: *Nc1ncnc2c1ncn2*]

In still yet other embodiments, B is

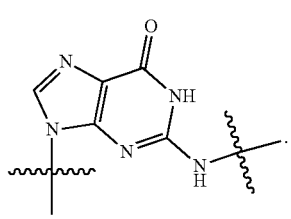 [SMILES: *Nc1nc2c(ncn2*)c(=O)[nH]1]

In some embodiments, B is

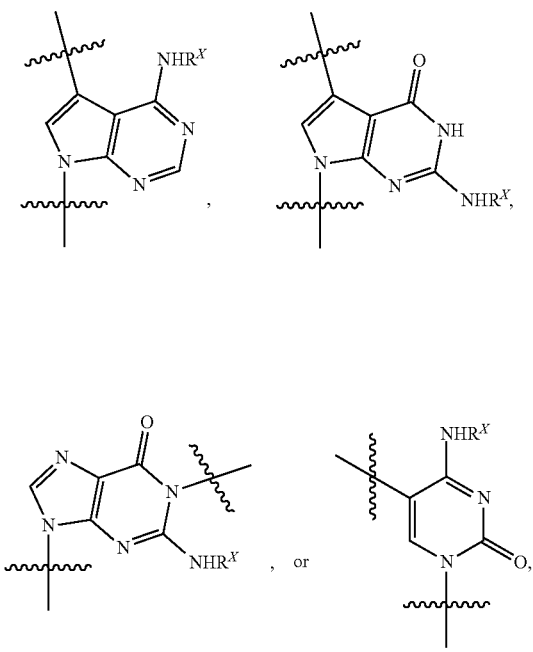

wherein $R^x$ is hydrogen or an amino protecting group, or the hydrogen in $-NHR^x$ is absent and $R^x$ is a divalent amino protecting group. In some embodiments, $R^x$ is $-C(=O)$ $C_{1-6}$ alkyl. For example, in some embodiments, $R^x$ is $-C(=O)CH_3$ (Ac), $-C(=O)CH_2CH_3$, or $-C(=O)CH(CH_3)_2$ (iBu). In other embodiments, $R^x$ is $-C(=O)$phenyl. In some other embodiments, the hydrogen in $-NHR^x$ is absent, and $R^x$ directed attaches to the nitrogen atom form an amino protecting group such as amidine type protecting group or the phthaloyl type protecting group. In some such embodiments, $R^x$ is N,N-dimethylformamidine

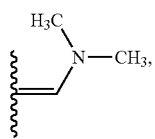

In some other embodiments, $R^x$ is

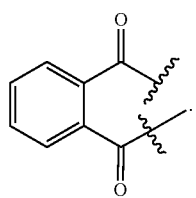 [SMILES: *C(=O)c1ccccc1C(*)=O]

In some embodiments of the compounds of Formula (I), (Ia), or (Ib), each $L^1$, $L^2$, and $L^3$ is independently a bond, $-C(=O)-$, $-C(=S)-$, $-S(=O)2-$, $-C(=O)NR^6-$, $-C(=S)NR^6-$, $-C(=O)O-$, $-C(=S)O-$, $-NR^6C(=O)NR^6-$, $-NR^6C(=S)NR^6-$, $-OP(=O)(OH)O-$, $-OP(=S)(OH)O-$, $-O-$, $-S-$, $-NR^6-$, optionally substituted $C_{1-10}$ alkylene, or optionally substituted 2 to 15 membered heteroalkylene wherein one or more carbon atoms (together with the hydrogen(s) attached to the carbon) are replaced with $C(=O)$, O, S or N, provided that at least one of $L^1$, $L^2$, and $L^3$ is not a bond. In some such embodiments, $R^6$ is H or optionally substituted $C_{1-6}$ alkyl, for example, methyl or trifluoromethyl. In some further embodiments, $L^1$ is a bond, $C_{1-10}$ alkylene, or 2 to 15 membered heteroalkylene, wherein one or more carbon atoms (i.e., $CH_2$) are replaced with $C(=O)$, O or N. In some embodiments, $L^1$ is a $C_{1-5}$ alkylene. In some other embodiments, $L^1$ is $-(CH_2CH_2O)-_{1-4}$. In some other embodiments, $L^1$ is 3 to 10 or 3 to 6 membered straight heteroalkylene where one, two or three carbon atoms is replaced by nitrogen or $C(=O)$. In some embodiments, $L^2$ is $-C(=O)-$, $-C(=O)NR^6--NR^6-$, or 2 to 15 membered heteroalkylene, wherein one or more carbon atoms are replaced with $C(=O)$, O or N. In some such embodiments, $R^6$ is H or methyl. In some embodiments, $L^2$ is $-(CH_2CH_2O)-_{1-4}$. In some other embodiments, $L^2$ is 3 to 10 or 3 to 6 membered straight heteroalkylene where one, two or three carbon atoms is replaced by nitrogen or $C(=O)$. In some further embodiments, $L^3$ is a bond, $C_{1-10}$ alkylene, or 2 to 15 membered heteroalkylene, wherein one or more carbon atoms are replaced with $C(=O)$, O or N. In some embodiments, $L^3$ is a $C_{1-5}$ alkylene. In some other embodiments, $L^3$ is $-(CH_2CH_2O)-_{1-4}$. In some other embodiments, $L^3$ is 3 to 10 or 3 to 6 membered straight heteroalkylene where one, two or three carbon atoms is replaced by nitrogen or $C(=O)$. In some embodiments, only $L^1$ is a bond. In some embodiments, only $L^2$ is a bond. In some embodiments, only $L^3$ is a bond. In other embodiments, at least one of $L^1$, $L^2$, and $L^3$ is a ring or ring system including optionally substituted $C_{6-10}$ arylene (e.g., phenylene), optionally substituted $C_{3-10}$ cycloalkylene (e.g., $C_{3-7}$ clyclalkylene), optionally substituted 5-10 membered hetetroarylene (e.g., 5 or 6 membered heteroarylene containing one, two or three heteroatoms selected from O, N or S), and optionally substituted 5 to 10 membered heterocyclylene (e.g., five or six membered heterocyclylene such as piperidylene, piperazinylene or morpholinylene). In some embodiments, $L^1$-$L^2$-$L^3$ may be $-(CH_2)_{2-6}C(=O)-$ (e.g., $-(CH_2)_4C(=O)-$). In some other embodiments, $L^1$-$L^2$-$L^3$ may be $-[(CH_2)_2O]_{1-5}-CH_2C(=O)-$ (e.g., $-[(CH_2)_2O]_2-CH_2C(=O)-$). In some other embodiments, $L^1$-$L^2$-$L^3$ may be $-[(CH_2)_2O]_{1-5}(CH_2)_{1-4}-$ (e.g., $-[(CH_2)_2O]_2(CH_2)_2-$).

In some embodiments of the compounds of Formula (I), $L^4$ is a bond. In other embodiments, $L^4$ is optionally substituted $C_{1-10}$ alkylene. For example, in some embodiments, $L^4$ is $-CH_2-$, $-CH_2CH_2-$, $-CH_2CH_2CH_2-$, or $-CH_2CH_2CH_2CH_2-$. In yet other embodiments, $L^4$ is an optionally substituted 2 to 15 membered heteroalkylene wherein one or more carbon atoms are replaced with $C(=O)$, O, S or N. For example, in some embodiments, $L^4$ is $(CH_2CH_2O)_p$, wherein p is 1, 2, 3, 4, or 5.

Additional non-limiting examples of the compounds of Formula (I) include:

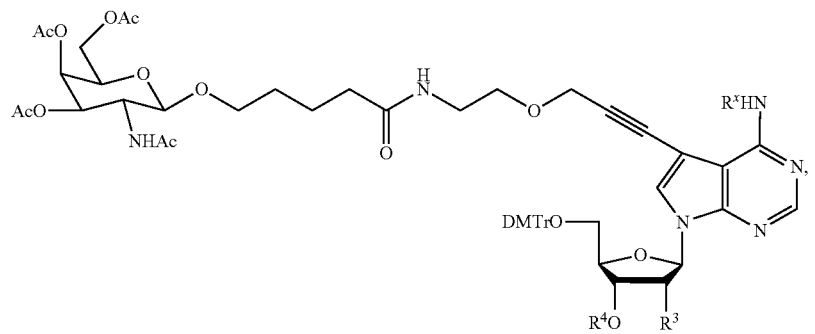
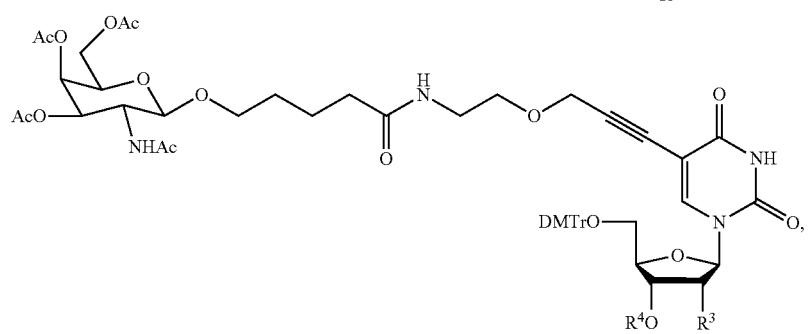
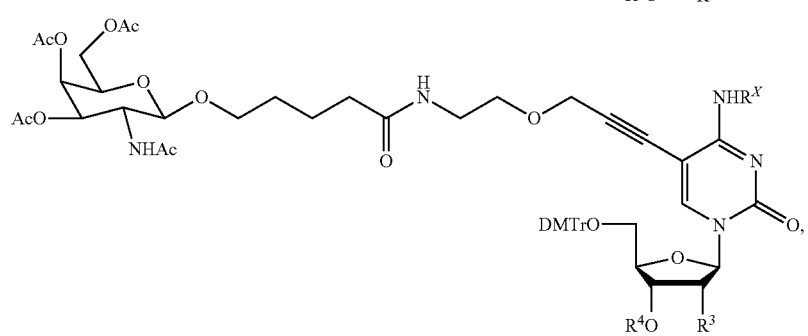
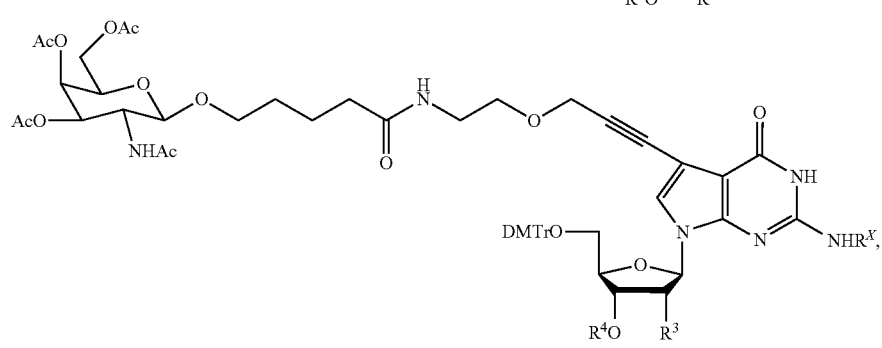
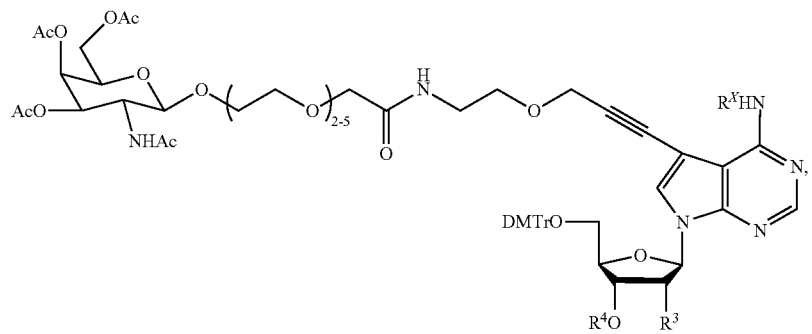

-continued
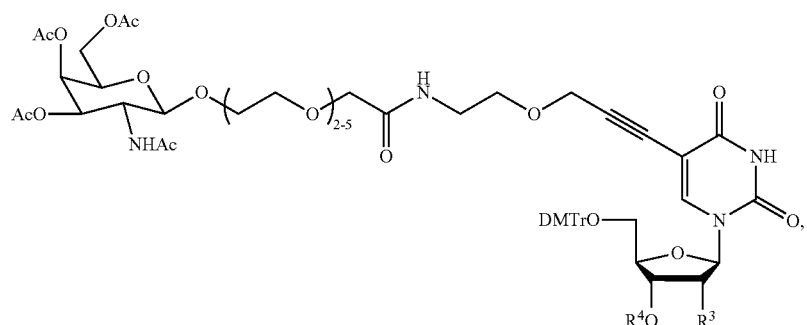
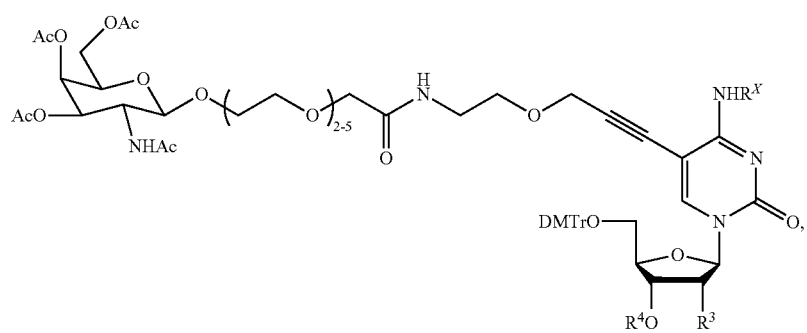
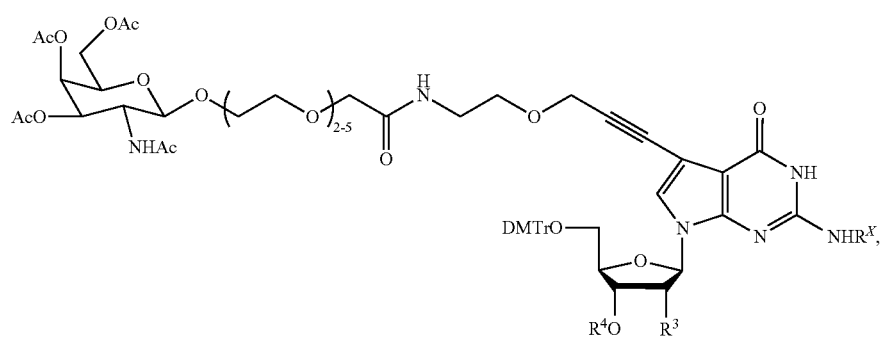
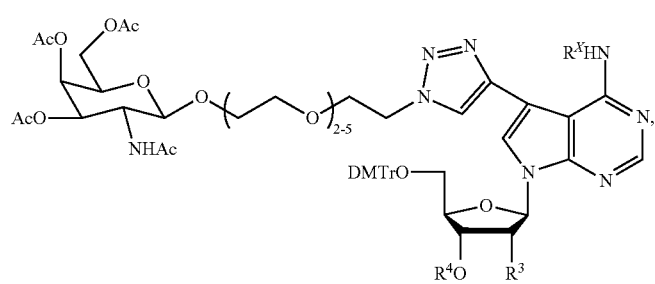
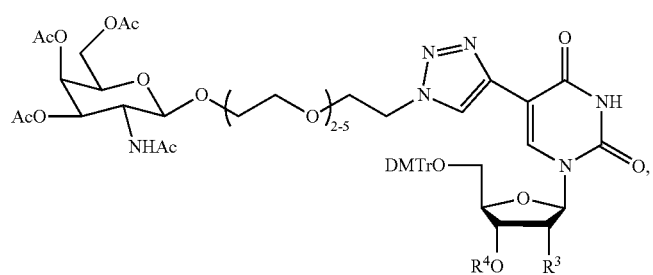

-continued

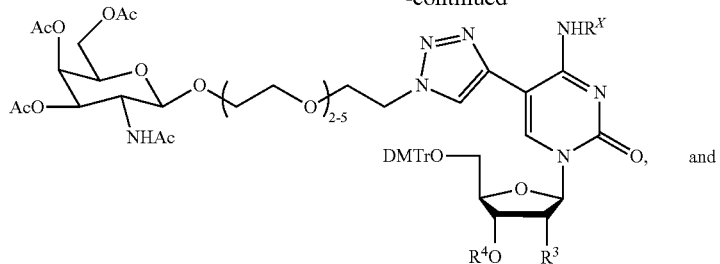

and

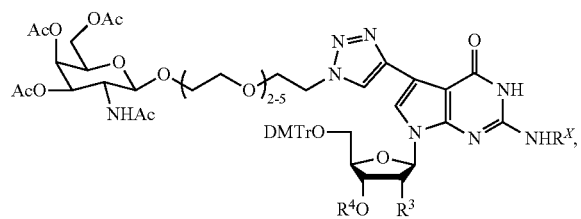

and pharmaceutically acceptable salts thereof;
wherein $R^3$ is hydrogen, halo, hydroxy, $C_{1-6}$ alkoxy, $C_{1-6}$ haloalkoxy, $C_{1-6}$ alkyl, $C_{1-6}$ haloalkyl, ($C_{1-6}$ alkoxy) $C_{1-6}$ alkyl, —O—($C_{1-6}$ alkoxy)$C_{1-6}$ alkyl, or a hydroxy protecting group; each $R^x$ is independently H, —C(=O)CH$_3$, —C(=O)Ph, or —C(=O)CH(CH$_3$)$_2$; and $R^4$ is —C(=O)CH$_2$CH$_2$C(=O)OH or

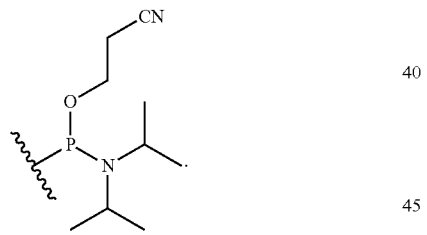

In further embodiments, $R^3$ is H, —F, —OCH$_3$, —OCH$_2$CH$_2$OCH$_3$, or —O-tertbutyldimethylsilyl. In further embodiments, the compound may be selected from:

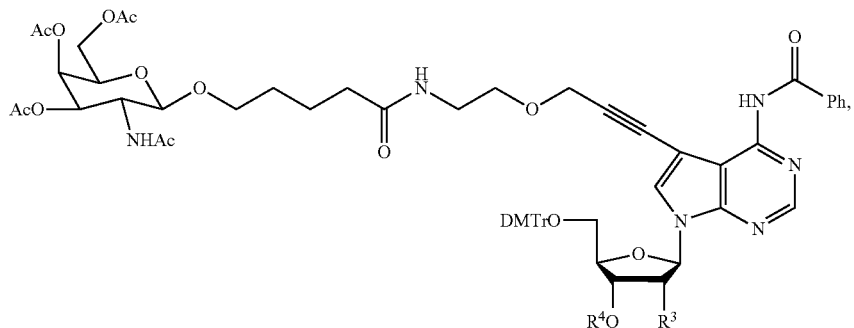

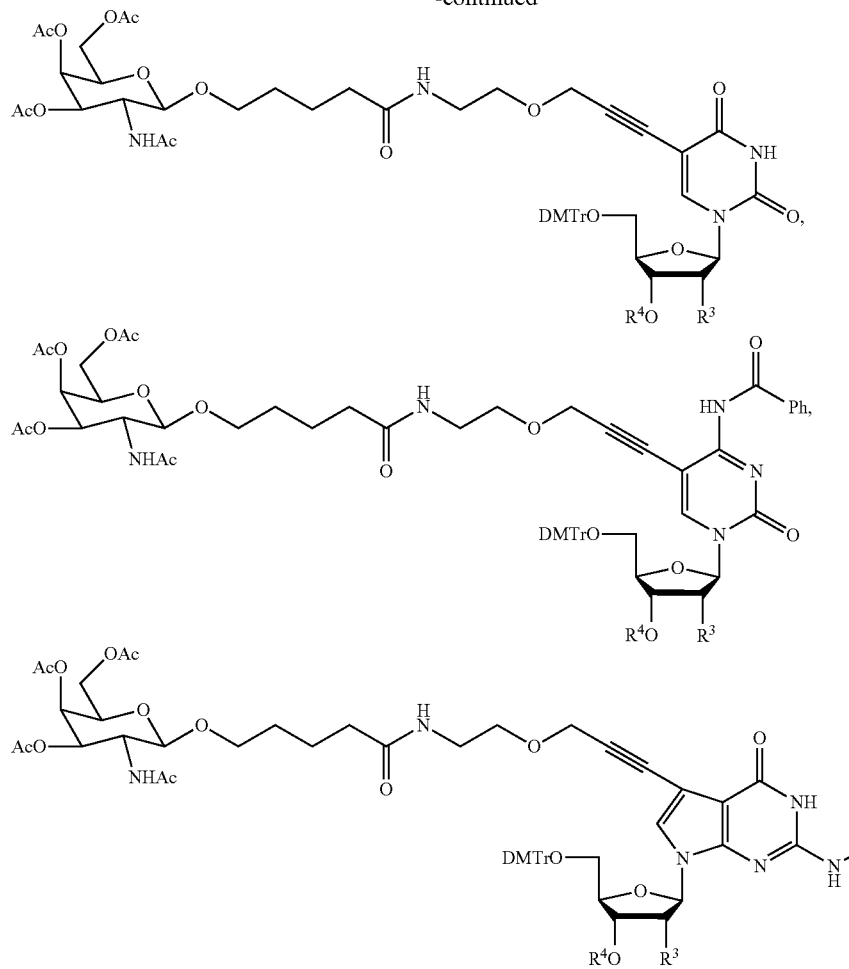

Solid Support Conjugated With GalNAc Nucleosides

Some embodiments of the present application relate to a solid support comprising the nucleoside compound of Formula (I), (Ia) or (Ib) as described herein covalently attached thereto, for example, via $R^4$ of the compound. In one embodiment, $R^4$ is —C(=O)CH$_2$CH$_2$C(=O)OH. In further embodiments, the nucleoside compound is covalently attached to the solid support via a moiety

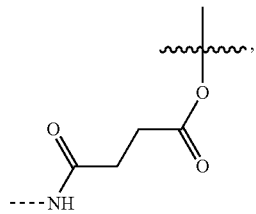

wherein the dashed line refers to the connection with the solid support, optionally through an additional linker, and the squiggly line refers to the point of the attachment of the 3' oxygen of the nucleoside compound to the remainder portion of the compound. In further embodiments, the solid support comprises an oligonucleotide, and the compound is incorporated into the oligonucleotide sequence, for example, to the terminal of the oligo sequence (either at the 5' end or at the 3' end). In any embodiments, the solid support may comprise controlled pore glass (CPG) or macroporous polystyrene (MPPS).

GalNAc Conjugated Nucleosides in Oligonucleotide Synthesis

Some embodiments of the present application relate to a method for preparing a synthetic oligonucleotide, comprising reacting a compound described herein, with an oligonucleotide. In some embodiments, the oligonucleotide comprises 1 to 100 base length, 5 to 50 base length, or 10 to 30 base lengths. In further embodiments, the reaction is conducted on a solid support.

Figure 6:
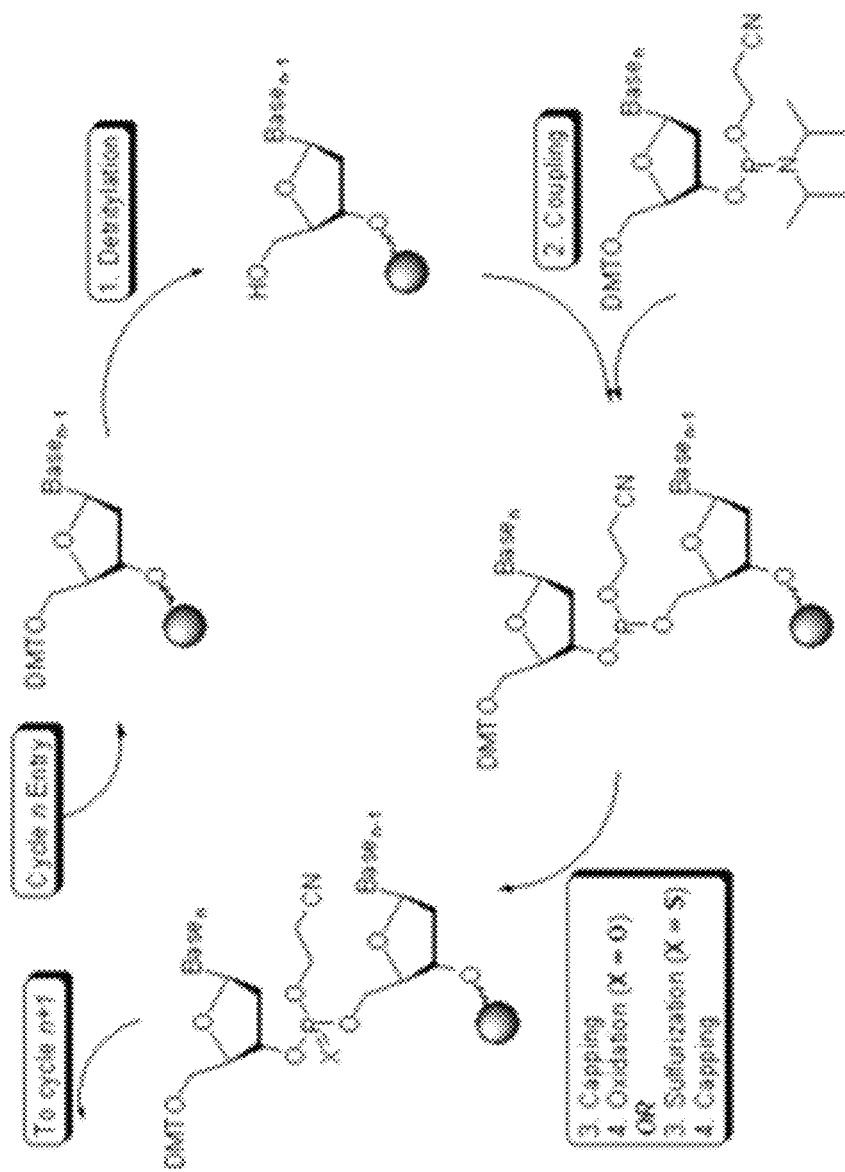
FIG. 6 illustrates a synthesis cycle for preparation of oligonucleotides using a nucleoside containing the phosphoramidite moiety according to an embodiment of the present application.

FIG. 6 illustrates a synthetic cycle of oligonucleotide using a nucleoside containing phosphoramidite moiety as described herein. The cycle typically includes the following steps as described below in details.

Step 1: De-blocking (Detritylation)

The DMTr group is removed with a solution of an acid, such as 2% trichloroacetic acid (TCA) or 3% dichloroacetic acid (DCA), in an inert solvent (dichloromethane or toluene). The orange-colored DMTr cation formed is washed out; the step results in the solid support-bound oligonucleotide precursor bearing a free 5'-terminal hydroxy group.

Step 2: Coupling

A 0.02-0.2M solution of nucleoside phosphoramidite (or a mixture of several phosphoramidites) in acetonitrile is activated by a 0.2-0.7 M solution of an acidic azole catalyst, 1H-tetrazole, 5-ethylthio-1H-tetrazole, 2-benzylthiotetrazole, 4,5-dicyanoimidazole, or a number of similar compounds. The mixing is usually very brief and occurs in fluid lines of oligonucleotide synthesizers (see below) while the components are being delivered to the reactors containing solid support. The activated phosphoramidite in 1.5-20-fold excess over the support-bound material is then brought in contact with the starting solid support (first coupling) or a support-bound oligonucleotide precursor (following couplings) whose 5'-hydroxy group reacts with the activated phosphoramidite moiety of the incoming nucleoside phosphoramidite to form a phosphite triester linkage. The reaction is also highly sensitive to the presence of water, particularly when dilute solutions of phosphoramidites are used, and is commonly carried out in anhydrous acetonitrile. Upon the completion of the coupling, any unbound reagents and by-products are removed by washing.

Step 3: Capping

The capping step is performed by treating the solid support-bound material with a mixture of acetic anhydride and 1-methylimidazole or, less often, DMAP as catalysts and, in the phosphoramidite method, serves two purposes. After the completion of the coupling reaction, a small percentage of the solid support-bound 5'—OH groups (0.1 to 1%) remains unreacted and needs to be permanently blocked from further chain elongation to prevent the formation of oligonucleotides with an internal base deletion commonly referred to as (n-1) shortmers. The unreacted 5'-hydroxy groups are, to a large extent, acetylated by the capping mixture.

Step 4: Oxidation

The newly formed tricoordinated phosphite triester linkage is not natural and is of limited stability under the conditions of oligonucleotide synthesis. The treatment of the support-bound material with iodine and water in the presence of a weak base (pyridine, lutidine, or collidine) oxidizes the phosphite triester into a tetracoordinated phosphate triester, a protected precursor of the naturally occurring phosphate diester internucleosidic linkage. Oxidation may be carried out under anhydrous conditions using tert-Butyl hydroperoxide or (1S)-(+)-(10-camphorsulfonyl)-oxaziridine (CSO). The step of oxidation may be substituted with a sulfurization step to obtain oligonucleotide phosphorothioates. In the latter case, the sulfurization step is best carried out prior to capping.

In solid-phase synthesis, an oligonucleotide being assembled is covalently bound, via its 3'-terminal hydroxy group, to a solid support material and remains attached to it over the entire course of the chain assembly. The solid support is contained in columns whose dimensions depend on the scale of synthesis and may vary between 0.05 mL and several liters. At the end of the chain assembly, the oligonucleotide is released from the solid support and is eluted from the column or the well. The two most often used solid-phase materials are controlled pore glass (CPG) and macroporous polystyrene (MPPS).

In contrast to organic solid-phase synthesis and peptide synthesis, the synthesis of oligonucleotides proceeds best on non-swellable or low-swellable solid supports. The two most often used solid-phase materials are controlled pore glass (CPG) and macroporous polystyrene (MPPS).

CPG is commonly defined by its pore size. In oligonucleotide chemistry, pore sizes of 500, 1000, 1500, 2000, and 3000 Å are used to allow the preparation of about 50, 80, 100, 150, and 200-mer oligonucleotides, respectively. To make native CPG suitable for further processing, the surface of the material is treated with (3-aminopropyl)triethoxysilane to give aminopropyl CPG. The aminopropyl arm may be further extended to result in long chain aminoalkyl (LCAA) CPG. The amino group is then used as an anchoring point for linkers suitable for oligonucleotide synthesis.

MPPS suitable for oligonucleotide synthesis is a low-swellable, highly cross-linked polystyrene obtained by polymerization of divinylbenzene, styrene, and 4-chloromethylstyrene in the presence of a porogeneous agent. The macroporous chloromethyl MPPS obtained is converted to aminomethyl MPPS.

EXAMPLES

Some aspects of the embodiments discussed above are disclosed in further detail in the following examples, which are not in any way intended to limit the scope of the present disclosure. Those in the art will appreciate that many other embodiments also fall within the scope of the compositions, kits and methods of the present application, as is described herein above and in the claims.

Example 1. Preparation of 2,2,2-trifluoro-N-(2-(prop-2-yn-1-yloxy)ethyl)acetamide

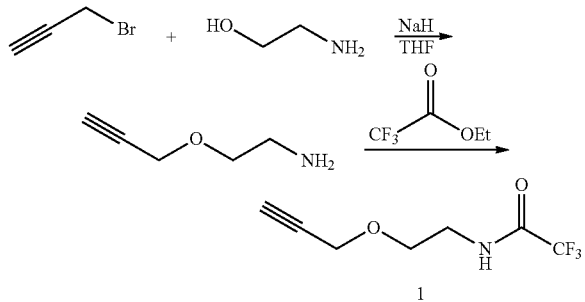

The 2,2,2-trifluoro-N-(2-(prop-2-yn-1-yloxy)ethyl)acetamide linker (1) can be used to conjugate GalNAc to a natural, modified, or unnatural base in a nucleoside. The linker was prepared using a two-step process.

Step 1: Sodium hydride (36 g, 0.9 mol, 60% dispersion in mineral oil) was stirred in 50 mL of tetrahydrofuran (THF). The mixture was allowed to stand until it settled, and the THF was decanted. This washing process was repeated an additional time. To the washed sodium hydride, 133 mL of THF was added and the resulting suspension was cooled to 0° C. Ethanolamine (30.54 g, 0.5 mol) was added dropwise to the suspension over 10 minutes and the reaction mixture was stirred at ambient temperature for 2 hours. The reaction mixture was cooled to 0° C. and propargyl bromide (89.28 g, 0.6 moles, 80% in toluene) was added dropwise. After addition was completed, the reaction was stirred at ambient for 16 hours. The mixture was then diluted with 200 mL of THF, filtered, and the solids were washed with THF (500 mL). The THF filtrate was combine and evaporated. The residue was purified by vacuum distillation to give 21.44 g aminoethyl propargyl ether (AEP) with boiling point of about 95° C./6 mmHg.

Step 2: To a solution of ethyl trifluoroacetate (46.0 g, 0.324 mol) in 100 mL of THF was added aminoethyl propargyl ether (21.4 g, 0.216 mole) dropwise over 15 minutes at 0° C. After addition was complete, the reaction mixture was stirred at ambient temperature for two hours, transferred to a separatory funnel and washed with water (100 mL). The aqueous layer was separated and extracted with EtOAc (ethyl acetate)/THF (1:1, 100 mL). The organic layers were combined and evaporated to give the crude product. The crude product was further purified by silica gel chromatography with eluting gradient 0-10% ethyl acetate/dichloromethane (DCM) to give 34.42 g 2,2,2-trifluoro-N-(2-(prop-2-yn-1-yloxy)ethyl)acetamide (1). Compound (1) is also referred to as AEP-TFA.

Example 2. Preparation of ddU(AEP-TFA)

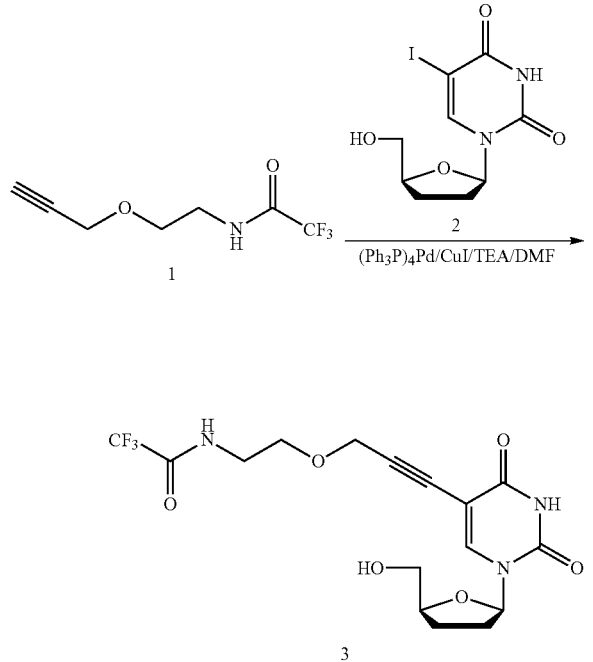

To a solution of 5-iodo-ddU (2) (6.76 g, 0.02 mole) in 100 mL dry dimethylformamide (DMF) was added 2,2,2-trifluoro-N-(2-(prop-2-yn-1-yloxy)ethyl)acetamide (1) (11.71 g, 0.06 mol), CuI (0.76 g, 0.004 mol), Pd(PPh$_3$)$_4$ (2.31 g, 0.002 mol) and triethylamine (TEA) (5.86 mL, 0.042 mole). The reaction mixture was stirred at ambient temperature under an argon atmosphere for 4 hours. The reaction was monitored by HPLC and was determined to be completed when HPLC showed that the starting material 5-iodo-ddU (2) was less than 3%. Bicarbonate resin was added into reaction mixture and the resulting mixture was stirred for one hour. The mixture was filtered and the solid was washed with DCM-methanol (1:1). The filtrate was evaporated to give the crude product and it was further purified by chromatography with 250 g silica gel and eluting gradient 0-10% methanol (MeOH)/DCM to give 6-6.5 g product ddU(AEP-TFA) (3).

Similar derivatized nucleosides (e.g., ddG(AEP-TFA), ddC(AEP-TFA), ddA(AEP-TFA), ddT(AEP-TFA), and others) may be prepared according to the methods described in this example.

Example 3. Preparation of GalNAc Moiety for Nucleoside Conjugation

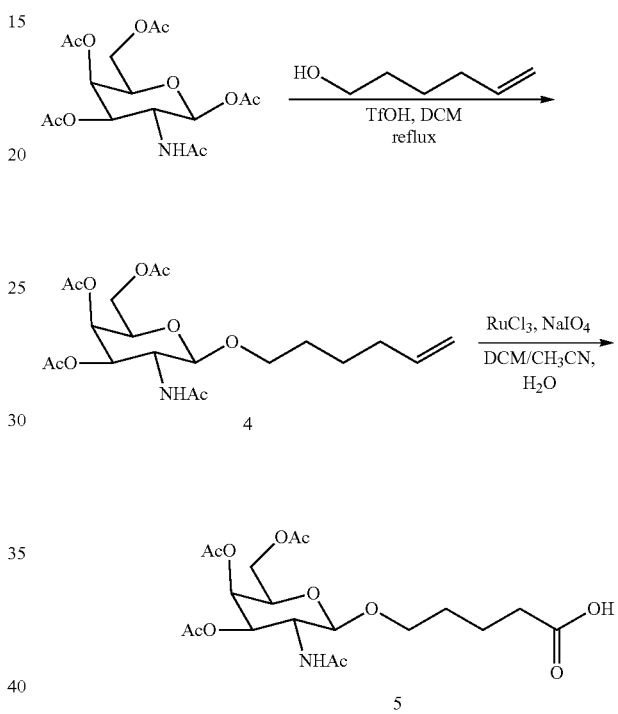

β-D-Galactosamine pentaacetate (10 g, 25.68 mmol) and 5-hexen-1-ol (2.83 g, 28.25 mmol) were dissolved in anhydrous 1,2-dichloroethane (100 mL). Trifluoromethanesulfonic acid (TfOH) (0.58 g, 3.85 mmol) was added and the mixture was refluxed for about 18 hours. The reaction mixture was then cooled to room temperature and quenched with 1 M NaHCO$_3$ solution (50 mL), and the organic layer was separated. The organic layer was washed with water (50 mL), brine (50 mL), dried over anhydrous Na$_2$SO$_4$, and evaporated to dryness under reduced pressure to give 11.52 g crude (4).

The above crude (4) (3.9 g, 9.08 mmol) was dissolved in DCM (20 mL), then acetonitrile (20 mL) and H$_2$O (20 mL) were added, followed by ruthenium chloride (75 mg, 0.36 mmol). The mixture was cooled to 5° C. and 4.5 mol equiv. of sodium (meta)periodate (8.7 g, 40.67 mmol) was added. The reaction mixture was stirred for 15 minutes at 5° C., then warmed to room temperature and stirred for an additional 2 hours. Completion of the reaction was confirmed by TLC. The reaction mixture was filtered to remove solids and 9.5 g of Na$_2$S$_2$O$_3$ was added to the filtrate. The filtrate was then filtered and evaporated under reduced pressure to afford the crude product (5) (12.23 g).

Example 4. Preparation of
DMT-dU-EO-GalNAc-Phosphoramidite/CGP
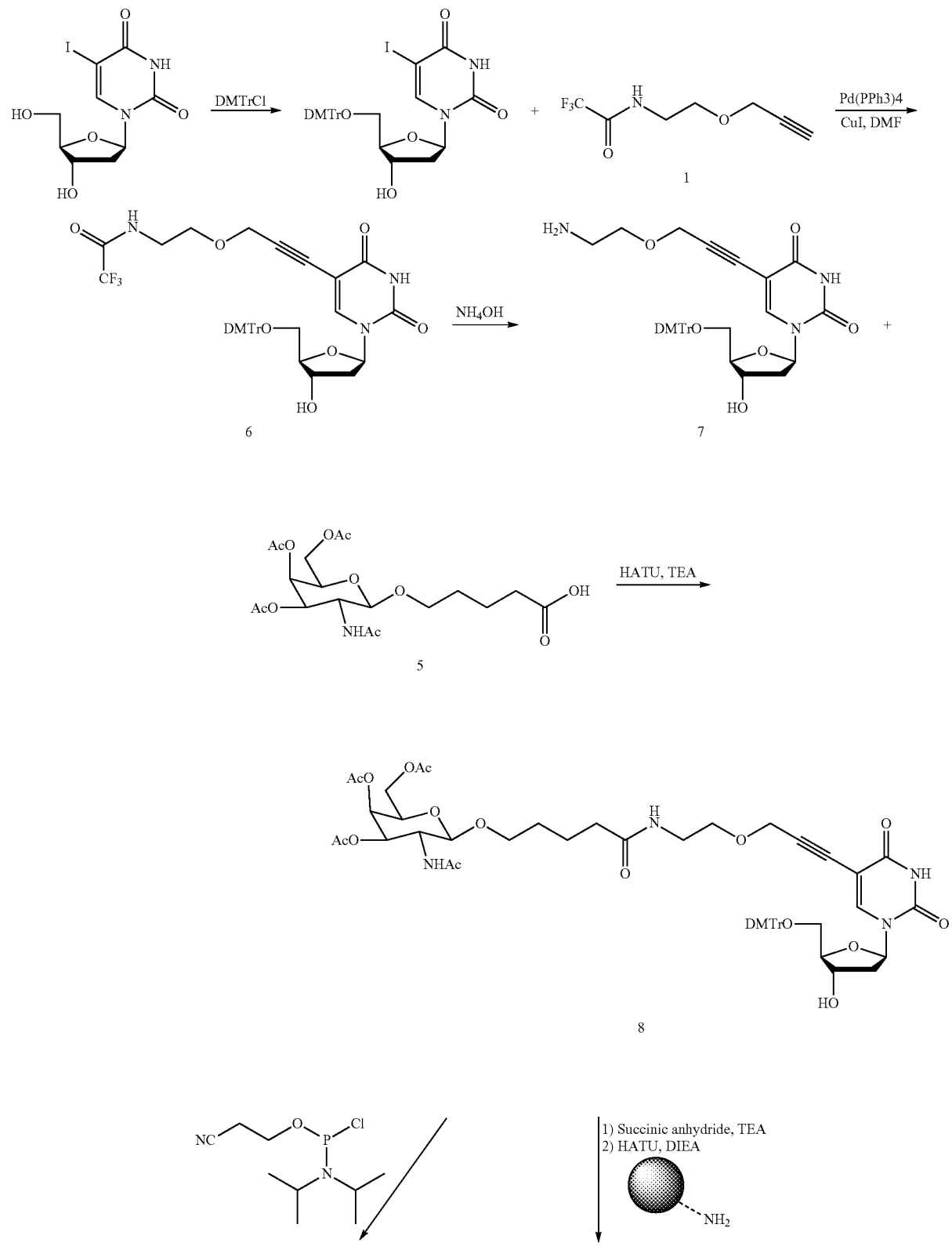

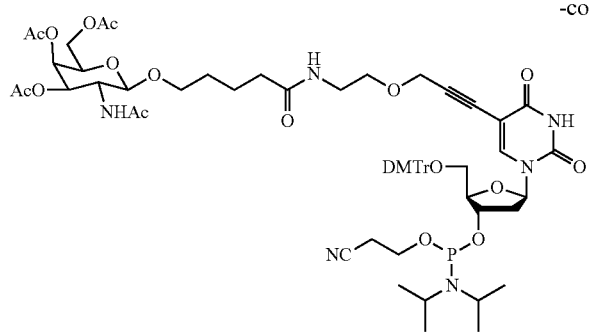

9

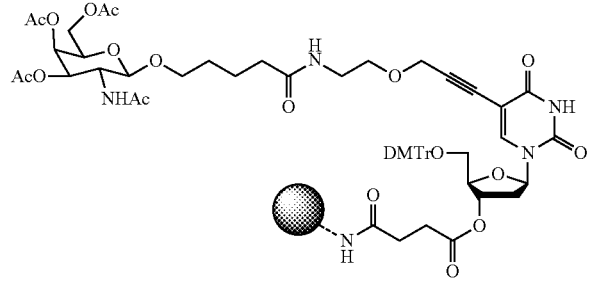

10

In a 100 mL round bottom flask, 5-iodo-2'-deoxyuridine (1.0 g, 2.82 mmol) was dissolved in pyridine (30 mL). DMT-Cl (1.04 g, 3.07 mmol) was added immediately. the reaction mixture was stirred at room temperature for 12 hours. Completion of the reaction was confirmed by TLC. This mixture was then poured into saturated NaHCO$_3$ (51 mL), and the organic layer was separated, washed with water, brine and dried over Na$_2$SO$_4$. After filtration, the organic layer was concentrated to dryness under vacuum. The crude product was purified by column purification using DCM/MeOH (2% to 8% MeOH). The pure fractions were collected and concentrated to dryness under vacuum to obtain the 5'-DMT-protected-5-iodo-2'deoxyuridine (1.47 g, 80% yield). MS: found: [M−H]=655.5; calc: [M−H]=655.1.

In a 100 mL RB flask, the 5'-DMT-protected-5-iodo-2'deoxyuridine (1.31 g, 1.99 mmol), Pd(PPh$_3$)$_4$ (0.23 g, 0.10 mmol) and CuI (0.115 g, 6.0 mmol) were added. After removing air, TEA (0.80 g, 8.0 mmol), Compound 1 (1.16 g, 6.0 mmol) and DMF (30 mL) were added. The reaction mixture was stirred at room temperature for 5 hours. Completion of the reaction was confirmed by TLC, and this mixture was then poured into saturated NaHCO$_3$ (51 mL). DCM (80 mL) was added, and the organic layer was separated, washed with water, brine and dried over Na$_2$SO$_4$. After filtration, the organic layer was concentrated to dryness under vacuum. The crude product was purified by column purification using DCM/MeOH (0% to 10% MeOH). The pure fractions were collected and concentrated to dryness under vacuum to obtain Compound 6 (320 mg, 22% yield). MS: found: [M−H]=722.8; calc: [M−H]=722.2.

In a 50 mL round bottom flask, Compound 6 (320 mg, 0.44 mmol) was dissolved in MeCN (20 mL), and aqueous NH$_4$OH (1.5 mL) was added. The reaction mixture was stirred at room temperature for 12 hours. Completion of the reaction was confirmed by TLC. This mixture was then poured into saturated NaHCO$_3$ (10 mL), and DCM (20 mL) was added. The organic layer was separated, washed with water, brine and dried over Na$_2$SO$_4$. After filtration, the organic layer was concentrated to dryness under vacuum. The crude product was purified by column purification using DCM/MeOH (0% to 20% MeOH). The pure fractions were collected and concentrated to dryness under vacuum to obtain Compound 7 (160 mg, 58% yield). MS: found: [M−H]=626.8; calc: [M−H]=626.3.

In a 50 mL round bottom flask, Compound 7 (50 mg, 0.079 mmol) was dissolved in DMF (5 mL). Compound 5 (Peracetylated GalNAc pentenoic acid) (40 mg, 0.086 mmol), HATU (60 mg, 0.16 mmol), DIEA (40 mg, 0.32 mmol). The reaction mixture was stirred at room temperature for 24 hours. Completion of the reaction was confirmed by TLC. This mixture was then poured into saturated NaHCO$_3$ (10 mL), and DCM (20 mL) was added. The organic layer was separated, washed with water, brine and dried over Na$_2$SO$_4$. After filtration, the organic layer was concentrated to dryness under vacuum. The crude product was purified by column purification using DCM/MeOH (0% to 10% MeOH). The pure fractions were collected and concentrated to dryness under vacuum to obtain Compound 8 (22 mg, 26% yield). MS: found: [M−H]=1056.1; calc: [M−H]=1056.1.

In a 50 mL round bottom flask, Compound 8 (450 mg, 0.43 mmol) was dissolved in DCM (20 mL). 2-Cyanoethyl N,N-diisopropylchlorophosphoramindite (120 mg, 0.51 mmol), DIEA (164 mg, 1.26 mmol) were added. The reaction mixture was stirred at room temperature for 2 hours. Completion of the reaction was confirmed by TLC, and this mixture was then poured into saturated NaHCO$_3$ (10 mL). DCM (20 mL) was added, and the organic layer was separated, washed with water, brine and dried over Na$_2$SO$_4$. After filtration, the organic layer was concentrated to dryness under vacuum. The crude product was purified by column purification using DCM/TEA (0% to 80% TEA). The pure fractions were collected and concentrated to dryness under vacuum to obtain Compound 9 (120 mg, 22% yield). MS: found: [M+H]=1258.1; calc: [M+H]=1258.3. $^{31}$PNMR (mixture of diastereomers, DMSO-d$_6$): δ 147.481, 147.084.

Preparation of GalNAc-conjugated uridine-CPG compounds: Step 1: In a 50 mL round bottom flask, Compound 8 (83 mg, 0.079 mmol) was dissolved in DCM (10 mL). Succinic anhydride (11 mg, 0.12 mmol) and TEA (16 mg, 0.16 mmol) were added. The reaction mixture was stirred at room temperature for 2 hours. Completion of the reaction was confirmed by TLC, and this mixture was then poured into saturated NaHCO$_3$ (10 mL). DCM (20 mL) was added, and the organic layer was separated, washed with water, brine and dried over Na$_2$SO$_4$. After filtration, the organic layer was concentrated to dryness under vacuum. The crude product was purified by column purification using DCM/MeOH (0% to 10% MeOH). The pure fractions were collected and concentrated to dryness under vacuum to obtain white solid (60 mg, 66% yield). MS: found: [M−H]=1156.10; calc: [M−H]=1156.2.

Step 2: In a 50 mL round bottom flask, compound from step 1 (82 mg, 0.072 mmol) was dissolved in 10 mL MeCN. HATU (27.4 mg, 0.072 mmol) and DIEA (27.9 mg, 0.28 mmol) were added. After 5 min, LCAA CPG (1000 Å, 2 g) was added, and the reaction mixture was stirred at room temperature for 3 hours. After filtration, the resulting product was washed with MeCN (50 ml×3) and THF (50 ml×3), then dried under vacuum to afford uncapped CGP product 10. Capping A reagent: (THF/acetic anhydride/pyridine 80/10/10 v/v/v, 5 mL) and Capping B reagent: (1-methyl-imidazole/THF, 16/84, v/v, 5 mL) were added into the flask, and the mixture was stirred at room temperature for 2 hours. After filtration, capped CPG product 10 was washed with EtOH (50 mL×3), EtOH/Pyridine (10%) (50 mL×3), THF (50 mL×3) and DCM (50 mL×3), then dried under vacuum. Loading was determined by standard DMTr assay by UV-Vis (498 nm) to be 22 μmol/g.

Example 5. Preparation of DMT-dA-EO-GalNAc-Phosphoramidite

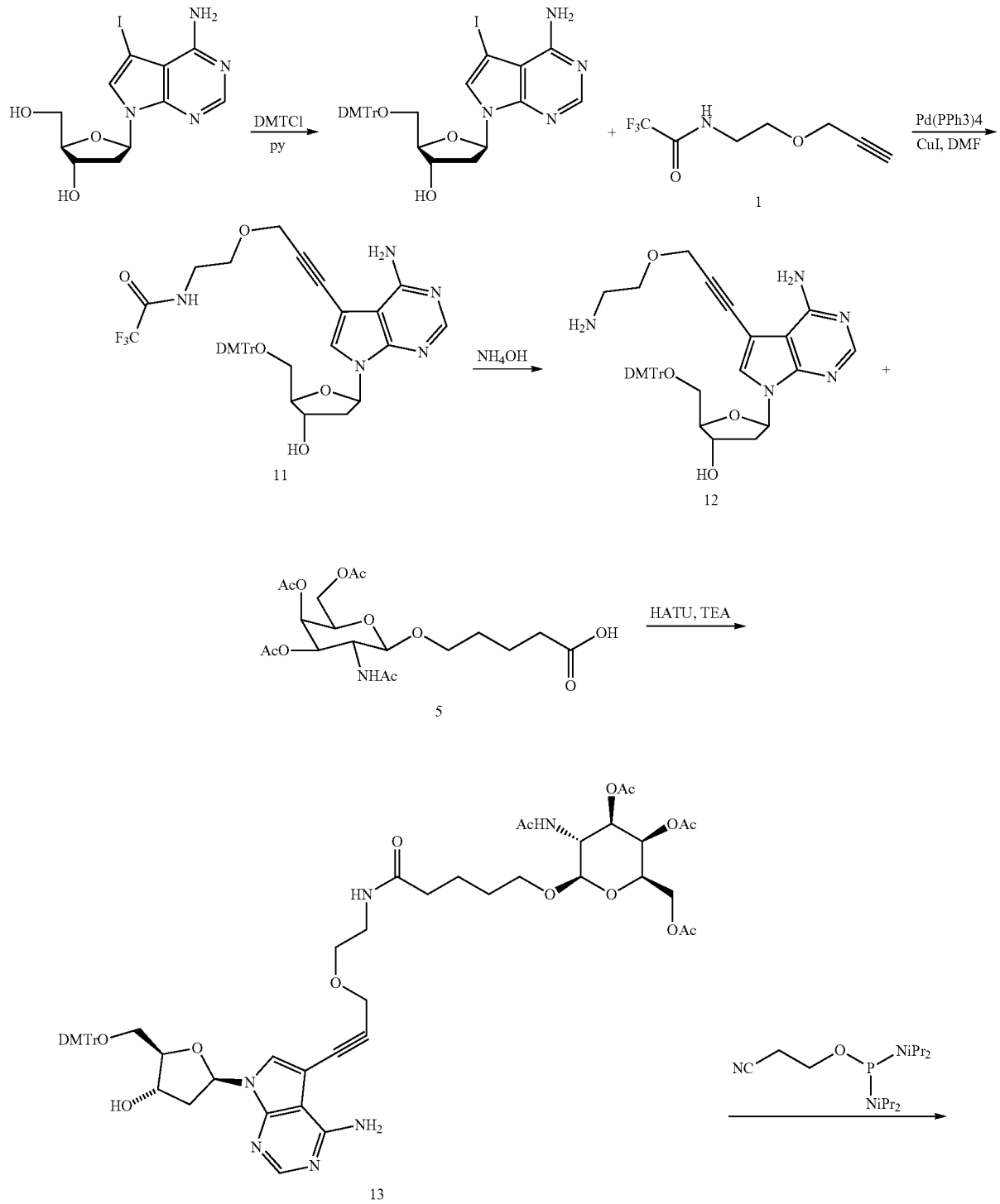

-continued

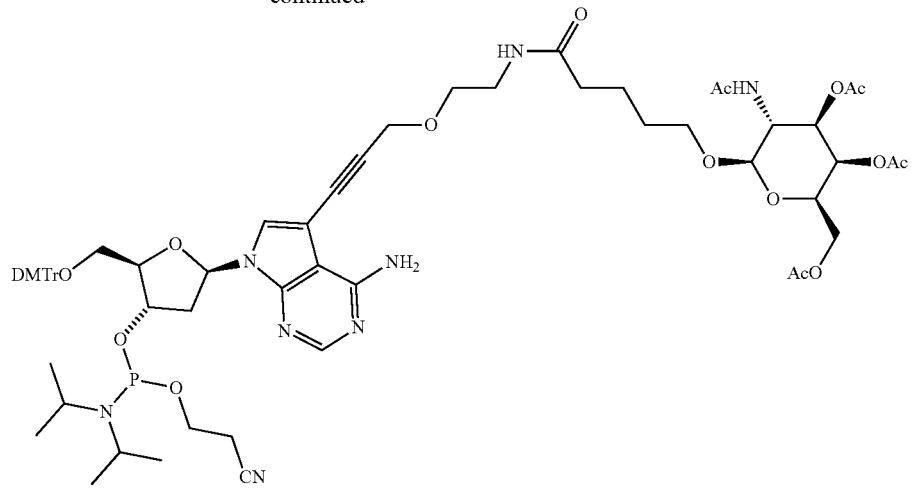

14

7-deaza-2'-deoxy-7-iodoadenosine (1.5 g, 4.0 mmol) was dissolved in pyridine (15 mL). The solution was cooled with an ice bath, and DMTrCl (1.2 g, 4.4 mmol) was added portionwise. The reaction was allowed to warm up to the room temperature and was monitored by TLC. After Completion of the reaction, it was quenched by adding methanol (1.0 mL). The solvent was evaporated, and the crude was subjected to flash column purification using DCM/MeOH (5% MeOH) to afford 5'-DMT protected-7-deaza-2'-deoxy-7-isodoadenosine (2.3 g, 85% yield) as a white solid. MS: calc: [M−H]=677.13, found [M−H]=677.7.

5'-DMT protected-7-deaza-2'-deoxy-7-isodoadenosine (1.2 g, 1.77 mmol), compound 1 (0.75 g, 3.85 mmol), Pd(PPh$_3$)$_4$ (440 mg, 0.38 mmol), CuI (150 mg, 0.76 mmol) and triethylamine (0.8 ml) was dispersed in DMF (10.0 mL). The solution purged with nitrogen, and stirred for 2 days. The reaction was monitored by TLC. After completion of the reaction, the mixture was filtered. The solution was diluted with ethyl acetate (30 mL) and washed with water (3×30 mL) and brine (20 mL). The organic layer was dried over sodium sulfate, filtered, and concentrated. The crude was subjected to flash column purification using DCM/MeOH (0% to 10% MeOH) to afford compound 11 (1.0 g, 76% yield) as a yellow oil. MS calc: [M+H]=746.27, found: [M+H]=746.7.

Compound 11 (1.0 g, 1.34 mmol) was dissolved in acetonitrile (5.0 mL), followed by the addition of aqueous ammonia (20 mL, 30%). The reaction was stirred at room temperature for two days and was monitored by TLC. The organic solvents were evaporated, and the mixture was extracted with ethyl acetate (20 mL). The organic layer was dried over sodium sulfate, filtered, and concentrated. The crude was subjected to flash column purification using MeOH/DCM=(0% to 15% MeOH) to afford compound 12 (0.62 g, 72% yield) as a white foam. MS calc: [M+H]=650.29, found [M+H]=650.8.

Compound 12 (500 mg, 0.77 mmol), compound 5 (400 mg, 0.89 mmol), triethylamine (320 µL) and HATU (440 mg, 1.16 mmol) was dissolved in THF (5.0 mL). The reaction was stirred at room temperature for two hours and was monitored by TLC. The solvents were evaporated, and the residual was diluted with ethyl acetate (30 mL), washed with water (3×30 mL) and brine (20 mL). The organic layer was dried over sodium sulfate, filtered, and concentrated. The crude was subjected to flash column purification with MeOH/DCM (0% to 15% MeOH) to afford compound 13 (513 mg, 62% yield) as a white solid. MS calc: [M+H]=1079.45, found [M+H]=1079.8.

Compound 13 (500 mg, 0.46 mmol), 2-cyanoethyl tetraisopropylphosphorodiamidite (210 mg, 0.70 mmol), and diisopropyl ammonium tetrazolide (20 mg, 0.115 mmol) was dispersed in DCM (5.0 mL). The reaction was purged with nitrogen and stirred at room temperature overnight and was monitored by TLC. The solution was washed with water (3×5 mL) and brine (5 mL). The organic layer was dried over sodium sulfate, filtered, and concentrated. The residual was redissolved in acetonitrile (5 mL) and washed with heptane (3×5 ml). The solvents were evaporated, and the crude was subjected to flash column purification with DCM/TEA (4% TEA) to afford compound 14 (240 mg, 62% yield) as a white solid. MS calc: [M+H]=1279.56, found [M+H]=1280.1. $^{31}$PNMR (mixture of diastereomers, DMSO-d$_6$): δ 147.626, 146.969.

Example 6. Preparation of DMT-dANHBz-EO-GalNAc-Phosphoramidite/CPG

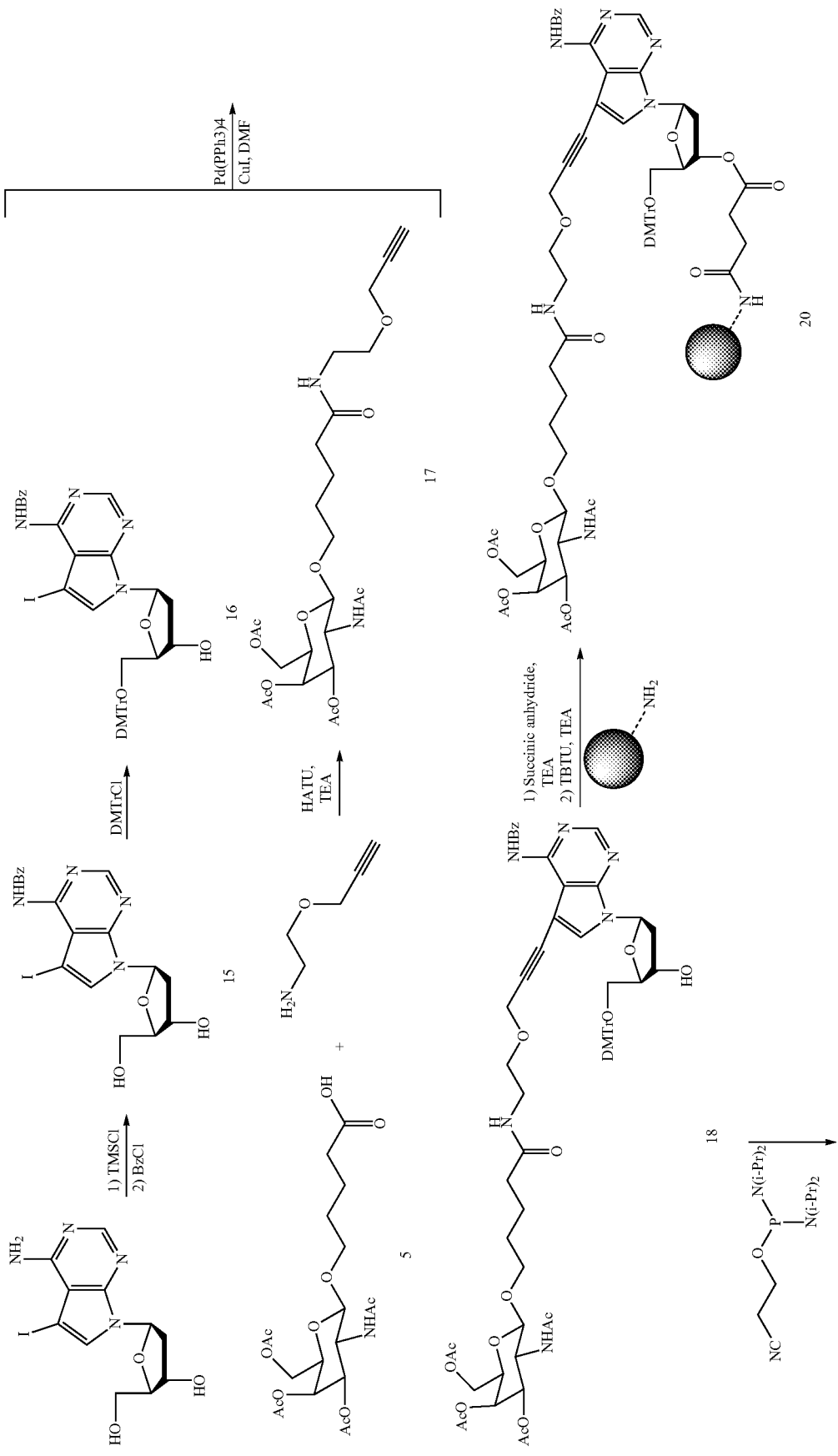

-continued
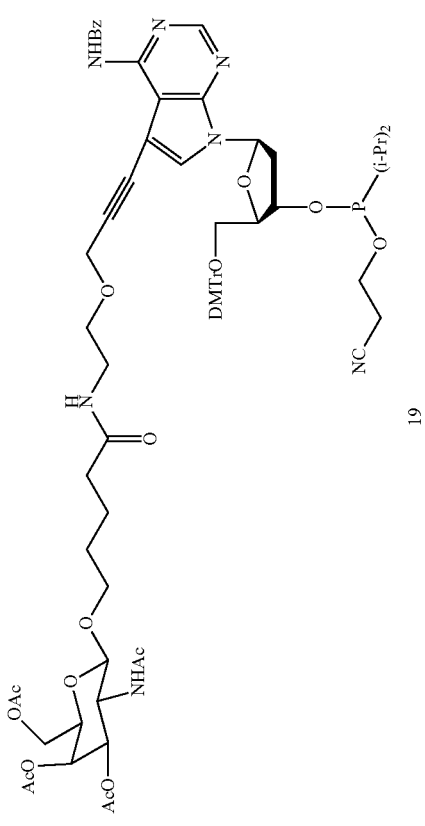
19

7-Deaza-2'-deoxy-7-iodoadenosine (1.0 g, 2.66 mmol) was dissolved in pyridine (15 mL). The solution was cooled with an ice bath, and TMSCl (5.2 ml, 26.6 mmol) was added dropwise. The reaction was allowed to warm up to room temperature for half an hour, and the mixture was then cooled again with an ice bath, followed by the addition of BzCl (0.52 ml, 2.91 mmol). After one hour, the reaction was quenched by adding water (5 mL). The organic solvents were evaporated, and the residual was diluted with ethyl acetate (30 mL), and washed with water (3×30 mL) and brine (20 mL). The organic layer was dried over sodium sulfate, filtered, and concentrated. The crude was subjected to flash column purification with DCM/MeOH (0% to 10% MeOH) to afford compound 15 (0.42 g, 33% yield) as a white solid. MS calc: [M+H]=481.03, found [M+H]=481.5.

Compound 15 (425 mg, 0.83 mmol) was dissolved in pyridine (5.0 mL). The solution was cooled with an ice bath, and DMTrCl (330 mg, 0.92 mmol) was added portionwise. The reaction was allowed to warm up to room temperature for half an hour and was monitored by TLC. After completion of the reaction, it was quenched by adding methanol (1.0 mL). The solvents were evaporated, and the crude was subjected to flash column purification with DCM/MeOH (0% to 5% MeOH) to afford compound 16 (500 mg, 77% yield) as a white solid. MS calc: [M+H]=783.16, found [M+H]: 783.6.

Compound 5 (1 g, 2.27 mmol), aminoethyl propargyl ether (337 mg, 3.41 mmol), triethylamine (947 µL, 6.81 mmol) and HATU (1.3 g, 3.41 mmol) was dissolved in THF (15 mL). The reaction was stirred at room temperature for two hours and was monitored by TLC. The solvents were evaporated, and the residual was diluted with ethyl acetate (30 mL), washed with water (3×30 mL) and brine (20 mL). The organic layer was dried over sodium sulfate, filtered, and concentrated. The crude was subjected to flash column purification with DCM/MeOH (0% to 15% MeOH) to afford compound 17 (567 mg, 47% yield) as a white solid. MS calc: [M−H]=527.23, found [M−H]=527.4.

Compound 16 (500 mg, 0.64 mmol), compound 17 (500 mg, 0.96 mmol), Pd(PPh$_3$)$_4$ (148 mg, 0.13 mmol), CuI (25 mg, 0.13 mmol) and triethylamine (267 µL, 1.92 mmol) was dispersed in DMF (5.0 mL). The reaction mixture was purged with nitrogen and stirred at room temperature for 2 days. The reaction was monitored by HPLC. After completion of the reaction, the mixture was filtered. The filtrate was diluted with ethyl acetate (30 mL) and washed with water (3×30 mL) and brine (20 mL). The organic layer was dried over sodium sulfate, filtered, and concentrated. The crude was subjected to flash column purification with DCM/MeOH (0% to 10% MeOH) to afford compound 18 (468 mg, 62% yield) as pale yellow solid. MS calc: [M+H]=1184.27, found [M+H]=1184.0.

Compound 18 (200 mg, 0.17 mmol), 2-cyanoethyl tetraisopropylphosphorodiamidite (102 mg, 0.34 mmol), and diisopropyl ammonium tetrazolide (7.3 mg, 0.043 mmol) was dispersed in DCM (5.0 mL). The reaction was purged with nitrogen and stirred at room temperature overnight and monitored by TLC. The solution was washed with water (3×5.0 mL) and brine (5.0 mL). The organic layer was dried over sodium sulfate, filtered, and concentrated. The residual was redissolved in acetonitrile (5.0 mL) and washed with heptane (3×5.0 mL). The solvents were evaporated. The crude was subjected to flash column purification with DCM/TEA (4% TEA) to afford compound 19 (110 mg, 47% yield) as a white solid. MS calc: [M+H]=1384.49, found [M+H]=1384.3. $^{31}$P-NMR (mixture of diastereomers, DMSO-d$_6$): δ 146.923, 146.381.

Compound 18 (50 mg, 0.042 mmol), succinic anhydride (6.3 mg, 0.063 mmol), and triethylamine (21 mg, 0.21 mmol) was dissolved in DCM (2.0 mL). The reaction mixture was stirred at room temperature for 2 hours and was monitored by TLC. After completion of the reaction, the solvent was evaporated, and the crude was used directly in the CPG binding. The residual was dissolved in acetonitrile (3.0 mL), followed by the addition of TBTU (20 mg, 0.084 mmol), TEA (21 mg, 0.21 mmol), and 1000 Å CPG (0.60 g). The reaction was allowed to proceed under 25 degrees Celsius for two hours. The mixture was then filtered, washed with acetonitrile (3×3.0 mL), THF (3×3.0 mL), MTBE (3×3.0 mL), and dried to afford the uncapped CPG product. The dried uncapped CPG product was dispersed in THF (3.0 mL), followed by the addition of pyridine (0.12 mL), N-methylimidazole (0.12 mL) and acetic anhydride (0.12 mL). The mixture was allowed to rotate on a rotovap for 1 hour. It was then filtered, washed with THF (3×3 ml), 10% pyridine in EtOH (3×3.0 mL), EtOH (3×3.0 mL), ACN (3×3.0 mL), MTBE (3×3.0 mL), and dried to afford the capped CPG product 20. Loading was determined by standard DMTr assay by UV-Vis (498 nm) to be 20 mol/g.

Example 7. Preparation of DMT-dU-click-PEG-GalNAc-Phosphoramidite/CPG

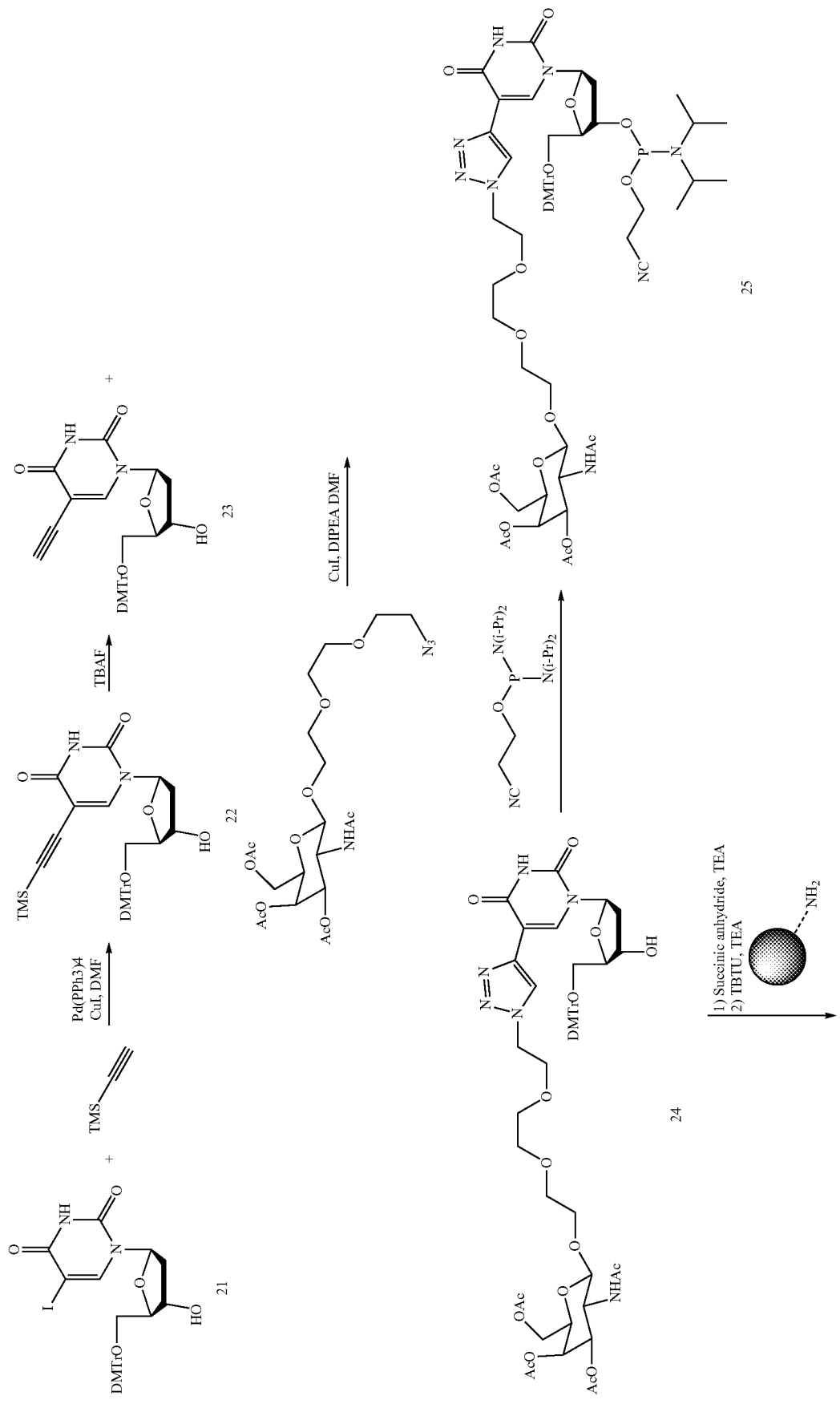

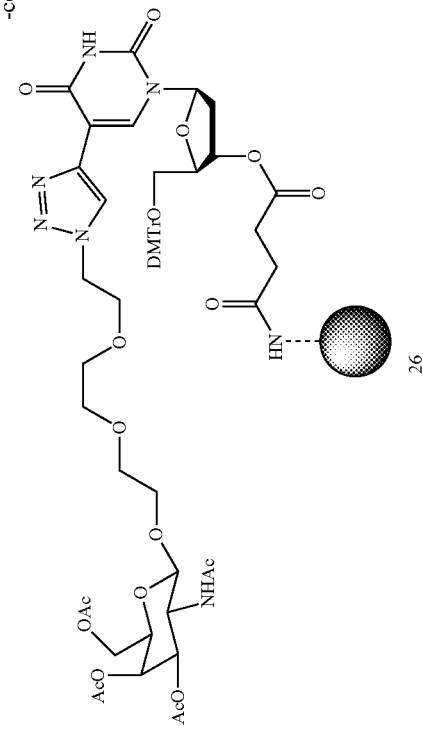

Compound 21 (5'-DMT protected-2'-deoxy-5-iodouridine) (2.8 g, 4.27 mmol), TMS-acetylene (784 mg, 8.0 mmol), Pd(PPh3)4 (280 mg, 0.24 mmol), CuI (73 mg, 0.38 mmol) and triethylamine (1.4 mL, 10 mmol) was dispersed in DMF (30 mL). The reaction mixture was purged with nitrogen and stirred at room temperature for 2 days. The reaction was monitored by HPLC. After completion, the mixture was filtered. The solution was diluted with ethyl acetate (50 mL) and washed with water (3×50 mL) and brine (50 mL). The organic layer was dried over sodium sulfate, filtered, and concentrated. The crude was subjected to flash column purification with DCM/MeOH (0% to 10% MeOH) to afford compound 22 (2.0 g, 75% yield) as a black solid. MS calc: [M−H]=625.24, found [M−H]=625.8.

Compound 22 (200 mg, 0.32 mmol) was dissolved in THF (3.0 mL), followed by the addition of TBAF (1 mmol, 1.0 mL, 1 M solution in THF). The reaction was monitored by TLC. The mixture was concentrated and subjected to flash column purification with DCM/MeOH (0% to 15% MeOH) to afford compound 23 (169 mg, 95% yield) as a brown oil. MS calc: [M−H]=553.21, found [M−H]=553.6.

Compound 23 (1.0 g, 1.8 mmol), GalNAc-PEG2-azide (1.9 g, 3.77 mmol), CuI (10 mg, 0.053 mmol) and DIPEA (0.8 ml, 4.6 mmol) was dispersed in DMF (15 mL). The reaction was stirred at room temperature for 3 days and was monitored by HPLC. The mixture was then concentrated and subjected to flash column purification with DCM/MeOH (0% to 15% MeOH) to afford compound 24 (387 mg, 20% yield) as a black oil. MS calc: [M−H]=1058.07, found [M−H]=1058.0.

Compound 24 (300 mg, 0.28 mmol), 2-cyanoethyl tetraisopropylphosphorodiamidite (171 mg, 0.57 mmol), and diisoropyl ammonium tetrazolide (12 mg, 0.071 mmol) was dispersed in DCM (5.0 mL). The reaction mixture was purged with nitrogen and was stirred at room temperature overnight. The reaction mixture was monitored by TLC. After completion, the mixture was washed with water (3×5.0 mL) and brine (5.0 mL). The organic layer was dried over sodium sulfate, filtered, and concentrated. The residual was redissolved in acetonitrile (5.0 mL) and washed with heptane (3×5 mL). The solvents were evaporated. The crude was subjected to flash column purification with DCM/TEA (4% TEA) to afford phosphoramidate product 25 (113 mg, 32% yield) as a white solid. MS calc: [M−H]=1258.30, found [M−H]=1258.2. $^{31}$PNMR (mixture of diastereomers, DMSO-$d_6$): δ 147.465, 147.076.

Compound 24 (87 mg, 0.082 mmol), succinic anhydride (12.3 mg, 0.123 mmol), and triethylamine (41.5 mg, 0.411 mmol) was dissolved in DCM (2.0 mL). The solution was stirred at room temperature for 1 day and was monitored by TLC. After completion, the solvent was evaporated, and the crude was used directly in the CPG binding. The residual was dissolved in acetonitrile (3.0 mL), followed by the addition of TBTU (52.6 mg, 0.164 mmol), TEA (33 mg, 0.33 mmol), and 1000 Å CPG (0.70 g). The reaction was allowed to proceed at 25 degrees Celsius for two hours. The mixture was then filtered, washed with acetonitrile (3×3.0 mL), THF (3×3.0 mL), MTBE (3×3.0 mL), and dried to afford the uncapped CPG product. The dried uncapped CPG product was dispersed in THF (3.0 mL), followed by the addition of pyridine (0.14 mL), N-methylimidazole (0.14 mL) and acetic anhydride (0.14 mL). The mixture was allowed to rotate on a rotovap for 1 hour, and it was then filtered, washed with THF (3×3.0 mL), 10% pyridine in EtOH (3×3.0 mL), EtOH (3×3.0 mL), ACN (3×3.0 mL), MTBE (3×3.0 mL), and dried to afford the capped CPG product 26. Loading was determined by standard DMTr assay by UV-Vis (498 nm) to be 31 mol/g.

Example 8. Preparation of DMT-dANHBz-click-PEG-GalNAc-Phosphoramidite/CPG

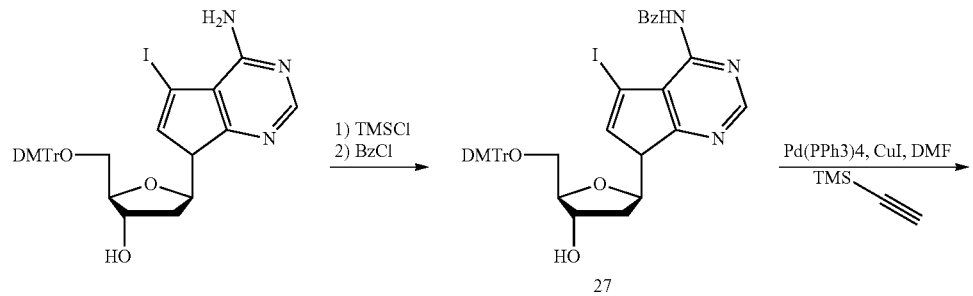

27

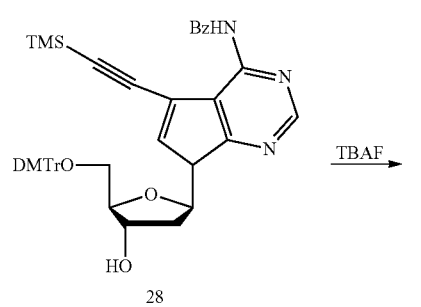

28

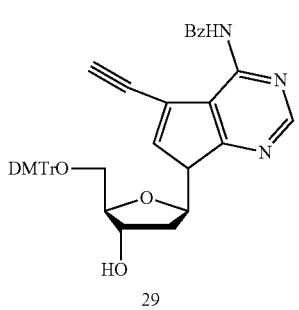
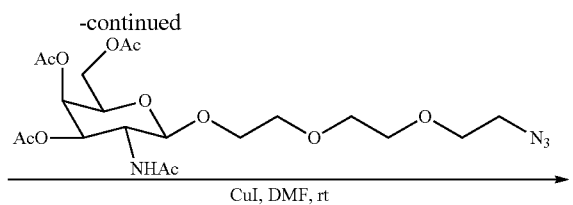

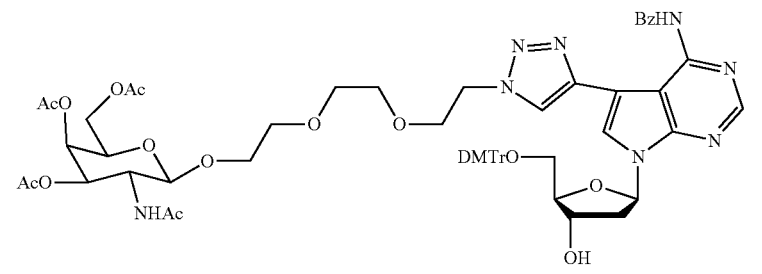

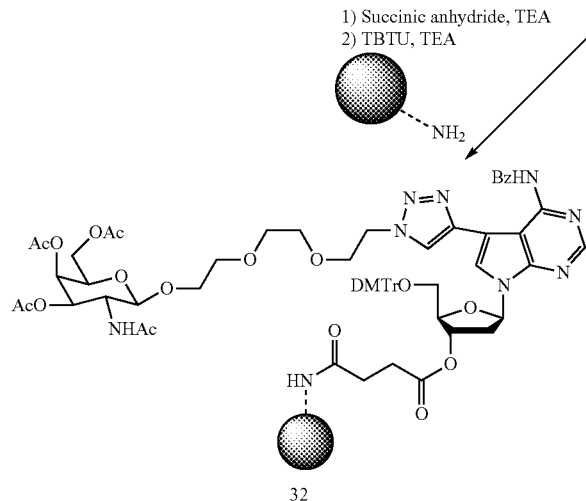
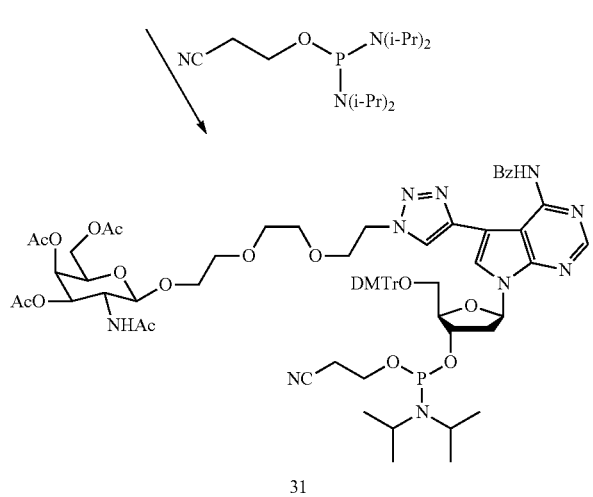

5′-DMT protected-7-deaza-2′-deoxy-7-isodoadenosine (3.3 g, 4.87 mmol) was dissolved in 50 ml pyridine. The solution was cooled with an ice bath, and TMSCl (9.6 ml, 49.1 mmol) was added dropwise. The reaction was allowed to warm up to room temperature for half an hour. And then the mixture was cooled again with an ice bath, followed by the addition of BzCl (0.62 ml, 3.47 mmol). After an hour, the reaction was quenched by adding water (10 mL). The organic solvents were evaporated, and the residual was diluted with ethyl acetate (50 mL), and washed with water (3×50 mL) and brine (50 mL). The organic layer was dried over sodium sulfate, filtered, and concentrated. The crude was subjected to flash column purification with DCM/MeOH (0% to 10% to afford compound 27 (3.0 g, 79% yield) as a white solid. MS calc: [M+H]=783.16, found [M+H]=783.6.

Compound 27 (0.9 g, 1.15 mmol), TMS-acetylene (225 mg, 2.3 mmol), Pd(PPh₃)₄ (260 mg, 0.23 mmol), CuI (44 mg, 0.23 mmol) and triethylamine (0.48 ml, 3.45 mmol) was dispersed in DMF (10 mL). The reaction mixture was purged with nitrogen and was stirred for 3 days. The reaction was monitored by TLC. After completion of the reaction, DMF was evaporated, and the crude was subjected to flash column purification with DCM/MeOH (0% to 10% MeOH) to afford compound 28 (843 mg, 98% yield) as a brown oil. MS calc: [M+H]=753.30, found [M+H]=753.6.

Compound 28 (843 mg, 1.13 mmol) was dissolved in THF (10 mL), followed by the addition of TBAF (3 mmol, 3.0 mL, 1M solution in THF). The reaction was monitored by TLC. The mixture was concentrated and subjected to flash column purification with DCM/MeOH (0% to 15% MeOH) to afford compound 29 (714 mg, 93% yield) as a brown oil. MS calc: [M+H]=681.26, found [M+H]=681.6.

Compound 29 (714 mg, 1.05 mmol), GalNAc-PEG3-azide (1.1 g, 2.2 mmol), CuI (21 mg, 0.11 mmol) and DIPEA (710 mg, 5.5 mmol) was dispersed in DMF (15 mL). The reaction was stirred at room temperature for 1 day and was monitored by LC-MS. The mixture was concentrated and subjected to flash column purification with DCM/MeOH (0% to 15% MeOH) to afford compound 30 (1.33 g, 107% yield) as a black solid. MS calc: [M+H]=1185.47, found [M+H]=1185.9.

Compound 30 (546 mg, 0.46 mmol), 2-cyanoethyl tetraisopropylphosphorodiamidite (278 mg, 0.92 mmol), and diisoropyl ammonium tetrazolide (20 mg, 0.115 mmol) was dispersed in DCM (5.0 mL). The reaction was purged with nitrogen and was stirred at room temperature overnight. The reaction was monitored by TLC. After completion, the mixture was washed with water (3×5.0 mL) and brine (5.0 mL). The organic layer was dried over sodium sulfate, filtered, and concentrated. The residual was redissolved in acetonitrile (5.0 mL) and washed with heptane (3×5.0 mL). The solvents were evaporated. The crude was subjected to flash column purification with DCM/TEA (4% TEA) to afford compound 31 (110 mg, 17% yield) as a brown oil. MS calc: [M+H]=1386.58, found [M+H]=1386.4. $^{31}$PNMR (mixture of diastereomers, DMSO-d$_6$): δ 149.603, 149.367.

Compound 30 (87 mg, 0.074 mmol), succinic anhydride (11 mg, 0.11 mmol), and triethylamine (37 mg, 0.37 mmol) was dissolved in DCM (2.0 mL). The solution was stirred for 1 day and was monitored by TLC. After completion of the reaction, the solvent was evaporated, and the crude was used directly in the CPG binding. The residual was dissolved in acetonitrile (3.0 mL), followed by the addition of TBTU (48 mg, 0.15 mmol), TEA (23 mg, 0.225 mmol), and 1000 Å CPG (0.70 g). The reaction was allowed to proceed at 25 degrees Celsius for two hours. The mixture was then filtered, washed with acetonitrile (3×3.0 mL), THF (3×3 mL), MTBE (3×3.0 mL), and dried to afford the uncapped CPG product. The dried uncapped CPG product was dispersed in THF (3.0 mL), followed by the addition of pyridine (0.14 mL), N-methylimidazole (0.14 mL) and acetic anhydride (0.14 mL). The mixture was allowed to rotate on a rotovap for 1 hour. Then it was filtered, washed with THF (3×3.0 mL), 10% pyridine in EtOH (3×3.0 mL), EtOH (3×3 mL), ACN (3×3.0 mL), MTBE (3×3.0 mL), and dried to afford the capped CPG product 32. Loading was determined by standard DMTr assay by UV-Vis (498 nm) to be 31 μmol/g.

Example 9. Preparation of GalNAc Linker Compound 33

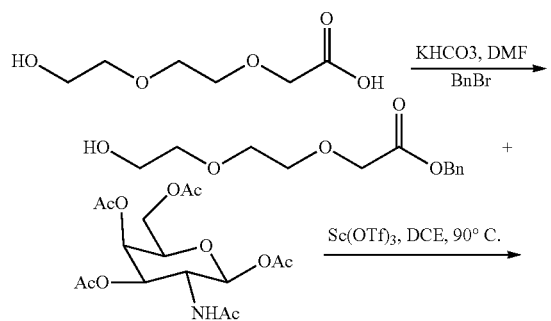

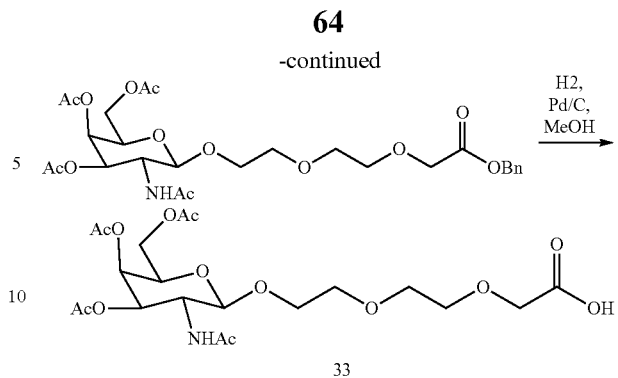

Step 1: HO-PEG2-CH$_2$CO$_2$H (5.0 g, 30.5 mmol) and KHCO$_3$ (3.65 g, 36.5 mmol) were dissolved in DMF (61.0 mL) in a round bottom flask with stirring. Benzyl bromide (4.35 mL, 36.5 mmol) was added dropwise, and the reaction mixture was allowed to stir at r.t. overnight. Volatile was removed in vacuo, and the residual was dissolved in DCM. Precipitates were removed by filtration, and the filtrate was concentrated. The crude material was purified by silica column (eluent: 0-15% MeOH in DCM). Pure fractions were collected and concentrated to dryness under vacuum to obtain an oil (4.02 g, 51.9% yield). MS: found: [M+H]=255.4; calc: [M+H]=255.1.

Step 2: The above oil (4.02 g, 15.8 mmol) and peracylated GalNAc (4.10 g, 10.5 mmol) were dissolved in DCE (40.4 mL). Sc(OTf)$_3$ (0.36 g, 0.74 mmol) was then added. The reaction mixture was heated to 90° C. overnight. The reaction mixture was cooled to r.t and poured into saturated NaHCO3 (50 mL) with vigorous stirring. The organic layer was separated and the aqueous phase was extracted with DCM (2×50 mL). The combined organic phase was dried over Na$_2$SO$_4$, filtered and concentrated to dryness. The crude material was purified by normal phase silica column (eluent: 0 to 10% MeOH in DCM). Fractions were collected and concentrated to dryness under vacuum to obtain yellow oil (7.23 g, 118% yield). MS: found: [M+H]=584.4; calc: [M+H]=584.2.

Step 3: The product from step 2 was dissolved in MeOH (62 mL), and 10% Pd/C (200 mg, 1.86 mmol) under Ar purge. Air was removed under vacuum and H$_2$ balloon was inserted. The reaction mixture was stirred at r.t for 2 h and was filtered through a celite pad. The pad was washed the with MeOH twice, and the volatile was removed in vacuo. The crude material was purified by C18 reversed phase column (eluent: 0-90% MeCN in water). The pure fractions were collected and concentrated to dryness under vacuum to obtain Compound 33 an oil (3.72 g, 71.8% yield). MS: found: [M−H]=492.4; calc: [M−H]=492.2.

Example 10. Preparation of GalNAc-conjugated uridine-EG-CPG Compounds

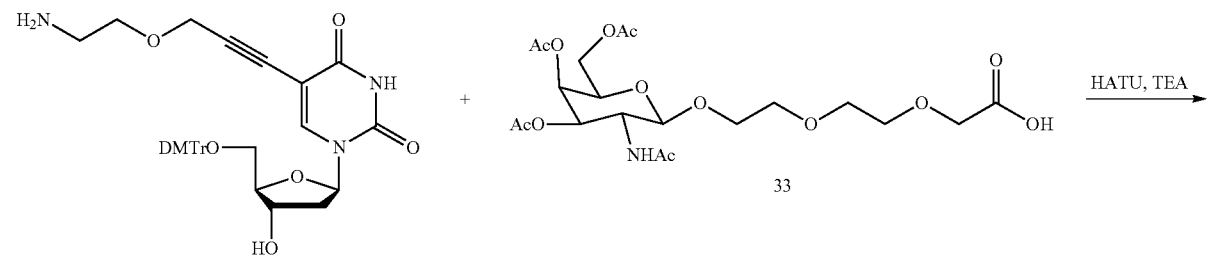

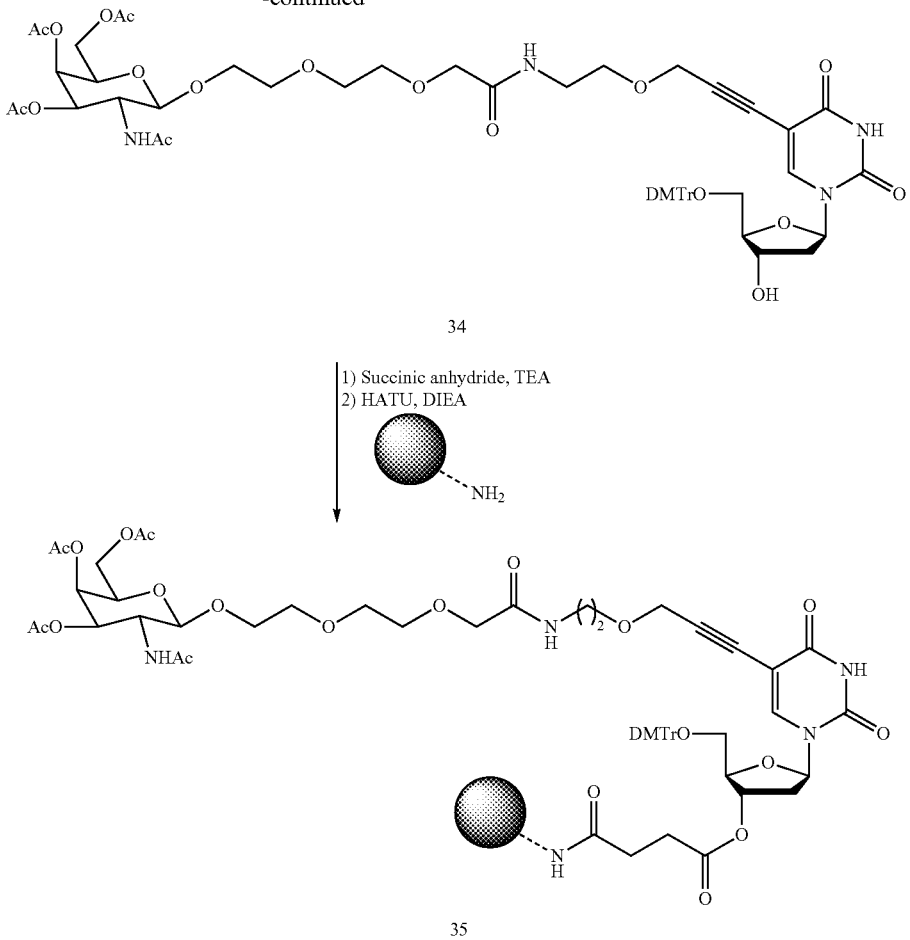

Compound 7 (0.60 g, 0.96 mmol) and compound 33 (0.52 g, 1.05 mmol) were dissolved in DCE (2.4 mL). TEA (0.66 mL, 4.78 mmol) and HATU (0.4 g, 1.05 mmol) were added. The reaction was allowed to stir at r.t. overnight. Upon completion of the reaction, the solvent was removed and the crude was purified by reversed phase column purification using H$_2$O/MeCN. The pure fractions were collected and concentrated to dryness under vacuum to obtain 290 mg of compound 5 in 30.5% yield. MS: found: [M−H]=1101.9; calc: [M−H]=1101.4.

Preparation of GalNAc-conjugated uridine-EG-CPG compounds—Step 1: In one 50 mL RB flask, Compound 34 (290 mg, 0.263 mmol) was dissolved in DCM (10 mL). Succinic anhydride (39.5 mg, 0.395 mmol), TEA (79.7 mg. 0.798 mmol) were added. The reaction mixture was stirred at room temperature for 2 hours. Completion of the reaction was confirmed by TLC. This mixture was then poured into saturated NaHCO$_3$ (15 mL), DCM (40 mL) was added and the organic layer was separated, washed with water, brine and dried over Na$_2$SO$_4$. After filtration, the organic layer was concentrated to dryness under vacuum. The crude product was purified by column purification using DCM/MeOH (0% to 10% MeOH). The pure fractions were collected and concentrated to dryness under vacuum to obtain 200 mg white solid in 63% yields. MS: found: [M−H]=1201.6; calc: [M−H]=1201.4.

Step 2: In one 50 mL R$_B$ flask, compound from step 1 (43 mg, 0.036 mmol) was dissolved MeCN (5 mL). HATU (13 mg, 0.036 mmol), DIEA (14 mg, 0.019 mmol) were added. After 5 min, CPG (1.0 g) was added. The reaction mixture was stirred at room temperature for 3 hours. After filtration, this CPG product was washed with MeCN (3×50 mL) and THF (3×50 mL), and then dried under vacuum. Capping A reagent: (THF/acetic anhydride/pyridine 80/10/10 v/v/v, 5 mL) and Capping B reagent: (1-methylimidazole/THF, 16/84, v/v, 5 mL) were added into the flask, and the mixture was stirred for 2 hours at room temperature. After filtration, the CPG product 35 (after caping) was washed by EtOH (50 mL×3), EtOH/Pyridine(10%) (50 mL×3), THF(50 mL×3) and DCM(50 mL×3). The CPG (after caping) was dried under vacuum. Loading was determined by standard DMTr assay by UV-Vis (498 nm) to be 39 μg/mol.

Example 11. Usage of GalNAc-conjugated Phosphoramidites in Oligonucleotide Synthesis To demonstrate the usage of novel GalNAc-conjugated phosphoramidites in oligonucleotide synthesis, a sequence was designed for trials: 5'-X-TTTTTTTTTT-3', where X represents GalNAc-conjugated phosphoramidites. The following sequences were generated: Seq X1.1, Seq X1.2, Seq X2, Seq X3, and Seq X4.

Oligonucleotides (Seq X1.1 through X4) were synthesized by solid-phase phosphoramidite method. A DMT-dT solid support was packed in an empty column and put into the MerMade 6 synthesizer. The synthetic scale is 0.5-1

µmol. The oligonucleotide synthesis cycle includes the following steps: (1) detritylation with 3% trichloroacetic acid in dichloromethane for 45 seconds two times, followed by acetonitrile washing; (2) coupling with 0.1 M DMT-dT-CE-Phosphoramidite (5'—O—(4, 4'-Dimethoxytrityl)-thymidine-3'-cyanoethyl Phosphoramidite) in acetonitrile and 0.5 M activator (tetrazole in acetonitrile) for 1 minute two times, followed by acetonitrile washing; (3) oxidation with iodine (0.015 M iodine in water/pyridine/THF 2/20/78) for 45 second, followed by acetonitrile washing; and (4) capping with a mixture of acetic anhydride, pyridine, and THF for 45 second, followed by acetonitrile washing. Steps (1)-(4) were repeated 9 times for synthesizing a T10 elongated from the dT solid support. The final cycle to couple novel GalNAc-conjugated phosphoramidites includes the sample detritylation, oxidation, and capping step, while the coupling is using a mixture of 0.05 M novel GalNAc-conjugated phosphoramidites in acetonitrile and 0.5 M activator for 3 minutes for two times, followed by acetonitrile washing.

After synthesis, the oligonucleotide-bounded solid supports were treated with a 1:1 mixture of aqueous ammonia hydroxide and methylamine at 55° C. for 2 hours for cleavage and deprotection. Upon completion, the liquid phase was collected and heat dried in vacuum. The dried residue was dissolved in water and analyzed by reverse-phase HPLC (Agilent 1260) and LC-MS (Applied Biosystems 4000 Q-Trap). The HPLC gradient was 30-70% B in 20 min, with A: 50 mM triethylammonium acetate in water and B: 80% 50 mM triethylammonium acetate in water and 20% acetonitrile. The retention time (RT), MS calculated, MS found, and full-length product purity (FLP) for each sequence (Seq X1.1-X4) were listed in Table 1.

TABLE 1

Usage tests of GalNAc-conjugated phosphoramidites

| Oligo-nucleotides | X (Phosphoramidite) | RT (min) | MS Calculated | MS Found | FT (%) |
|---|---|---|---|---|---|
| Seq X1.1 | dA-EO-compound 14 | 12.342 | 3693.3 | 3694.5 | 13.19 |
| Seq X1.2 | dA(Bz)-EO-compound 19 | 12.171 | 3693.3 | 3693.3 | 13.71 |
| Seq X2 | dU-EO-compound 9 | 11.241 | 3671.2 | 3671.3 | 14.00 |
| Seq X3 | dA(Bz)-click-PEG-compound 31 | 12.456 | 3695.3 | 3696.8 | 24.83 |
| Seq X4 | dU-click-PEG-compound 25 | 10.26 | 3673.2 | 3675.3 | 14.87 |

FT: Functional Test percentage (coupling efficiency)

Example 12: Usage of GalNAc-conjugated Solid Supports in Oligonucleotide Synthesis To demonstrate the usage of novel GalNAc-conjugated solid supports in oligonucleotide synthesis, a sequence was designed for trails: 5'-TTTTTTTTTT-Y-3', where Y represents GalNAc-conjugated solid supports. The following sequences were generated: Seq Y1, Seq Y2, Seq Y3, Seq Y4, and Seq Y5.

Oligonucleotides (Seq Y1-Y5) were synthesized by solid-phase phosphoramidite method. A novel DMT-GalNAc conjugated solid support (Y) was packed in an empty column and put into the MerMade 6 synthesizer. The synthetic scale is 0.5-1 µmol. The oligonucleotide synthesis cycle includes the following steps:(1) detritylation with 3% trichloroacetic acid in dichloromethane for 45 seconds two times, followed by acetonitrile washing; (2) coupling with 0.1 M DMT-dT-CE-Phosphoramidite (5'—O—(4, 4'-Dimethoxytrityl)-thymidine-3'-cyanoethyl Phosphoramidite) in acetonitrile and 0.5 M activator (tetrazole in acetonitrile) for 1 minute two times, followed by acetonitrile washing; (3) oxidation with iodine (0.015 M iodine in water/pyridine/THF 2/20/78) for 45 second, followed by acetonitrile washing; and (4) capping with a mixture of acetic anhydride, pyridine, and THF for 45 second, followed by acetonitrile washing. Steps (1)-(4) were repeated 10 times for synthesizing a T10 elongated from the GalNAc conjugated solid support and finished by the final detritylation with acetonitrile washing.

After synthesis, the oligonucleotide-bounded solid supports were treated with a 1:1 mixture of aqueous ammonia hydroxide and methylamine at 55° C. for 2 hr for cleavage and deprotection. Upon completion, the liquid phase was collected and heat dried in vacuum. The dried residue was dissolved in water and analyzed by reverse-phase HPLC (Agilent 1260) and LC-MS (Applied Biosystems 4000 Q-Trap). The HPLC gradient was 30-70% B in 20 min, with A: 50 mM triethylammonium acetate in water and B: 80% 50 mM triethylammonium acetate in water and 20% acetonitrile. The retention time (RT), MS calculated, MS found, and full-length product purity (FLP) for each sequence (Seq Y1-Y5) were listed in Table 2.

TABLE 2

Usage tests of GalNAc-conjugated solid supports

| Oligo-nucleotides | Y (CPG) | RT (min) | MS Calculated | MS Found | FLPY (%) |
|---|---|---|---|---|---|
| Seq Y1 | dA(Bz)-EO-compound 20 | 12.207 | 3693.3 | 3693.3 | 83.13 |
| Seq Y2 | dU-EO-compound 10 | 13.493 | 3671.2 | 3672.2 | 53.70 |
| Seq Y3 | dA(Bz)-click-PEG-compound 32 | 11.701 | 3695.3 | 3694.9 | 81.39 |
| Seq Y4 | dU-click-PEG-compound 26 | 10.583 | 3673.2 | 3674.4 | 42.93 |
| Seq Y5 | dU-PEG-compound 35 | 9.993 | 3717.2 | 3713.3 | 23.64 |

FLPY: Full Length Product Yield

While the present application has been described with reference to the specific embodiments thereof, it should be understood by those skilled in the art that various changes may be made and equivalents may be substituted without departing from the true spirit and scope of the present application. In addition, many modifications may be made to adapt a particular situation, material, composition of matter, process, process step or steps, to the objective, spirit and scope of the present application. All such modifications are intended to be within the scope of the claims appended hereto.

What is claimed is:

1. A compound of Formula (I):

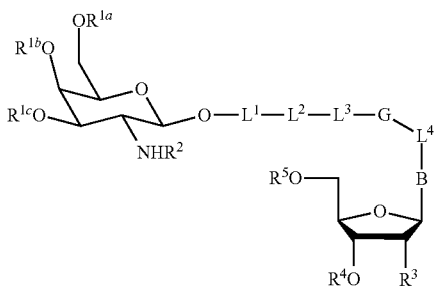

(I)

or a pharmaceutically acceptable salt thereof, wherein each of $R^{1a}$, $R^{1b}$ and $R^{1c}$ is independently hydrogen, benzyl (Bn), or —C(=O)$R^{1A}$;

$R^2$ is —C(=O)$C_{1-6}$ alkyl, —C(=O)$C_{1-6}$ haloalkyl or —C(=O)phenyl;

$R^3$ is hydrogen, halo, hydroxy, $C_{1-6}$ alkoxy, $C_{1-6}$ haloalkoxy, $C_{1-6}$ alkyl, $C_{1-6}$ haloalkyl, ($C_{1-6}$ alkoxy)$C_{1-6}$ alkyl, —O—($C_{1-6}$ alkoxy)$C_{1-6}$ alkyl, or a protected hydroxy group;

$R^4$ is hydrogen, a phosphoramidite moiety, —C(=O)CH$_2$CH$_2$C(=O)$R^{4A}$, or —P(O$R^{4B}$)N$R^{4C}R^{4D}$;

$R^5$ is a hydroxy protecting group;

each of $L^1$, $L^2$, and $L^3$ is independently a bond, —C(=O)—, —C(=S)—, —S(=O)$_2$—, —C(=O)N$R^6$—, —C(=S)N$R^6$—, —C(=O)O—, —C(=S)O—, —N$R^6$C(=O)N$R^6$—, —N$R^6$C(=S)N$R^6$—, —OP(=O)(OH)O—, —OP(=S)(OH)O—, —O—, —S—, —N$R^6$—, optionally substituted $C_{1-10}$ alkylene, optionally substituted $C_{6-10}$ arylene, optionally substituted $C_{3-10}$ cycloalkylene, optionally substituted 5-10 membered hetetroarylene, optionally substituted 5 to 10 membered heterocyclylene, or optionally substituted 2 to 15 membered heteroalkylene wherein one or more carbon atoms are replaced with C(=O), O, S or N, provided that at least one of $L^1$, $L^2$, and $L^3$ is not a bond;

G is

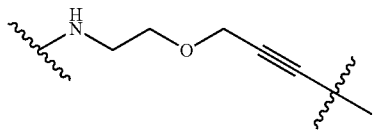 [SMILES: *C#CCOCCN*]

or triazolene optionally substituted with $R^7$;

$L^4$ is a bond, optionally substituted $C_{1-10}$ alkylene, or optionally substituted 2 to 15 membered heteroalkylene wherein one or more carbon atoms are replaced with C(=O), O, S or N;

B is a natural nucleobase, a modified natural nucleobase, or an unnatural nucleobase;

each $R^{1A}$ is independently $C_{1-6}$ alkyl, $C_{1-6}$ haloalkyl, or optionally substituted phenyl;

$R^{4A}$ is —OH, —O$R^8$ or —N$R^9R^{10}$;

each of $R^{4B}$, $R^{4C}$ and $R^{4D}$ is independently H, $C_{1-6}$ haloalkyl, or optionally substituted $C_{1-6}$ alkyl;

each $R^6$ is independently H or optionally substituted $C_{1-6}$ alkyl;

$R^7$ is independently halo, amino, hydroxy, $C_{1-6}$ alkyl, $C_{1-6}$ haloalkyl, $C_{1-6}$ alkoxy, $C_{1-6}$ haloalkoxy, ($C_{1-6}$ alkoxy) $C_{1-6}$ alkyl, or —O—($C_{1-6}$ alkoxy)$C_{1-6}$ alkyl;

$R^8$ is optionally substituted $C_{1-6}$ alkyl or a hydroxy protecting group; and each of $R^9$ and $R^{10}$ is independently H, optionally substituted $C_{1-6}$ alkyl or an amino protecting group.

2. The compound of claim 1, having the structure of Formula (Ia):

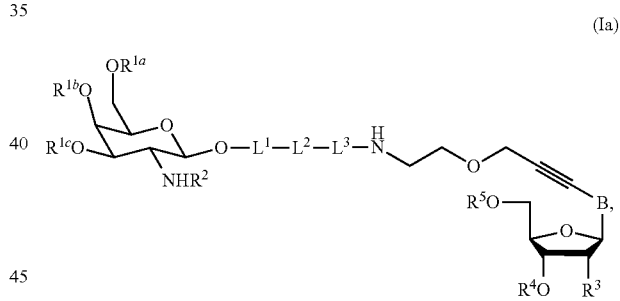

(Ia)

or a pharmaceutically acceptable salt thereof.

3. The compound of claim 1, having the structure of Formula (Ib):

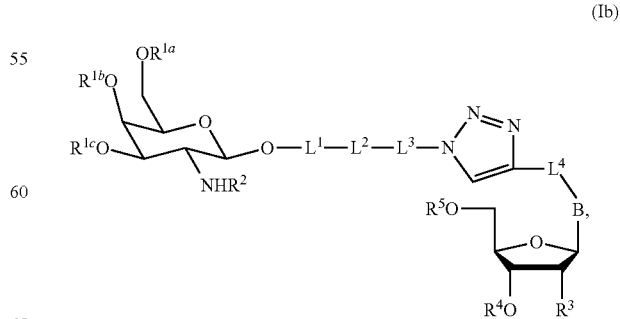

(Ib)

or a pharmaceutically acceptable salt thereof.

4. The compound of any one of claim 1, wherein B is:

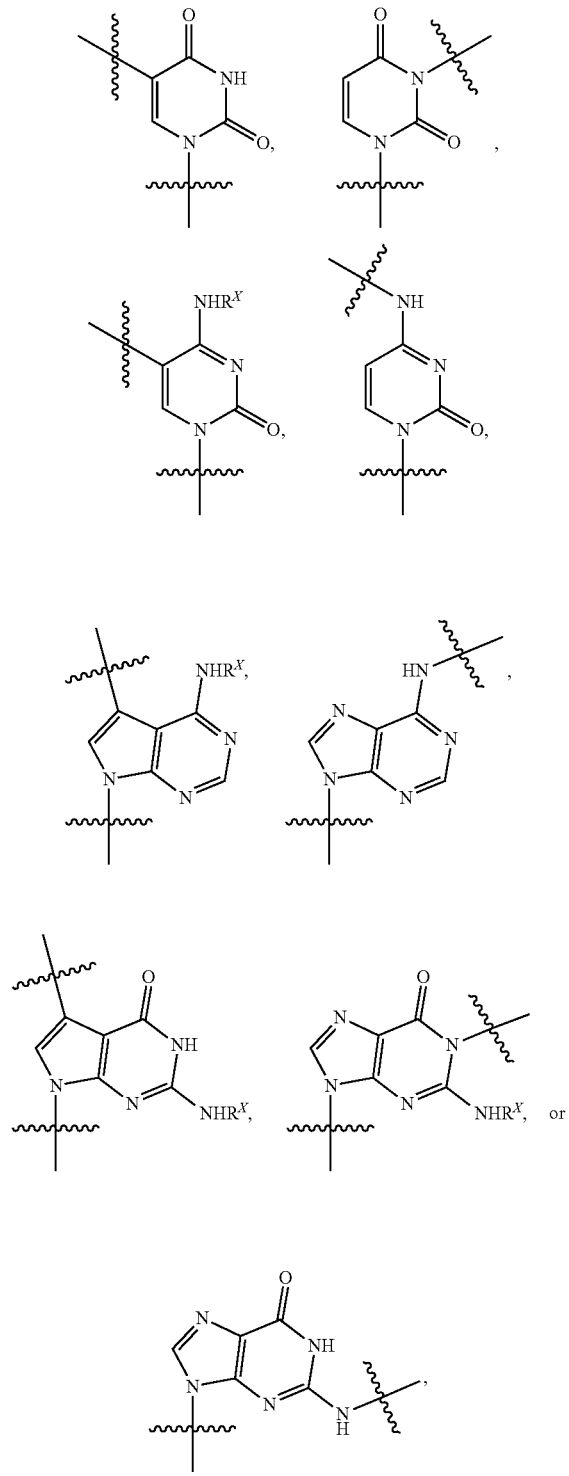

wherein $R^x$ is hydrogen or an amino protecting group, or the hydrogen in -NHR$^x$ is absent and $R^x$ is a divalent amino protecting group.

5. The compound of claim 4, wherein $R^x$ is —C(=O)C$_{1-6}$ alkyl or —C(=O)phenyl, or the hydrogen in -NHR$^x$ is absent and $R^x$ is 6. The compound of claim 5, wherein $R^x$ is —C(=O)CH$_3$ or —C(=O)CH(CH$_3$)$_2$.

7. The compound of claim 1, wherein each of $R^{1a}$, $R^{1b}$ and $R^{1c}$ is independently H, —C(=O)CH$_3$ or —C(=O)Ph.

8. The compound of claim 7, wherein each of $R^{1a}$, $R^{1b}$ and $R^{1c}$ is —C(=O)CH$_3$.

9. The compound of any claim 1, wherein $R^2$ is —C(=O)CH$_3$ or —C(=O)CF$_3$.

10. The compound of claim 1, wherein $R^3$ is H, —OH, —OCH$_3$, —F, —OCF$_3$, —OCH$_2$CH$_2$OCH$_3$, —O-tert-butyldimethylsilyl, or —O-tri-isopropylsilyloxymethyl.

11. The compound of claim 1, wherein $R^4$ is —C(=O)CH$_2$CH$_2$C(=O)OH.

12. The compound of claim 1, wherein $R^4$ is

13. The compound of claim 1, wherein $R^5$ is a trityl type of hydroxy protecting group selected from (4-methoxyphenyl)diphenylmethyl, bis(4-methoxyphenyl)phenylmethyl, tris(4-methoxyphenyl)methyl, 9-phenylxanthen-9-yl or 9-(4-methoxyphenyl)xanthen-9-yl.

14. The compound of claim 1, wherein $L^1$ is a bond, C$_{1-10}$ alkylene, or 2 to 15 membered heteroalkylene, wherein one or more carbon atoms are replaced with C(=O), O or N.

15. The compound of claim 1, wherein $L^2$ is —C(=O)—, —C(=O)NR$^6$—, —NR$^6$—, or 2 to 15 membered heteroalkylene, wherein one or more carbon atoms are replaced with C(=O), O or N, and wherein $R^6$ is H or CH$_3$.

16. The compound of claim 1, wherein $L^3$ is a bond or 2 to 15 membered heteroalkylene, wherein one or more carbon atoms are replaced with C(=O), O or N.

17. The compound of claim 1, wherein $L^1$-$L^2$-$L^3$ is —(CH$_2$)$_{2-6}$C(=O)—, —[(CH$_2$)$_2$O]$_{1-5}$—CH$_2$C(=O)—, or —[(CH$_2$)$_2$O](CH$_2$)$_{1-4}$—.

18. The compound of claim 1, wherein $L^4$ is a bond or C$_{1-10}$ alkylene.

19. The compound of claim 1, selected from the group consisting of:

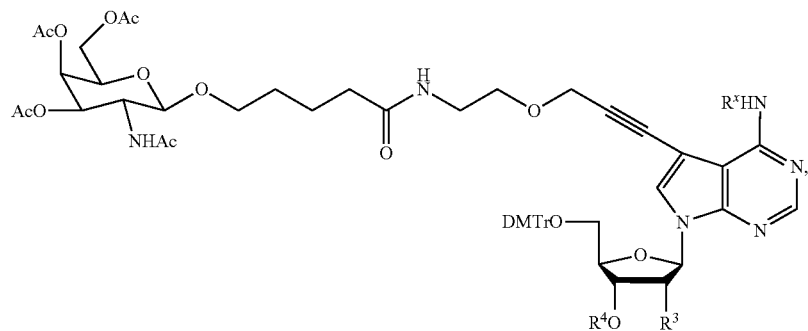
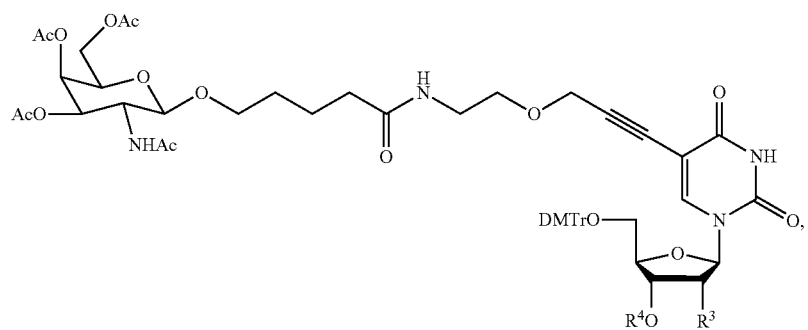
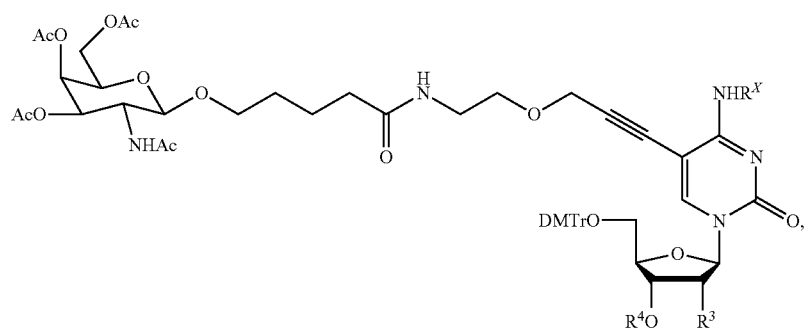
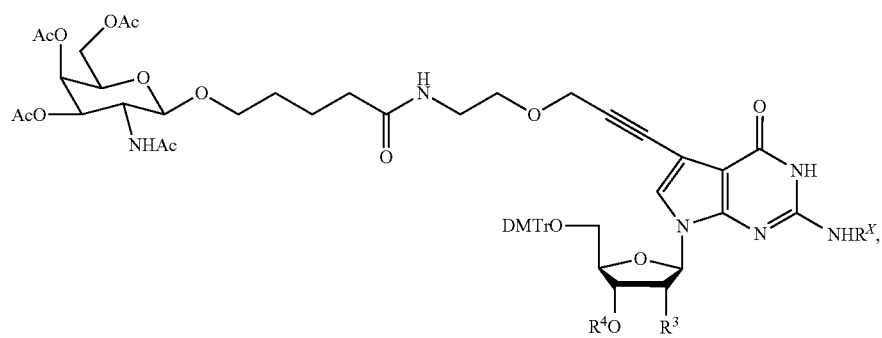
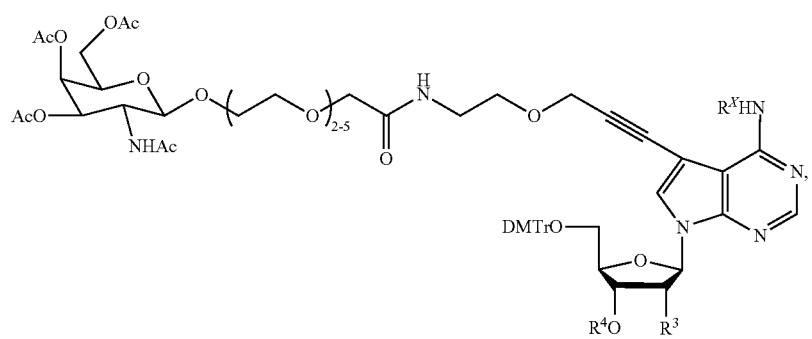

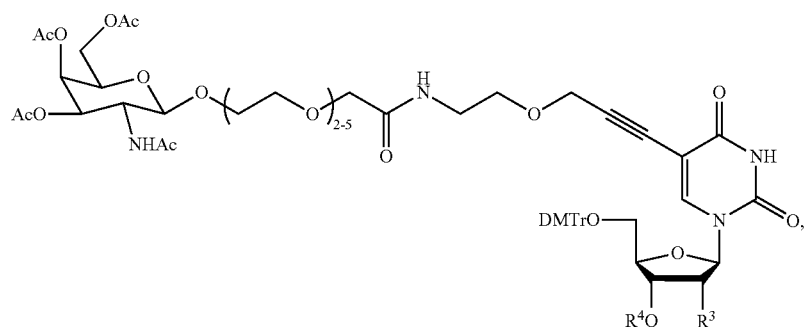
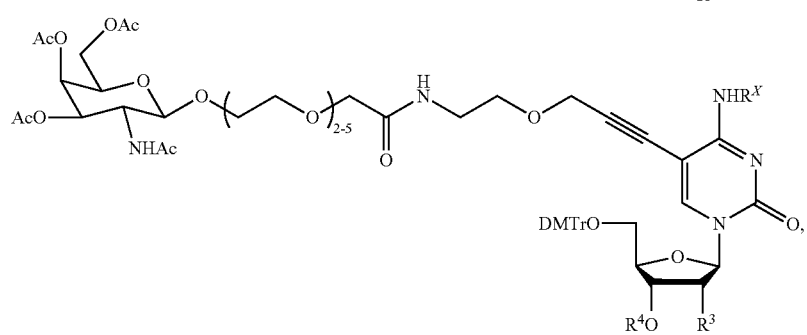
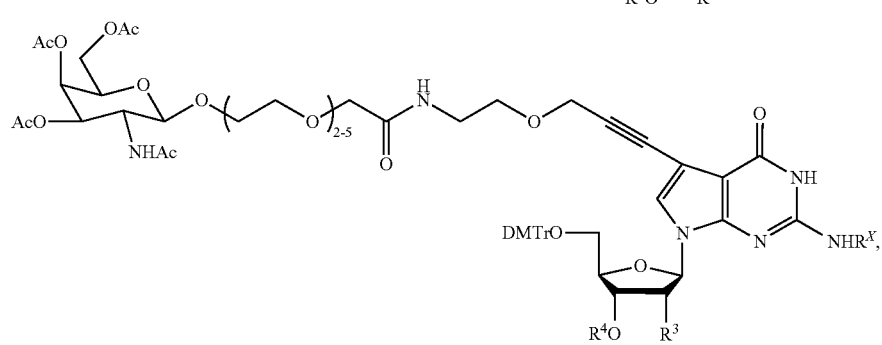
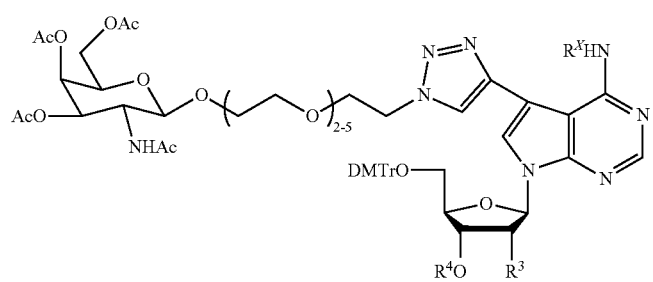
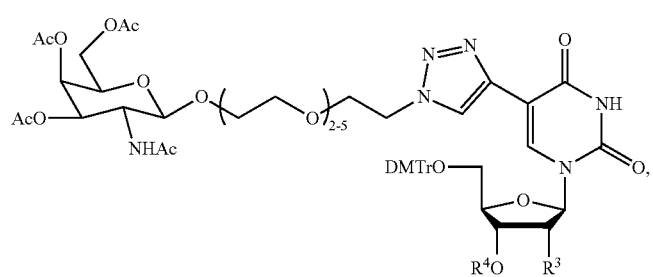

-continued

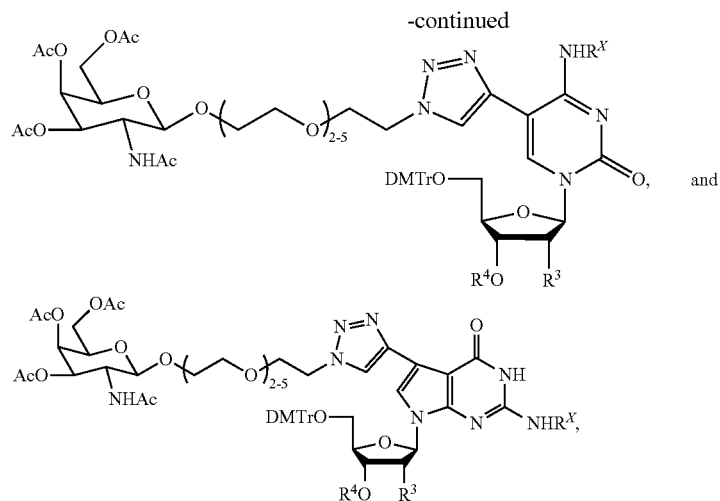

and pharmaceutically acceptable salts thereof;
wherein $R^3$ is H, —F, —OCH$_3$, —OCH$_2$CH$_2$OCH$_3$, —O-tertbutyldimethylsilyl or a protected hydroxy group;
each $R^x$ is independently H, —C(=O)CH$_3$, —C(=O)Ph, or —C(=O)CH(CH$_3$)$_2$; and
$R^4$ is —C(=O)CH$_2$CH$_2$C(=O)OH or

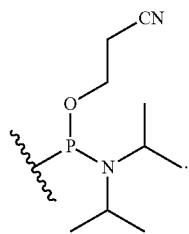 [SMILES: *P(OCCC#N)N(C(C)C)C(C)C]

20. A solid support comprising the compound of claim 1 covalently attached thereto via $R^4$ of the compound, wherein the compound is covalently attached via a moiety:

wherein the dashed line refers to the connection with the solid support, optionally through an additional linker, and wherein the squiggly line refers to the point of the attachment of the 3' oxygen of the compound to the remaining portion of the compound.

21. The solid support of claim 20, wherein the compound is incorporated into an oligonucleotide sequence.

22. A method of preparing a synthetic oligonucleotide, comprising reacting a compound of claim 1, with an oligonucleotide.

23. The method of claim 22, wherein the reaction is conducted on a solid support.

* * * * *

UNITED STATES PATENT AND TRADEMARK OFFICE
CERTIFICATE OF CORRECTION

| | | |
|---|---|---|
| PATENT NO. | : 11,649,260 B2 | Page 1 of 3 |
| APPLICATION NO. | : 17/842135 | |
| DATED | : May 16, 2023 | |
| INVENTOR(S) | : Xiaoyang Guan et al. | |

It is certified that error appears in the above-identified patent and that said Letters Patent is hereby corrected as shown below:

In the Drawings

Figure 4:
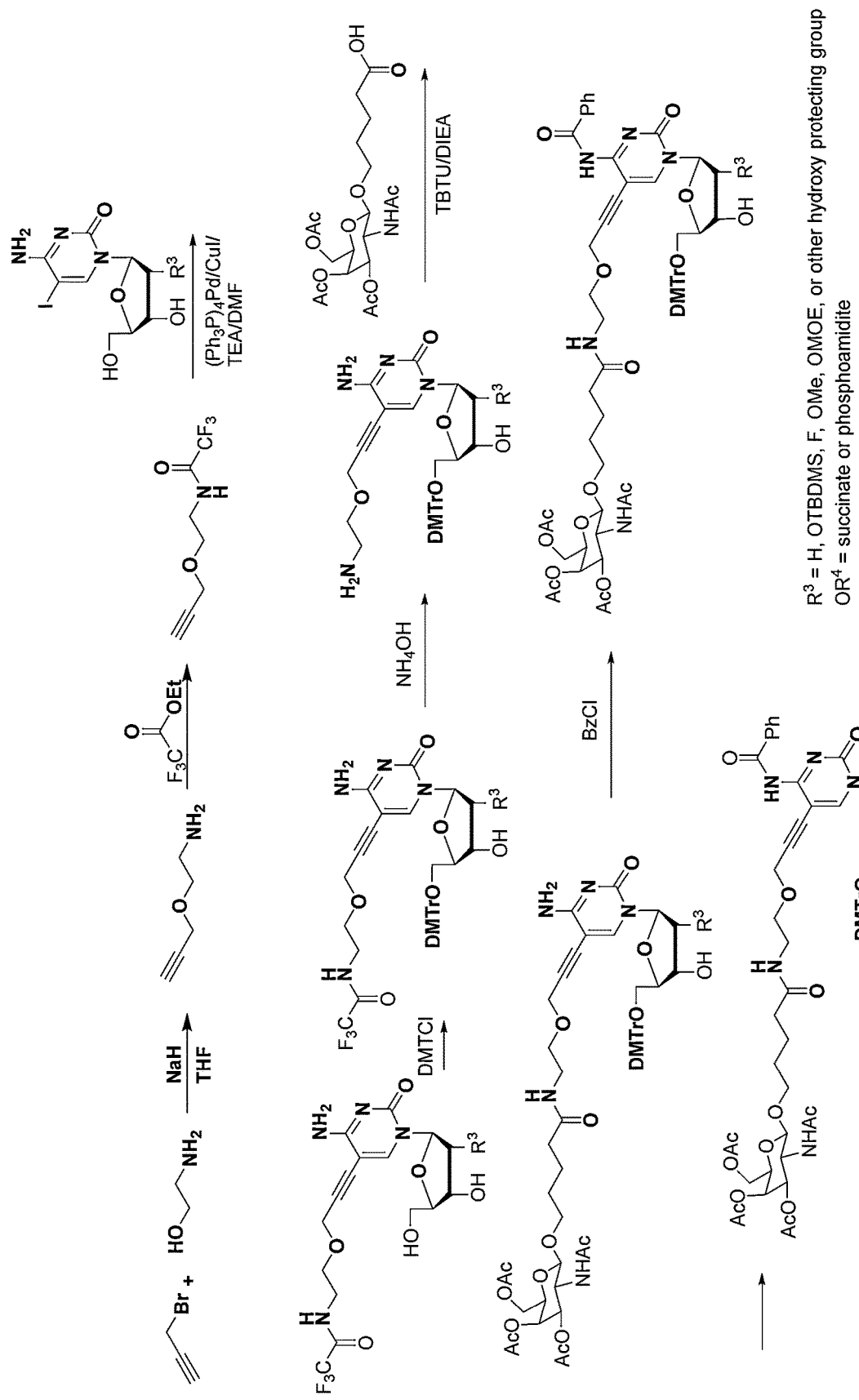
FIG. 4 is a reaction scheme for the conjugation of GalNAc with cytidine followed by subsequent formation of an —O-succinate or —O-phosphoramidite at the 3'-position according to an embodiment of the present application.

Sheet 4 of 6 (FIG. 4), Line 5 (approx.), delete "phosphoamidite" and insert -- phosphoramidite --.

Figure 5:
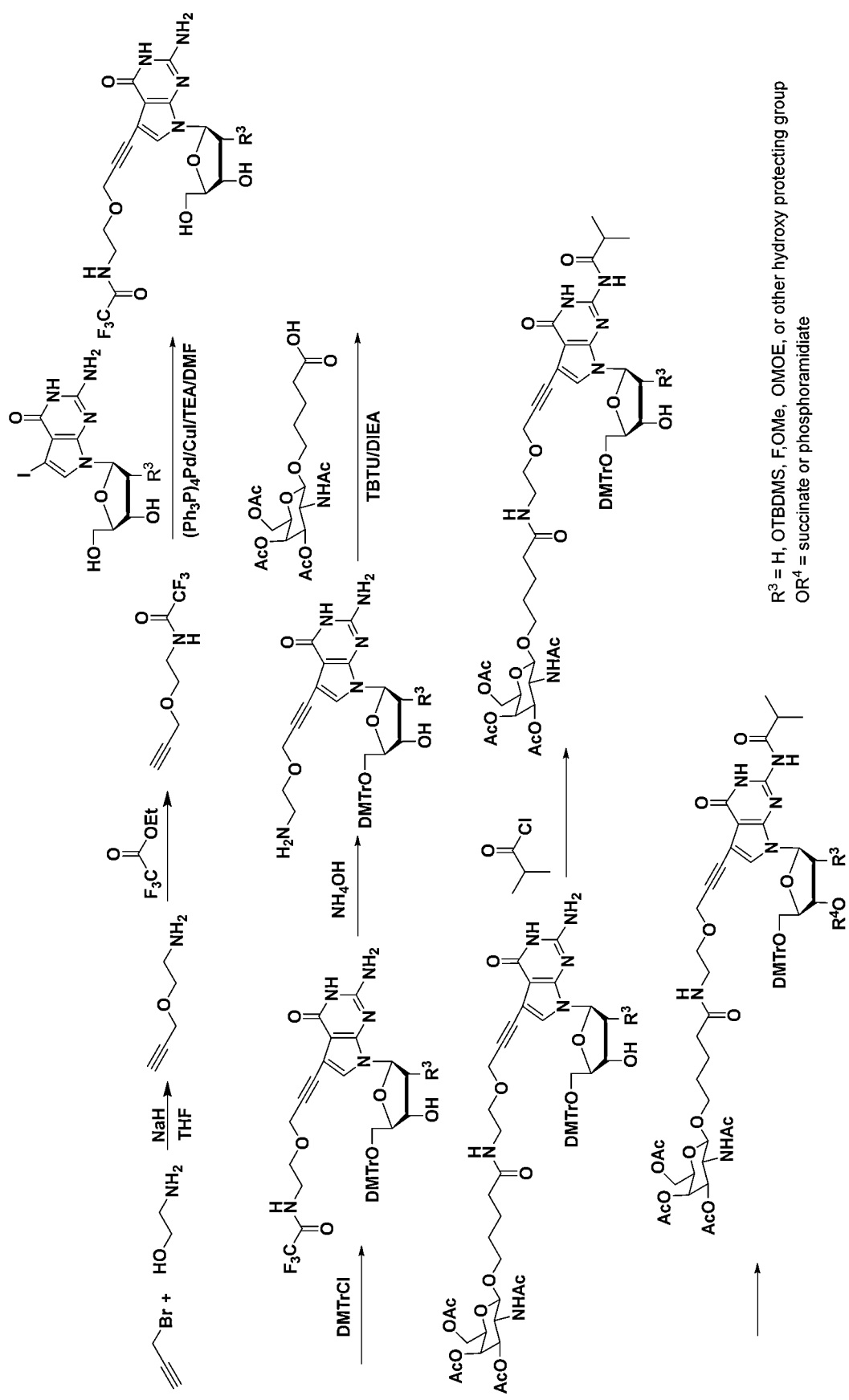
FIG. 5 is a reaction scheme for the conjugation of GalNAc with 7-deaza guanosine followed by subsequent formation of an —O-succinate or —O-phosphoramidite at the 3'-position according to an embodiment of the present application.

Sheet 5 of 6 (FIG. 5), Line 5 (approx.), delete "phosphoramidiate" and insert -- phosphoramidite --.

In the Specification

Column 2, Line 25, delete "dependently" and insert -- independently --.

Column 2, Line 45, delete "hetetroarylene," and insert -- heteroarylene, --.

Column 6, Line 15 (approx.), delete "$L^2$-$L^2$-$L^3$" and insert -- $L^1$-$L^2$-$L^3$ --.

Column 12, Line 59, delete "cyclalkynyl," and insert -- cycloalkynyl, --.

Column 15, Line 52, delete "benzoisoxazole," and insert -- benzisoxazole, --.

Column 16, Line 34, delete "hexahydro- 1,3 ,5-triazine," and insert -- hexahydro-1,3,5-triazine, --.

Column 16, Line 40, delete "thiamorpholine, thiamorpholine sulfoxide" and insert -- thiomorpholine, thiomorpholine sulfoxide --.

Column 16, Line 41, delete "thiamorpholine" and insert -- thiomorpholine --.

Column 17, Line 3, delete ""$C_2C_{10}$" and insert -- "$C_2$-$C_{10}$ --.

Column 18, Line 27, delete ""-$NRAR_B$"" and insert -- "-$NR_AR_B$" --.

Column 22, Line 23, delete "p-toluensulfonic" and insert -- p-toluenesulfonic --.

Signed and Sealed this
Third Day of October, 2023

*Katherine Kelly Vidal*

Katherine Kelly Vidal
*Director of the United States Patent and Trademark Office*

CERTIFICATE OF CORRECTION (continued)

Column 23, Line 56 (approx.), delete "and)" and insert -- and --.

Column 24, Line 58, delete "R$^{1a}$" and insert -- R$^{1A}$ --.

Column 25, Line 7, delete "(C$_{1-6\ alkoxy}$)C$_{1-6}$ alkyl," and insert -- (C$_{1-6}$ alkoxy)C$_{1-6}$ alkyl, --.

Column 25, Line 28, delete "embodimentcc," and insert -- embodiment, --.

Column 28, Line 1, delete "—S(=O)2—," and insert -- —S(=O)$_2$—, --.

Column 28, Line 44, delete "clyclalkylene)," and insert -- cycloalkylene), --.

Column 28, Line 45, delete "hetetroarylene" and insert -- heteroarylene --.

Column 43, Line 20, delete "the" and insert -- The --.

Column 43, Line 30, delete "2'deoxyuridine" and insert -- 2'-deoxyuridine --.

Column 43, Line 33, delete "2'deoxyuridine" and insert -- 2'-deoxyuridine --.

Column 44, Line 30, delete "N,N-diisopropylchlorophosphoramindite" and insert -- N,N-diisopropylchlorophosphoramidite --.

Column 47, Line 33 (approx.), delete "isodoadenosine" and insert -- iodoadenosine --.

Column 47, Line 35 (approx.), delete "isodoadenosine" and insert -- iodoadenosine --.

Column 48, Line 40, delete "diisoropyl" and insert -- diisopropyl --.

Column 54, Line 9 (approx.), delete "diisoropyl" and insert -- diisopropyl --.

Column 54, Line 41, delete "mol/g." and insert -- µmol/g. --.

Column 59, Line 3, delete "Pd(PPh3)4" and insert -- Pd(PPh$_3$)$_4$ --.

Column 59, Line 34 (approx.), delete "diisoropyl" and insert -- diisopropyl --.

Column 60, Line 31 (approx.), delete "mol/g." and insert -- µmol/g. --.

Column 61-62, Lines 1-10 (approx.), delete " 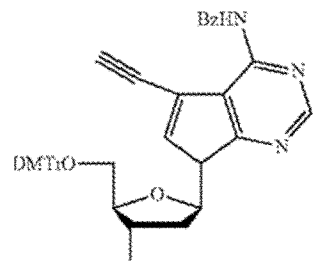 " and

CERTIFICATE OF CORRECTION (continued)
U.S. Pat. No. 11,649,260 B2 insert -- 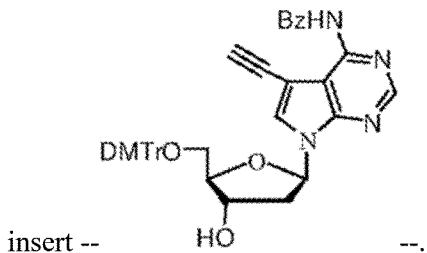 --.

Column 61, Line 46, delete "isodoadenosine" and insert -- iodoadenosine --.

Column 63, Line 1, delete "diisoropyl" and insert -- diisopropyl --.

In the Claims

Column 73, Line 49 (approx.), Claim 1, delete "hetetroarylene," and insert -- heteroarylene, --.

Column 75, Line 1, Claim 4, after "compound of" delete "any one of".

Column 76, Line 19 (approx.), Claim 9, after "of" delete "any".

Column 76, Line 61, Claim 17, delete "—[(CH$_2$)$_2$O]$_{1-5}$" and insert -- —[(CH$_2$)$_2$O]$_{1-5}$ --.

Column 76, Line 62, Claim 17, delete "—[(CH$_2$)$_2$O](CH$_2$)$_{1-4}$—." and insert -- —[(CH$_2$)$_2$O]$_{1-5}$(CH$_2$)$_{1-4}$—. --.